United States Patent
Lee et al.

(10) Patent No.: US 10,961,271 B2
(45) Date of Patent: Mar. 30, 2021

(54) METHODS OF MODULATING KEAP1

(71) Applicant: Ionis Pharmaceuticals, Inc., Carlsbad, CA (US)

(72) Inventors: Richard Lee, Oceanside, CA (US); Jeffrey R. Crosby, Carlsbad, CA (US)

(73) Assignee: Ionis Pharmaceuticals, Inc., Carlsbad, CA (US)

( * ) Notice: Subject to any disclaimer, the term of this patent is extended or adjusted under 35 U.S.C. 154(b) by 77 days.

(21) Appl. No.: 16/085,130

(22) PCT Filed: Mar. 16, 2017

(86) PCT No.: PCT/US2017/022788
§ 371 (c)(1),
(2) Date: Sep. 18, 2018

(87) PCT Pub. No.: WO2017/161172
PCT Pub. Date: Sep. 21, 2017

(65) Prior Publication Data
US 2019/0077825 A1    Mar. 14, 2019

Related U.S. Application Data

(60) Provisional application No. 62/394,663, filed on Sep. 14, 2016, provisional application No. 62/309,360, filed on Mar. 16, 2016.

(51) Int. Cl.
| C07H 21/02 | (2006.01) |
|---|---|
| A61K 31/7125 | (2006.01) |
| A61K 31/7115 | (2006.01) |
| A61K 31/713 | (2006.01) |
| A61K 31/712 | (2006.01) |
| C07H 21/04 | (2006.01) |
| C12N 15/113 | (2010.01) |
| A61P 9/10 | (2006.01) |
| A61P 25/28 | (2006.01) |
| A61P 11/06 | (2006.01) |
| A61P 3/10 | (2006.01) |
| A61P 29/00 | (2006.01) |

(52) U.S. Cl.
CPC .......... *C07H 21/02* (2013.01); *A61K 31/712* (2013.01); *A61K 31/713* (2013.01); *A61K 31/7115* (2013.01); *A61K 31/7125* (2013.01); *A61P 3/10* (2018.01); *A61P 9/10* (2018.01); *A61P 11/06* (2018.01); *A61P 25/28* (2018.01); *A61P 29/00* (2018.01); *C07H 21/04* (2013.01); *C12N 15/113* (2013.01); *C12N 15/1138* (2013.01); *C12N 2310/11* (2013.01); *C12N 2310/315* (2013.01); *C12N 2310/3231* (2013.01); *C12N 2310/341* (2013.01); *C12N 2310/346* (2013.01); *C12N 2320/30* (2013.01)

(58) Field of Classification Search
None
See application file for complete search history.

(56) References Cited

U.S. PATENT DOCUMENTS

| 3,687,808 A | 8/1972 | Merigan et al. |
|---|---|---|
| 4,415,732 A | 11/1983 | Caruthers et al. |
| 4,458,066 A | 7/1984 | Caruthers et al. |
| 4,469,863 A | 9/1984 | Ts'o et al. |
| 4,476,301 A | 10/1984 | Imbach et al. |
| 4,500,707 A | 2/1985 | Caruthers et al. |
| 4,668,777 A | 5/1987 | Caruthers et al. |
| 4,725,677 A | 2/1988 | Koster et al. |
| 4,845,205 A | 7/1989 | Huynh Dinh et al. |
| 4,973,679 A | 11/1990 | Caruthers et al. |
| 4,981,957 A | 1/1991 | Lebleu et al. |
| 5,013,830 A | 5/1991 | Ohtsuka et al. |
| 5,023,243 A | 6/1991 | Tullis |
| 5,034,506 A | 7/1991 | Summerton et al. |
| 5,118,800 A | 6/1992 | Smith et al. |
| 5,130,302 A | 7/1992 | Spielvogel et al. |
| 5,132,418 A | 7/1992 | Caruthers et al. |
| 5,134,066 A | 7/1992 | Rogers et al. |
| RE34,036 E | 8/1992 | McGeehan |
| 5,149,797 A | 9/1992 | Pederson et al. |
| 5,166,315 A | 11/1992 | Summerton et al. |
| 5,175,273 A | 12/1992 | Bischofberger et al. |
| 5,177,196 A | 1/1993 | Meyer, Jr. et al. |

(Continued)

FOREIGN PATENT DOCUMENTS

| EP | 2420119 | 7/2013 |
|---|---|---|
| WO | WO 2007/005879 | 1/2007 |

(Continued)

OTHER PUBLICATIONS

Aminzadeh et al., "The synthetic triterpenoid RTA dh404 (CDDO-dhTFEA) restores endothelial function impaired by reduced Nrf2 activity in chronic kidney disease" Redox Biol (2013) 527-531.
An et al., "An inflammation-independent contraction mechanophenotype of airway smooth muscle in asthma" J Allergy Clin Immunol (2016) 138: 294-297.
Branch et al., "A good antisense molecule is hard to find," TIBS (1998) 23:45-50.
Browning et al., "Molecular mediators of hepatic steatosis and liver injury" J Clin Invest (2004) 114(2): 147-152.
Chambel et al., "The Dual Role of Nrf2 in Nonalcoholic Fatty Liver Disease: Regulation of Antioxidant Defenses and Hepatic Lipid Metabolism" Biomed. Res. (2015) 1-11.

(Continued)

*Primary Examiner* — Tracy Vivlemore
(74) *Attorney, Agent, or Firm* — Knobbe, Martens, Olson & Bear, LLP

(57) ABSTRACT

Provided herein are methods, compounds, and compositions for reducing expression of KEAP1 in animal. Such methods, compounds, and compositions are useful to treat, prevent, delay, or ameliorate oxidative stress or a disease, disorder or condition related to oxidative stress an animal in need. Diseases, disorders or conditions related to oxidative stress include NASH, NAFLD, asthma and insulin resistance.

40 Claims, No Drawings
Specification includes a Sequence Listing.

(56) References Cited

U.S. PATENT DOCUMENTS

| | | | |
|---|---|---|---|
| 5,177,198 | A | 1/1993 | Spielvogel et al. |
| 5,188,897 | A | 2/1993 | Suhadolnik et al. |
| 5,194,599 | A | 3/1993 | Froehler et al. |
| 5,214,134 | A | 5/1993 | Weis et al. |
| 5,216,141 | A | 6/1993 | Benner |
| 5,220,007 | A | 6/1993 | Pederson et al. |
| 5,223,618 | A | 6/1993 | Cook et al. |
| 5,235,033 | A | 8/1993 | Summerton et al. |
| 5,256,775 | A | 10/1993 | Froehler |
| 5,264,423 | A | 11/1993 | Cohen et al. |
| 5,264,562 | A | 11/1993 | Matteucci |
| 5,264,564 | A | 11/1993 | Matteucci |
| 5,185,444 | A | 12/1993 | Summerton et al. |
| 5,276,019 | A | 1/1994 | Cohen et al. |
| 5,278,302 | A | 1/1994 | Caruthers et al. |
| 5,286,717 | A | 2/1994 | Cohen et al. |
| 5,319,080 | A | 6/1994 | Leumann |
| 5,321,131 | A | 6/1994 | Agrawal et al. |
| 5,359,044 | A | 10/1994 | Cook et al. |
| 5,366,878 | A | 11/1994 | Pederson et al. |
| 5,367,066 | A | 11/1994 | Urdea et al. |
| 5,378,825 | A | 1/1995 | Cook et al. |
| 5,386,023 | A | 1/1995 | Sanghvi et al. |
| 5,393,878 | A | 2/1995 | Leumann |
| 5,399,676 | A | 3/1995 | Froehler |
| 5,403,711 | A | 4/1995 | Walder et al. |
| 5,405,938 | A | 4/1995 | Sumerton et al. |
| 5,405,939 | A | 4/1995 | Suhadolnik et al. |
| 5,432,272 | A | 7/1995 | Benner |
| 5,434,257 | A | 7/1995 | Matteucci |
| 5,446,137 | A | 8/1995 | Maag et al. |
| 5,453,496 | A | 9/1995 | Caruthers et al. |
| 5,455,233 | A | 10/1995 | Spielvogel et al. |
| 5,457,187 | A | 10/1995 | Gmelner et al. |
| 5,457,191 | A | 10/1995 | Cook et al. |
| 5,459,255 | A | 10/1995 | Cook et al. |
| 5,466,677 | A | 11/1995 | Baxter et al. |
| 5,466,786 | A | 11/1995 | Burh et al. |
| 5,470,967 | A | 11/1995 | Huie et al. |
| 5,476,925 | A | 12/1995 | Letsinger et al. |
| 5,484,908 | A | 1/1996 | Froehler et al. |
| 5,489,677 | A | 2/1996 | Sanghvi et al. |
| 5,491,133 | A | 2/1996 | Walder et al. |
| 5,502,177 | A | 3/1996 | Matteucci et al. |
| 5,508,270 | A | 4/1996 | Baxter et al. |
| 5,514,785 | A | 5/1996 | Van Ness et al. |
| 5,519,126 | A | 5/1996 | Hecht |
| 5,519,134 | A | 5/1996 | Acevedo et al. |
| 5,525,711 | A | 6/1996 | Hawkins et al. |
| 5,527,899 | A | 6/1996 | Froehler |
| 5,536,821 | A | 7/1996 | Agrawal et al. |
| 5,541,306 | A | 7/1996 | Agrawal et al. |
| 5,541,307 | A | 7/1996 | Cook et al. |
| 5,550,111 | A | 8/1996 | Suhadolnik et al. |
| 5,552,540 | A | 9/1996 | Haralambidis |
| 5,561,225 | A | 10/1996 | Maddry et al. |
| 5,563,253 | A | 10/1996 | Agrawal et al. |
| 5,565,350 | A | 10/1996 | Kmiec |
| 5,565,555 | A | 10/1996 | Froehler et al. |
| 5,567,811 | A | 10/1996 | Mistura et al. |
| 5,571,799 | A | 11/1996 | Tkachuk et al. |
| 5,576,427 | A | 11/1996 | Cook et al. |
| 5,587,361 | A | 12/1996 | Cook et al. |
| 5,587,469 | A | 12/1996 | Cook et al. |
| 5,587,470 | A | 12/1996 | Cook et al. |
| 5,591,722 | A | 1/1997 | Montgomery et al. |
| 5,594,121 | A | 1/1997 | Froehler et al. |
| 5,596,086 | A | 1/1997 | Matteucci |
| 5,596,091 | A | 1/1997 | Switzer |
| 5,597,909 | A | 1/1997 | Urdea et al. |
| 5,602,240 | A | 2/1997 | De Mesmaeker et al. |
| 5,608,046 | A | 3/1997 | Cook et al. |
| 5,610,289 | A | 3/1997 | Cook et al. |
| 5,610,300 | A | 3/1997 | Altmann et al. |
| 5,614,617 | A | 3/1997 | Cook et al. |
| 5,618,704 | A | 4/1997 | Sanghvi et al. |
| 5,623,065 | A | 4/1997 | Cook et al. |
| 5,623,070 | A | 4/1997 | Cook et al. |
| 5,625,050 | A | 4/1997 | Beaton et al. |
| 5,627,053 | A | 5/1997 | Usman et al. |
| 5,633,360 | A | 5/1997 | Bishofberger et al. |
| 5,639,873 | A | 6/1997 | Barascut et al. |
| 5,645,985 | A | 7/1997 | Froehler et al. |
| 5,646,265 | A | 7/1997 | McGee |
| 5,646,269 | A | 7/1997 | Matteucci |
| 5,652,355 | A | 7/1997 | Metelev et al. |
| 5,652,356 | A | 7/1997 | Agrawal |
| 5,663,312 | A | 9/1997 | Chaturvedula |
| 5,670,633 | A | 9/1997 | Cook et al. |
| 5,672,697 | A | 9/1997 | Buhr et al. |
| 5,677,437 | A | 10/1997 | Teng et al. |
| 5,677,439 | A | 10/1997 | Weis et al. |
| 5,681,941 | A | 10/1997 | Cook et al. |
| 5,698,685 | A | 12/1997 | Summerton et al. |
| 5,700,920 | A | 12/1997 | Altmann et al. |
| 5,700,922 | A | 12/1997 | Cook |
| 5,721,218 | A | 2/1998 | Froehler |
| 5,750,692 | A | 5/1998 | Cook et al. |
| 5,763,588 | A | 6/1998 | Matteucci et al. |
| 5,792,608 | A | 8/1998 | Swaminathan et al. |
| 5,792,847 | A | 8/1998 | Burh et al. |
| 5,801,154 | A | 9/1998 | Baracchini et al. |
| 5,808,027 | A | 9/1998 | Cook et al. |
| 5,830,653 | A | 11/1998 | Froehler et al. |
| 5,859,221 | A | 1/1999 | Cook et al. |
| 5,948,903 | A | 9/1999 | Cook et al. |
| 5,994,517 | A | 11/1999 | Ts'O |
| 6,005,087 | A | 12/1999 | Cook et al. |
| 6,005,096 | A | 12/1999 | Matteucci et al. |
| 6,166,199 | A | 12/2000 | Cook et al. |
| 6,268,490 | B1 | 7/2001 | Imanishi et al. |
| 6,300,319 | B1 | 10/2001 | Manoharan |
| 6,426,220 | B1 | 7/2002 | Bennett et al. |
| 6,525,191 | B1 | 2/2003 | Ramasamy |
| 6,531,584 | B1 | 3/2003 | Cook et al. |
| 6,582,908 | B2 | 6/2003 | Fodor et al. |
| 6,600,032 | B1 | 7/2003 | Manoharan et al. |
| 6,660,720 | B2 | 12/2003 | Manoharan |
| 6,670,461 | B1 | 12/2003 | Wengel et al. |
| 6,770,748 | B2 | 8/2004 | Imanishi et al. |
| 6,794,499 | B2 | 9/2004 | Wengel et al. |
| 6,906,182 | B2 | 6/2005 | Ts'o et al. |
| 7,015,315 | B1 | 3/2006 | Cook et al. |
| 7,034,133 | B2 | 4/2006 | Wengel et al. |
| 7,053,207 | B2 | 5/2006 | Wengel et al. |
| 7,101,993 | B1 | 9/2006 | Cook et al. |
| 7,262,177 | B2 | 8/2007 | Ts'o et al. |
| 7,399,845 | B2 | 7/2008 | Seth et al. |
| 7,427,672 | B2 | 9/2008 | Imanishi et al. |
| 7,491,805 | B2 | 2/2009 | Vargeese et al. |
| 7,547,684 | B2 | 6/2009 | Seth et al. |
| 7,569,686 | B1 | 8/2009 | Bhat et al. |
| 7,572,582 | B2 | 8/2009 | Wengel et al. |
| 7,666,854 | B2 | 2/2010 | Seth et al. |
| 7,691,997 | B2 | 4/2010 | Khvorova et al. |
| 7,696,345 | B2 | 4/2010 | Allerson et al. |
| 7,723,509 | B2 | 5/2010 | Manoharan et al. |
| 7,741,457 | B2 | 6/2010 | Swayze et al. |
| 7,750,131 | B2 | 7/2010 | Seth et al. |
| 7,875,733 | B2 | 1/2011 | Bhat et al. |
| 7,939,677 | B2 | 5/2011 | Bhat et al. |
| 8,022,193 | B2 | 9/2011 | Swayze et al. |
| 8,030,467 | B2 | 10/2011 | Seth et al. |
| 8,034,909 | B2 | 10/2011 | Wengel et al. |
| 8,080,644 | B2 | 12/2011 | Wengel et al. |
| 8,088,746 | B2 | 1/2012 | Seth et al. |
| 8,088,904 | B2 | 1/2012 | Swayze et al. |
| 8,106,022 | B2 | 1/2012 | Manoharan et al. |
| 8,124,745 | B2 | 2/2012 | Allerson et al. |
| 8,153,365 | B2 | 4/2012 | Wengel et al. |
| 8,268,980 | B2 | 9/2012 | Seth et al. |
| 8,278,283 | B2 | 10/2012 | Seth et al. |
| 8,278,425 | B2 | 10/2012 | Prakash et al. |
| 8,278,426 | B2 | 10/2012 | Seth et al. |

(56) References Cited

U.S. PATENT DOCUMENTS

| | | | |
|---|---|---|---|
| 8,440,803 B2 | 5/2013 | Swayze et al. | |
| 8,501,805 B2 | 8/2013 | Seth et al. | |
| 8,530,640 B2 | 9/2013 | Seth et al. | |
| 8,546,556 B2 | 10/2013 | Seth et al. | |
| RE44,779 E | 2/2014 | Imanishi et al. | |
| 8,653,047 B2* | 2/2014 | Crooke .............. | C12N 15/1136 514/44 A |
| 8,785,408 B2 | 7/2014 | Feinstein et al. | |
| 8,828,956 B2 | 9/2014 | Manoharan et al. | |
| 9,005,906 B2 | 4/2015 | Swayze et al. | |
| 9,012,421 B2 | 4/2015 | Migawa et al. | |
| 9,127,276 B2 | 8/2015 | Prakash et al. | |
| 9,139,592 B2 | 9/2015 | Batist et al. | |
| 9,290,760 B2 | 3/2016 | Rajeev et al. | |
| 2001/0053519 A1 | 12/2001 | Fodor et al. | |
| 2003/0082807 A1 | 5/2003 | Wengel | |
| 2003/0158403 A1 | 8/2003 | Manoharan et al. | |
| 2003/0175906 A1 | 9/2003 | Manoharan et al. | |
| 2003/0207841 A1 | 11/2003 | Kaneko et al. | |
| 2003/0224377 A1 | 12/2003 | Wengel et al. | |
| 2003/0228597 A1 | 12/2003 | Cowsert et al. | |
| 2004/0143114 A1 | 7/2004 | Imanishi et al. | |
| 2004/0171570 A1 | 9/2004 | Allerson et al. | |
| 2004/0192918 A1 | 9/2004 | Imanishi et al. | |
| 2005/0130923 A1 | 6/2005 | Bhat et al. | |
| 2006/0148740 A1 | 7/2006 | Platenburg | |
| 2007/0031844 A1 | 2/2007 | Khvorova et al. | |
| 2008/0039618 A1 | 2/2008 | Allerson et al. | |
| 2010/0190837 A1 | 7/2010 | Migawa et al. | |
| 2010/0197762 A1 | 8/2010 | Swayze et al. | |
| 2011/0123520 A1 | 5/2011 | Manoharan et al. | |
| 2011/0250300 A1* | 10/2011 | Biswal ................. | A01K 67/027 424/752 |
| 2011/0288155 A1 | 11/2011 | Feinstein et al. | |
| 2013/0130378 A1 | 5/2013 | Manoharan et al. | |
| 2013/0203836 A1 | 8/2013 | Rajeev et al. | |
| 2013/0298263 A1 | 11/2013 | Iwawaki et al. | |
| 2014/0107330 A1 | 4/2014 | Freier et al. | |
| 2014/0256767 A1 | 9/2014 | Rutgers et al. | |
| 2015/0018540 A1 | 1/2015 | Prakash et al. | |
| 2015/0080462 A1 | 3/2015 | Biswal et al. | |
| 2015/0184153 A1 | 7/2015 | Freier et al. | |
| 2015/0191727 A1 | 7/2015 | Migawa et al. | |
| 2015/0267195 A1 | 9/2015 | Seth et al. | |
| 2015/0275212 A1 | 10/2015 | Albaek et al. | |

FOREIGN PATENT DOCUMENTS

| | | |
|---|---|---|
| WO | WO 2008/057434 | 5/2008 |
| WO | WO 2013/170068 | 11/2013 |

OTHER PUBLICATIONS

Chartoumpekis et al., "Keap1/Nrf2 pathway in the frontiers of cancer and non-cancer cell metabolism" Biochem Soc Trans (2015) 43(4): 639-644.
Chin "On the Preparation and Utilization of Isolated and Purified Oligonucleotides" Document purportedly located on a CD-ROM and contributed to the public collection of the Katherine R. Everett Law Library of the University of North Carolina on Mar. 14, 2002.
Cleary et al., "Identification of driver genes in hepatocellular carcinoma by exome sequencing" Hepatology (2013) 58(5): 1693-1702.
Crooke et al., "Basic Principles of Antisense Therapeutics" Antisense Research and Application (1998) Chapter 1:1-50.
De Zeeuw et al., "Bardoxolone methyl in type 2 diabetes and stage 4 chronic kidney disease" N Engl J Med (2013) 369(26). 2492-2503.
Ganan-Gomez et al., "Oncogenic functions of the transcription factor Nrf2" Free Radic Biol Med (2013) 65: 750-764.
Gao et al., "Induction of phase 2 genes by sulforaphane protects retinal pigment epithelial cells against photooxidative damage" Proc Natl Acad Sci USA (2004) 101(28): 10446-10451.

Gonzalez-Rodriguez et al., "In vivo siRNA delivery of Keap1 modulates death and survival signaling pathways and attenuates concanavalin-A-induced acute liver injury in mice" Dis Model Mech (2014) 7(9): 1093-1100.
Hardwick et al., "Diversity in antioxidant response enzymes in progressive stages of human nonalcoholic fatty liver disease" Drug Metlab Dispos (2010) 38(12): 2293-2301.
International Search Report for PCT/US2017/022788 dated Jun. 5, 2017.
Kulkarni et al., "Caloric restriction-mediated induction of lipid metabolism gene expression in liver is enhanced by Keap1-knockdown" Pharm Res (2013) 30(9): 2221-2231.
Lo et al., "PGAM5, a Bc1-XL-interacting protein, is a novel substrate for the redox-regulated Keap1-dependent ubiquitin ligase complex" J Biol Chem (2006) 281(49) 37893-37903.
Meakin et al., "Susceptibility of Nrf2-null mice to steatohepatitis and cirrhosis upon consumption of a high-fat diet is associated with oxidative stress, perturbation of the unfolded protein response, and disturbance in the expression of metabolic enzymes but not with insulin resistance" Mol Cell Biol (2014) 34(17): 3305-3320.
New England Biolabs 1998/99 Catalog (cover page and pp. 121 and 284).
Okada et al., "Deletion of Nrf2 leads to rapid progression of steatohepatitis in mice fed atherogenic plus high-fat diet" J Gastroenterol (2013) 48(5): 620-632.
Padmanabhan et al., "Structural basis for defects of Keap1 activity provoked by its point mutations in lung cancer" Mol Cell (2006) 21(5): 689-700.
Ramadori et al., "Hepatocyte-specific Keap1 deletion reduces liver steatosis but not inflammation during non-alcoholic steatohepatitis development" Free Radic Biol Med (2016) 91: 114-126.
Reynolds et al., "Rational siRNA design for RNA interference" Nature Biotechnology (2004) 22(3):326-330.
Sanghvi et al., "Heterocyclic Base Modifications in Nucleic Acids and Their Applications in Antisense Oligonucleotides" Antisense Research and Applications (1993) pp. 273-288.
Schulze et al., "Exome sequencing of hepatocellular carcinomas identifies new mutational signatures and potential therapeutic targets" Nat Genet (2015) 47(5): 505-511.
Shimamura et al., "Leptin and insulin down-regulate angiopoietin-like protein 3, a plasma triglyceride-increasing factor" Biochem Biophys Res Commun (2004) 322(3): 1080-1085.
Shimozono et al., "Nrf2 activators attenuate the progression of nonalcoholic steatohepatitis-related fibrosis in a dietary rat model" Mol Pharmacol (2013) 84(1): 62-70.
Shin et al., "Preparation and evaluation of tacrolimus-loaded nanoparticles for lymphatic delivery" Eur J Pharm Biopharm (2010) 74: 164-171.
Soares et al., "Restoration of Nrf2 Signaling Normalizes the Regenerative Niche" Diabetes (2016) 65(3): 633-646.
Sun et al., "Keap1 controls postinduction repression of the Nrf2-mediated antioxidant response by escorting nuclear export of Nrf2" Mol Cell Biol (2007) 27(18): 6334-6349.
Taguchi et al., "Genetic analysis of cytoprotective functions supported by graded expression of Keap1" Mol Cell Biol (2010) 30(12): 3016-3026.
Uruno et al., "The Keap1-Nrf2 system prevents onset of diabetes mellitus" Mol Cell Biol (2013) 33(15): 2996-3010.
Wakabayashi et al., "Keap1-null mutation leads to postnatal lethality due to constitutive Nrf2 activation" Nat Genet (2003) 35(3): 238-245.
Wang et al., "Bardoxolone methyl (CDDO-Me) as a therapeutic agent: an update on its pharmacokinetic and pharmacodynamic properties" Drug Des Devel Ther (2014) 8: 2075-2088.
Xu et al., "Keap1-knockdown decreases fasting-induced fatty liver via altered lipid metabolism and decreased fatty acid mobilization from adipose tissue" PLoS One (2013) 8(11): e79841.
Xu et al., "KEAP1 is a redox sensitive target that arbitrates the opposing radiosensitive effects of parthenolide in normal and cancer cells" Cancer Res (2013) 73(14): 4406-4417.

(56) References Cited

OTHER PUBLICATIONS

Yates et al., "Genetic versus chemoprotective activation of Nrf2 signaling: overlapping yet distinct gene expression profiles between Keap1 knockout and triterpenoid-treated mice" Carcinogenesis (2009) 30(6): 1024-1031.

Zhong et al., "Transcription factor Nrf2-mediated antioxidant defense system in the development of diabetic retinopathy" Invest Opthalmol Vis Sci (2013) 54(6): 3941-3948.

Crooke, ST., et al., "Antisense Drug Technology" Second Edition, CRC Press (2008) Chapters 1-28.

Egli, et al., "Synthesis, improved antisense activity and structural rationale for the divergent RNA affinities of 3'-fluoro hexitol nucleic acid (FHNA and Ara-FHNA) modified oligonucleotides." J Am Chem (2011) 133(41):16642-16649.

Gautschi et al., "Activity of a novel bc1-2/bc1-xLbispecific antisense oligonucleotide against tumors of diverse histologic origins" J. Natl. Cancer Inst. (2001) 93:463-471.

Maher et al., "Comparative hybrid arrest by tandem antisense oligodeoxyribonucleotides or oligodeoxyribonucleoside methylpbosphonates in a cell-free system" Nucl. Acid. Res. (1988) 16(8):3341-3358.

Seth et al., "Short Antisense Oligonucleotides with Novel 2'-4' Conformationaly Restricted Nucleoside Analogues Show Improved Potency Without Increased Toxicity in Animals " J Med Chem (2009) 52:10-13.

Woolf et al., "Specificity of antisense oligonucleotides in vivo" PNAS (1992) 89: 7305-7309.

Hayashi et al., "The autophagy pathway maintained signaling crosstalk with the Keap1-Nrf2 system through p62 in auditory cells under oxidative stress" Cell Signal (2015) 27: 382-393.

Singh et al., "Glutathione peroxidase 2, the major cigarette smoke-inducible isoform of GPX in lungs, is regulated by Nrf2" Am J Respir Cell Mol Biol (2006) 35: 639-650.

Thai et al., "Characterization of a novel long noncoding RNA, SCAL1, induced by cigarette smoke and elevated in lung cancer cell lines" Am J Respir Cell Mol Biol (2013) 49: 204-211.

Yan et al., "Punicalagin attenuates palmitate-induced lipotoxicity in HepG2 cells by activating the Keap1-Nrf2 antioxidant defense system" Mol Nutr Food Res (2016) 60: 1139-1149.

Youn et al., "Cytoprotection against beta-amyloid (Aβ) peptide-mediated oxidative damage and autophagy by Keapl RNAi in human glioma U87mg cells" Neurosci Res (2015) 94: 70-78.

Extended EP Search Report for 17767564.2 dated Sep. 20, 2019.

* cited by examiner

SEQUENCE LISTING

<160> NUMBER OF SEQ ID NOS: 38

<210> SEQ ID NO 1
<211> LENGTH: 2606
<212> TYPE: DNA
<213> ORGANISM: Homo sapiens

<400> SEQUENCE: 1

| | | | | | |
|---|---|---|---|---|---|
| ctttccgccc | tctcccgcc | tccttttcgg | gcgtcccgag | gccgctcccc | aaccgacaac | 60 |
| caagaccccg | caggccacgc | agccctggag | ccgaggcccc | ccgacggcgg | aggcgcccgc | 120 |
| gggtcccta | cagccaaggt | ccctgagtgc | cagaggtggt | ggtgttgctt | atcttctgga | 180 |
| accccatgca | gccagatccc | aggcctagcg | gggctggggc | ctgctgccga | ttcctgcccc | 240 |
| tgcagtcaca | gtgccctgag | ggggcagggg | acgcggtgat | gtacgcctcc | actgagtgca | 300 |
| aggcggaggt | gacgccctcc | cagcatggca | accgcacctt | cagctacacc | ctggaggatc | 360 |
| ataccaagca | ggcctttggc | atcatgaacg | agctgcggct | cagccagcag | ctgtgtgacg | 420 |
| tcacactgca | ggtcaagtac | caggatgcac | cggccgccca | gttcatggcc | cacaaggtgg | 480 |
| tgctggcctc | atccagccct | gtcttcaagg | ccatgttcac | caacgggctg | cgggagcagg | 540 |
| gcatggaggt | ggtgtccatt | gagggtatcc | accccaaggt | catggagcgc | ctcattgaat | 600 |
| tcgcctacac | ggcctccatc | tccatgggcg | agaagtgtgt | cctccacgtc | atgaacggtg | 660 |
| ctgtcatgta | ccagatcgac | agcgttgtcc | gtgcctgcag | tgacttcctg | gtgcagcagc | 720 |
| tggaccccag | caatgccatc | ggcatcgcca | acttcgctga | gcagattggc | tgtgtggagt | 780 |
| tgcaccagcg | tgcccgggag | tacatctaca | tgcattttgg | ggaggtggcc | aagcaagagg | 840 |
| agttcttcaa | cctgtcccac | tgccaactgg | tgaccctcat | cagccgggac | gacctgaacg | 900 |
| tgcgctgcga | gtccgaggtc | ttccacgcct | gcatcaactg | ggtcaagtac | gactgcgaac | 960 |
| agcgacggtt | ctacgtccag | gcgctgctgc | gggccgtgcg | ctgccactcg | ttgacgccga | 1020 |
| acttcctgca | gatgcagctg | cagaagtgcg | agatcctgca | gtccgactcc | cgctgcaagg | 1080 |
| actacctggt | caagatcttc | gaggagctca | ccctgcacaa | gcccacgcag | gtgatgcct | 1140 |
| gccgggcgcc | caaggtgggc | cgcctgatct | acaccgcggg | cggctacttc | cgacagtcgc | 1200 |
| tcagctacct | ggaggcttac | aaccccagtg | acggcacctg | gctccggttg | gcggacctgc | 1260 |
| aggtgccgcg | gagcggcctg | gccggctgcg | tggtgggcgg | gctgttgtac | gccgtgggcg | 1320 |
| gcaggaacaa | ctcgcccgac | ggcaacaccg | actccagcgc | cctggactgt | acaaccccca | 1380 |
| tgaccaatca | gtggtcgccc | tgcgccccca | tgagcgtgcc | ccgtaaccgc | atcgggtgg | 1440 |
| gggtcatcga | tggccacatc | tatgccgtcg | gcggctccca | cggctgcatc | caccacaaca | 1500 |
| gtgtggagag | gtatgagcca | gagcgggatg | agtggcactt | ggtggcccca | atgctgacac | 1560 |
| gaaggatcgg | ggtgggcgtg | gctgtcctca | atcgtctcct | ttatgccgtg | gggggctttg | 1620 |
| acgggacaaa | ccgccttaat | tcagctgagt | gttactaccc | agagaggaac | gagtggcgaa | 1680 |
| tgatcacagc | aatgaacacc | atccgaagcg | gggcaggcgt | ctgcgtcctg | cacaactgta | 1740 |
| tctatgctgc | tgggggctat | gatggtcagg | accagctgaa | cagcgtggag | cgctacgatg | 1800 |
| tggaaacaga | gacgtggact | ttcgtagccc | ccatgaagca | ccggcgaagt | gccctgggga | 1860 |
| tcactgtcca | ccaggggaga | atctacgtcc | ttggaggcta | tgatggtcac | acgttcctgg | 1920 |
| acagtgtgga | gtgttacgac | ccagatacag | acacctggag | cgaggtgacc | cgaatgacat | 1980 |
| cgggccggag | tgggtgggc | gtggctgtca | ccatggagcc | ctgccggaag | cagattgacc | 2040 |
| agcagaactg | tacctgttga | ggcactttg | tttcttgggc | aaaaatacag | tccaatgggg | 2100 |

```
agtatcattg tttttgtaca aaaaccggga ctaaaagaaa agacagcact gcaaataacc    2160
catcttccgg gaagggaggc caggatgcct cagtgttaaa atgacatctc aaaagaagtc    2220
caaagcggga atcatgtgcc cctcagcgga gccccgggag tgtccaagac agcctggctg    2280 ggaaggggg tgtggaaaga gcaggcttcc aggagagagg cccccaaacc ctctggccgg    2340
gtaataggcc tgggtcccac tcacccatgc cggcagctgt caccatgtga tttattcttg    2400
gataccgggg agggggccaa tgggggcctc aggggaggc ccctctgga aatgtggttc    2460 ccagggatgg gcctgtacat agaagccacc ggatggcact tccccaccgg atggacagtt    2520
attttgttga taagtaaccc tgtaattttc caaggaaaat aaagaacaga ctaactagtg    2580
tctttcaccc tgaaaaaaaa aaaaaa                                        2606
```

<210> SEQ ID NO 2
<211> LENGTH: 2577
<212> TYPE: DNA
<213> ORGANISM: Homo sapiens

<400> SEQUENCE: 2

```
tctgcttagt catggtgacc tgcgcgcgct ccgcgcctcc cccacgcgca gcgatggagg      60
cgccggggct cgggcggtgg aggcggagcc ggagcgcggc catggcgggg tccctgagtg     120
ccagaggtgg tggtgttgct tatcttctgg aacccatgc agccagatcc caggcctagc     180
ggggctgggg cctgctgccg attcctgccc ctgcagtcac agtgccctga ggggcaggg     240 gacgcggtga tgtacgcctc cactgagtgc aaggcggagg tgacgccctc ccagcatggc     300
aaccgcacct tcagctacac cctggaggat cataccaagc aggcctttgg catcatgaac     360
gagctgcggc tcagccagca gctgtgtgac gtcacactgc aggtcaagta ccaggatgca     420
ccggccgccc agttcatggc ccacaaggtg gtgctggcct catccagccc tgtcttcaag     480
gccatgttca ccaacgggct gcgggagcag ggcatggagg tggtgtccat tgagggtatc     540 cacccccaagg tcatggagcg cctcattgaa ttcgcctaca cggcctccat ctccatgggc     600
gagaagtgtg tcctccacgt catgaacggt gctgtcatgt accagatcga cagcgttgtc     660
cgtgcctgca gtgacttcct ggtgcagcag ctggacccca gcaatgccat cggcatcgcc     720
aacttcgctg agcagattgg ctgtgtggag ttgcaccagc gtgcccggga gtacatctac     780
atgcattttg gggaggtggc caagcaagag gagttcttca acctgtccca ctgccaactg     840
gtgaccctca tcagccggga cgacctgaac gtgcgctgcg agtccgaggt cttccacgcc     900
tgcatcaact gggtcaagta cgactgcgaa cagcgacggt tctacgtcca ggcgctgctg     960
cgggccgtgc gctgccactc gttgacgccg aacttcctgc agatgcagct gcagaagtgc    1020
gagatcctgc agtccgactc ccgctgcaag gactacctgg tcaagatctt cgaggagctc    1080
accctgcaca agcccacgca ggtgatgccc tgccgggcgc ccaaggtggg ccgcctgatc    1140
tacaccgcgg cggctacttt ccgacagtcg ctcagctacc tggaggctta caaccccagt    1200
gacggcacct ggctccggtt ggcggacctg caggtgccgc ggagcggcct ggccggctgc    1260
gtggtgggcg gctgttgta cgccgtgggc ggcaggaaca actcgcccga cggcaacacc    1320
gactccagcg ccctggactg ttacaacccc atgaccaatc agtggtcgcc ctgcgccccc    1380
atgagcgtgc cccgtaaccg catcggggtg ggggtcatcg atggccacat ctatgccgtc    1440
ggcggctccc acggctgcat ccaccacaac agtgtggaga ggtatgagcc agagcgggat    1500
gagtggcact tggtggcccc aatgctgaca cgaaggatcg gggtgggcgt ggctgtcctc    1560
```

```
aatcgtctcc tttatgccgt gggggcttt  gacgggacaa accgccttaa ttcagctgag    1620
tgttactacc cagagaggaa cgagtggcga atgatcacag caatgaacac catccgaagc    1680
ggggcaggcg tctgcgtcct gcacaactgt atctatgctg ctgggggcta tgatggtcag    1740
gaccagctga acagcgtgga gcgctacgat gtggaaacag agacgtggac tttcgtagcc    1800
cccatgaagc accggcgaag tgccctgggg atcactgtcc accaggggag aatctacgtc    1860
cttggaggct atgatggtca cacgttcctg gacagtgtgg agtgttacga cccagataca    1920
gacacctgga gcgaggtgac ccgaatgaca tcggccgga  gtggggtggg cgtggctgtc    1980
accatggagc cctgccggaa gcagattgac cagcagaact gtacctgttg aggcactttt    2040
gtttcttggg caaaaataca gtccaatggg gagtatcatt gttttgtac  aaaaaccggg    2100
actaaaagaa aagacagcac tgcaaataac ccatcttccg ggaagggagg ccaggatgcc    2160
tcagtgttaa aatgacatct caaaagaagt ccaaagcggg aatcatgtgc ccctcagcgg    2220
agccccggga gtgtccaaga cagcctggct gggaaagggg gtgtggaaag agcaggcttc    2280
caggagagag gcccccaaac cctctggccg ggtaataggc ctgggtccca ctcacccatg    2340
ccggcagctg tcaccatgtg atttattctt ggatacctgg aggggggcca atggggcct    2400
caggggagg ccccctctgg aaatgtggtt cccaggatg  ggcctgtaca tagaagccac    2460
cggatggcac ttccccaccg gatggacagt tattttgttg ataagtaacc ctgtaatttt    2520
ccaaggaaaa taaagaacag actaactagt gtctttcacc ctgaaaaaaa aaaaaaa     2577

<210> SEQ ID NO 3
<211> LENGTH: 23000
<212> TYPE: DNA
<213> ORGANISM: Homo sapiens

<400> SEQUENCE: 3
tccttttgcc atgatatgca ttataatgca atgaatgtgt gcacatgctt cctcctgtat      60
gtgtgcgagt gcaccttgga taaatctcta caagcacctg gctcactgga cctgtaggtt     120
tgattttgag agatattaga gaggttgttt tctgcaacgt gccaggaagg cgctggttac     180
aacctcggcc actcagcgtg ttcacggact atctaggccg ccccctgag  gagctgtctg     240
gaactgcatc tacacgcaac aaggatttgg ggtagcgggg taactccaac gtagccctac     300
acgtgattcc ttccagaccc tgagccagga cgttcaatct ttcaaattca ccctggaggc     360
tccaggggcc tagagtttcc atttattatt cacttacatg gcgaaatccc atctatcttt     420
ttttttttc  ttttccttc  gagacgtagt ctcgcgctgt tgctcaggct ggagtgcaat     480
ggcaggattt cggctcactg caaccttcac ttacccacca ccacacccgg ttaatttttt     540
gtatttagta gagacggcgg tctcaccata ttggtcaggc cggtctcgaa ctcctaacct     600
caggtgatcc accgtcttg  gcctaccaaa gtgctaggat tacaagcatg agccactgcg     660
cctggcctct ctatctttta aaataatta  taatttggat gaaatttaga tgaattcttt     720
tttttctttt ttttttttt  tttttgaga  cagagtctca ctctgttgca caggctggag     780
tgtggtggcg cgatctctgc tcactgcaac ctctgcctcc cgggttcaag caattctctg     840
cctcagcctc ccgagtagct ggggattaca ggcgcccgcc accacgcccg gttaattttt     900
gtatttttag tagagatggg ggtttcacca tgttggccag gctggtcttg aactcctgat     960
ctcgtgatcc acccacctcg gctcccaaag tgctgggatt acagatgtga gccaccgcac    1020
ccagcctaga tgaattcttt aaaataaact tacatacatt tatttaaaag ttaacgttac    1080
atgataaacg gtgtgcatga caaatcagta tccccagtca tgaaaaatag caatggtttc    1140
```

```
tgtctcttgg gagccagcat tcgcatttaa tattttatt ttttatttac ttatttattt    1200
ttttgagtca gagcctcgct ctgtggcgca ggctggagtg cagtgcggtg atcttggctc    1260
actgcacgct ccgcctcccg ggttcacgcc attctcctgc ctcagcctcc tgtgtacctg    1320
ggactacagg cgcccgccac cacgcccggc taatttttg tattttagt agagacgggg    1380
ttttatcatg ttagccagga tggtctcgat ctcccgacct cgtgatccgc ctgcctcggc    1440
ctcccaaaat gctgggatta caggtgtgag tcaccgcgcc cggccccgca tttagtctta    1500
atgataatct ggtaggtagg tgctattata ttattacttt ttatagagag gaaactgaac    1560
catagagaac taagtaagcg cccacgggca ctgagctggt aagaggcaga tccagggttt    1620
gaaccccca aagacgggtg ccacacgcct cttgatagga agtaaatcaa aaataaagac    1680
aaggaaggcc gggcgcggtg gctcacgcct gtaatcccaa cactttggga ggccgaggcg    1740
ggcggatcat gaggtcaggg gtttgagacc atcctggcca acatggtgaa accccatctg    1800
tactaaaaat acaaaaaatt agctgggtat gatggcgggc gcctgtaatc ccagctactc    1860
gggaggctga ggcagaattt tttgaacccg ggaggcggag gttgcagtga gccaagatcg    1920
agctactgca ctccagccca ggtgacagtg agagactctg tctcaattaa aaaaaaaaa    1980
aaaaaaaaa gacaaggaaa acctgaggcc tgggcacagc gcctcacacc tataatccca    2040
gaactttggg aggccaatgg agtcaggatc tcttaaaccc aggtgttcaa gaccagcctg    2100
ggcaacattg cgagacccca tctctacaga aaaacaaaca aacaaacaaa aactaaaaat    2160
tagccgggtg tggtggcgcc tgtctgtggt cccagctact caggaggctg aggtgggagg    2220
atcgcttgag gccaggagct caaggctgca gtgagccgcg attgcgccac tgcactccag    2280
cctgggcgtg cagatcagag cgagaccttg tctctaaagg aaaaaaaaaa agaaagaaag    2340
aaagaaaaga aagaaaaga aacctagcg aggtagataa ttttccctag atcctgcggc    2400
cgccggacca cgaggccggc gctgtgcgtt gttaaaagga gaatagcaga tggtggcgcg    2460
cagccccgcg aggagacatc cagcaacgaa atcgggagat ggaagggaca gtgagaaggg    2520
gggcctggct gtgcgccccc gcccgatgcc ccactcctcg ccgacgggcg ccgggcacct    2580
gcgggaaggg cgggagaatc gccgctcctt tcccgccgcg ccctttccgc cctctccccg    2640
cctcctttc gggcgtcccg aggccgctcc ccaaccgaca accaagaccc cgcaggccac    2700
gcagccctgg agccgaggcc ccccgacggc ggaggcgccc gcgggtcccc tacagccaag    2760
gtaaggcagg aatctcctgg actgggtcgc ggtccccggg cttccggaa gcgcagtgcg    2820
cgggtggcat cactgtgccc ggagccctg gcgcgcccgg ccatccccac cccgagggac    2880
cccctacgga ggcgacctgg gggctgaggt gagcgcttgg gcagcagcga cggggagggg    2940
tgtccacccc acccctggtg cgggccgggg cgcgcaggcc tggaactcgg ggttcagact    3000
ccccgcgact cggaccacgc ggctaagcgc gctcagggtc gcgtgccccc gccccgccgc    3060
catgctgggc gccgtggtgg ccgcgcagct gggcgacagc aggcgtgggc gggggtgggg    3120
agcggcccct cagcggtccc taccgcctga ggccagggcc cggggacttt tattgtgaca    3180
cggcgggcgc ccggctctgc ttagtcatgg tgacctgcgc gcgctccgcg cctcccccac    3240
gcgcagcgat ggaggcgccg gggctcgggc ggtggaggcg gagccggagc gcggccatgg    3300
cggggtgagt gaggcgggat gtgcccgggc tgcgggcatc gcgggccgcg agcgcccctg    3360
cggccgtgcc cggagaccag gaaaacgggc gccacgcccc agggcgcctc cgagttcccc    3420
gccaggactc ggagggccag gagggcgcga cctgggtgga tattttgtt ggacggcgca    3480
```

```
actcttgggg tggcccggga gcggcggaaa ccgagcgaga gaaccaggag gcgctgcgca    3540
gaaggaggcc cggggctcc gaggcgttga ggggctcgat ctgcgttctg ggttggcag     3600
ccgagaggcc gcggtggggt cacttcctcg cctcactggg cctggtggag gctcaggagg    3660
ggcatgcgca gtcgcccact tgccgctttg tagggtgggg gaagtgcccg gtgcccaagg    3720
ggcattgttg accgattggc caaagaccaa gaggcaaacc cagggccttg gcaccagagt    3780
gggggccgag tggcacccag ggagggtgga ggaggccgct ctggcaggca cggtggcagg    3840
gcagttagcc aaccacccgt ttattgaccc ctgcgcagtg ccaggcccca ggcgagaggc    3900
acaggagagg gttggcccga cgccgaccta cataggtctc cctgccattt gaggcgctgg    3960
ggccggggac gagagacagt cgatcaacag acaagcaaag gaggtcattt cagttcctga    4020
caagcgcagt gatgacaata aaacagggaa gaggagactt tgagttgagt cccagaaaga    4080
ggggagtgag aacttgcaga tccacttgtg gggagccact tggagatccc ccactccttt    4140
tgaaacgtaa ctcacgtctg ggcacagcag cctatgcctg taatcccagc attttgggag    4200
gtcgaggagg gggatcactt gaggccagga ggttgagacc accctggcca acatggtgaa    4260
atcccatctc tactaaaaat acaaaaaatt agcccatcgt ggtggctggt gcctgtaatc    4320
ccagctactc aggaggccga agtatgagaa tatctttttt ttgttttatt tgagatggag    4380
tcttgttctg tcacccaggc tggaatgcag tggtgcgatc tcggctcact gcaagctctg    4440
cttcctgggt tcacgccttt ctcccgcctc agcctcccat gtagctggga ctacaggcgc    4500
ccgccgccac acccggctaa tttttttgta tttttagtag agatggggtt tcaccatgtt    4560
agccaggatg gtctcgatct tctgaccttg tgatccgcct gcctcggcct cccaaagtgc    4620
tgggattaca ggcgtgagcc accacgcccg gtcgagaata tcttgaactc gggaggcaga    4680
ggttgcagtg agccaagatc gcaccactgt actccagcct gggcaacaga gcgagactct    4740
gtctcgaaaa acaaaacaca aaacacataa ctcatctcct ggccctccag gatccagggg    4800
tttccatgaa acccttcctt aagtccttag ctctcactgc actccttccc aattctccag    4860
attgactgtc tcagcctctg agccactgca cttactgttt cctctgcctg gaaaactact    4920
ccccagcctc ccactttata ataattttca tccttgtctc agctccaacc tcaccttctc    4980
aaagaggctt ggtctgccag atttttaaaaa actgcacccc gggtcaggca tggtggctta    5040
cgcctgtaat cccagcactt cgggatgcca aggcgggcgg ctcacttgag gtcaggagtt    5100
tgagaccagc ctggccaaca tggcgaaacc cagtctctgc taaaaataca aaaactagcc    5160
gggtgtggtg gcgacgcct gtagtcccag ctactcggga ggctgaggca ggaggatcgc    5220
ttgaacccgg gaggcggagg ttgcagtgag ccaagatcga gccattgcac tccagcctgg    5280
gtgacagaga gactccatct gaaaaaaaaa aaaaaaaaag caaacaaact gcacccgatt    5340
ctcacgttgt cacaatgctg ttgtaatttt cttcatgaag ctgttttttcc aggtcttgct    5400
tatttagtt tatgattgct cctccctgca gttgtcagct ctggcagggt aggattttg     5460
tattttgctc actgctgtgt cttcagcacc cagatcagtg cctggcatac agtaggtgcc    5520
cagtaaatgg tgaggcaaat gaaggaatga gctcaacatg ctctagaaag ggaaaggccg    5580
ccagattgct gaagcagagt gatcaaaggg aagaggtggc aggggctaat tgcgtagggc    5640
tttgcaggct gttgaggagt tcagttttac taggtactgt gggaggcatt ggaggatcca    5700
gagcagggga gagacatgac ttcatgtatg ttttaagatg ggctcttggg ccaatcaggt    5760
tgatcaggtc ggggaagttt gcaagtttgc aaatggattc tgcttcacct actttgcagg    5820
aaaactgacc taggaattgc tttatcttgc aaaacgaggc ccggcaggtg ctggcccagt    5880
```

```
cccaacccct gccctctgcc ctgtgctctc tccctccag gtccctgagt gccagaggtg    5940
gtggtgttgc ttatcttctg gaaccccatg cagccagatc ccaggcctag cggggctggg    6000
gcctgctgcc gattcctgcc cctgcagtca cagtgccctg aggggcagg ggacgcggtg    6060
atgtacgcct ccactgagtg caaggcggag gtgacgccct cccagcatgg caaccgcacc    6120
ttcagctaca ccctggagga tcataccaag caggcctttg gcatcatgaa cgagctgcgg    6180
ctcagccagc agctgtgtga cgtcacactg caggtcaagt accaggatgc accggccgcc    6240
cagttcatgg cccacaaggt ggtgctggcc tcatccagcc ctgtcttcaa ggccatgttc    6300
accaacgggc tgcgggagca gggcatggag gtggtgtcca ttgagggtat ccaccccaag    6360
gtcatggagc gcctcattga attcgcctac acggcctcca tctccatggg cgagaagtgt    6420
gtcctccacg tcatgaacgg tgctgtcatg taccagatcg acagcgttgt ccgtgcctgc    6480
agtgacttcc tggtgcagca gctggacccc agcaatgcca tcggcatcgc caacttcgct    6540
gagcagattg gctgtgtgga gttgcaccag cgtgcccggg agtacatcta catgcatttt    6600
ggggaggtga gcggggaagt ggggctgggg gcagtgtcag gagaaggacc agggatggac    6660
gagtgctcat cactgtctcc ccttgagatg tcaaggcagg aaactggaga aaaggaggt    6720
tctgggctgg gtatggtggt gtagtctcca cagtttgagg ggctgaggcg ggggattgc    6780
ttcaggccaa gagttcaaga ccagcccagg caacataatg acaccctgtc tctaaacaaa    6840
caaacacaca aacaaaaaac aactgggggcc gggcgtggtg gctcatgcct gtaatcccaa    6900
cactttggga ggccgaggca ggtggatcac ctgaggtaag gagttcaaga ccagcctggc    6960
ccacatagct aaaacccatc tctactaaaa atataaaaat tagccaggcc tggtggcggg    7020
cgcctgtagt cccagctgct caggaggctg aggcaggaga atcgcttgaa ccaagaggtg    7080
gaggttgcag tgagtggaga tcgagccact gcactccagc ttgcgcaaca gagcaagact    7140
cagtttcaaa aaaaaaaaaa attaaaaaac aactgggggtt ctgagttcct tgtctacaca    7200
tgtggggaga ctggtgaaca gctggggaag gtgaggtctt catatgtctc tgggctccct    7260
ggtttctctg gggtcaaagt ggggcagagt gcagtgaaca gcagccaaat cctagggtag    7320
cccagccttt cgggcagtca gcaaatgttt attggacacc cgtgacaggc tgcaagctgt    7380
aagtctgaac cttagtcatg ttttctttgg tccacacaat gtccttatac tgttttggt    7440
ttcgttttca catttctcag tgaaggaaat tatctataga aattgacaag agagggcagg    7500
gcccagtggc tcacgcctgt aatcccagca ctttgggagg ctgaggcggg tggctcacct    7560
gaggtcagga gtttgagacc agcctgacca atatggtgaa accccatctc taataaaaat    7620
acaaaaaaag aaaactagcc gggtgtagtg gcatgtgact atagtccctg ctactcgaga    7680
ggctgagaca ggagaatcgc ttgaaccggg gaggtggagg ttgcagtgag ccgagatcgc    7740
accattgcac tccagcctgg gcgacagagc aagactctgt ctcaaaaaaa aaaaaaaaa    7800
agcctgggcg cggtggctca tgcctataat cccagcactt ggaaggcca aggtgggcag    7860
atcacctgcg gtcgggagtt caagaccagc ctgaccaaca tggagaaacc acgtctctat    7920
taaaaatgca aaattagcct ggcatggtgg ctcatgcttg taatcccagc tactcaggag    7980
gctgaggcag gagaatcgct tgaacccggg aggcggaggt tgcagtgagc tgagattgcg    8040
ccattgcact ccagcctggg caataagagc gaaactctgt ctcaaaaaaa aagaaaaag    8100
tttttgaaga gatgaggtct tgctctgtcc ccaggctgga atacagtggt gccatcatag    8160
ctcactgtag cctccaactc ttgggctcaa ggaggcctcc tatctcagcc tcctgagtag    8220
```

```
ctgggactat aggtatgcag caccacgcat ggctaatttt ttagttttta aatttttttg    8280
tagagacagg gtcttgctat gttgctgaga ctggtctcga acctcctggc tttgaacaat    8340
cctctggctt tggcctcccg tagtgttggg attacaggta tgaagcacca taccaacacc    8400
aggccaagaa gtgtttattg agcacttgct gtgggccagc ccctgttcta agtgatttat    8460
gtcctttgca tcattgactg ttcccaactg tcctatgagg cagtactacc cttcagccta    8520
ggcaagcagg gcagtgcccc aggccctaag ccttcgggag tcccatgtct tggtgttcct    8580
tcctggaaat tttctaagtc ccccactggc tggtaccagc tgggatggat gttacactga    8640
tctctatttc tctccttcag ggatagattc tttcctaccc tctatgttac atgtggggtt    8700
gatcagacgc cccagggttc tctggcgtta gtcctagggc ctgcagcttc taggaaagtg    8760
gtctatacag taggagaaac atatacagtg tttctttctt gtgtttgtat gaacatgggg    8820
tactagatta aaactgatta catagacgag tgcctgacaa cttttttttt ttttttttgag    8880
acggagtctc actctgtcac ccaggctggc atgcagtggc actgtatcgg ctcactgcaa    8940
cctccatctc ctgggttcaa gcaattctcc tgcctcagcc tcccaagtag ctgggattac    9000
aggtgcctac cactatgccc agctaatttt taaaaaatat ttttagtaca gatgggcttt    9060
caccatgttg gccaggctgg tctcgaaccc ctgagctcag gtgatctgcc tgccttggcc    9120
tccctaactg tgctgggatt acaggcatga gacactgcgc ccacgcccgc cccccaccgc    9180
ccagtccttt tttgtttttg agactgagtc tggctctatc gcccaggctg aagtgcagtg    9240
gcaagatttc ggctcactgc aagcctccat gtcctgggtt caagcgattc tcatgcctca    9300
gcctccgaag tagctgggat tacaggggtg caccaccacg ctggctaatt tttgtatttt    9360
tagtagagac agggtttcac catgttggcc aggctggtct ggaactcctt acctcacgtg    9420
atccgcccac ctcagcctcc caaagtgttg ggattacagg cttgagccac cacgccaagc    9480
ccccttttt tttttttggg gggtggggga cagagtctca ctctgtcatc aggctggagt    9540
atagtggcat gatctcggct cactgcaacc tccgcctctc gggttcaagt gattctcatt    9600
cctcagcctc ccaagtagct gggattatag gcatgtgtca ccatgcccag ataattttg    9660
tattttttgt agagatgggg tttcaccatg ttggtcaggc tggtcttgaa ctcctgacct    9720
caagtgatcc gcccgacttg gcatcccaaa gtgctgggat tacgtgtgtg agccaccgca    9780
cctggccttt tttttttttt tttcttttt tagagacagg gtctcactct gtcacccagg    9840
ctggacttca gtggcacgat ctctgcttat cacaaactcc agctcctggg ctcaagtgat    9900
cctcccacct cagtctcctg agtagctgag actacaggcg tgagctacca tgcttggcta    9960
attttttatat cttttcttgg tagagatgag gtctcgctat gttgcccagg ctggtcttaa   10020
actcctgggc tcaagcaatc ttcccgcctt ggtctcccaa agtaccagga ttacaggcgt   10080
gagccaccac acctggctac aagaaatatt tatccagggc tctgtatacc ctagaagtag   10140
ccttactttg aggtggccat taatataatc ccattttaca gaggaggaaa accaagacat   10200
ggagcatttc agagatttgc ccaagttaca cacctacgaa gtggtcggat caaaattcca   10260
actcatgctg gtttcttcgg agcttccact tttttttttt ttggagatgg agtctcactc   10320
tgttgctcag gctggagtac agtggcacaa tctcagctca ctgcaatctc tgcctcctgg   10380
attcaagcga ttttcctgcc tcagcctcct cagtaactgg gattacaggt gcccaccacc   10440
acagctggct aatttttttg tttttagtag agacggggtt tcaccgtgtt ggccaggctg   10500
gtctcggact tctgacctca ggtgatccgc ctgcttggcc tcccaaagt gctgggatta   10560
caggtgggaa ccactgtgct ggcccagagc tgtcacttgt ttttttccac aacattctat   10620
```

```
tgtgattgct tatttttcc tttttagtc tatttgccat tttagaaaat gatttcattt    10680
taaaaaacaa gatgggtgag ttggctcgtg cgtataatct cagtgctttg ggaggctgag    10740
gcaggagaat cacatgagcc caggaatttg aggttacagt ggcacctctg cactccacca    10800
taggtgacag agcaagaccc tgtctcttaa aaaataaact cagacatccc atctctacta    10860
aaaatacaaa aattagccgg gtgtggttgt gcgtgcctgt agtcccagct actcaggagg    10920
ctgaggctga ggcagaagaa tcatttgaac ccggagacag aggttgcagt gagccgagat    10980
cacgccactg tatccagcct gacgacagag tgagactctg tctcaaaaaa aaaaaagaaa    11040
caaaagaggc cgggcgcgtt ggctcacgcc tgtaatccca gcactttggg aggctgaggc    11100
aggcggatca cgaggtcagg agatcgagac catcctagct aacatggtga aaccccgtct    11160
ctactaaaaa tacaaaaaat tagctggata tggtggtggg cacctgtagt cccagctact    11220
cggaggctga ggcaggagaa tcgcatgaac ctggatggca gagcttgcag tgaggcaaga    11280
tcgtgccact gcactccagc ctgggcgaca gagcgagacc ccatctcaaa aaaaaaaaa    11340 aaagaaacaa acagaaaact cagaggccag gcgcggtggc tcaggcctgt aatcccagca    11400
ctttgggagg ccgaggcagg cagatcacct gaggtcagga gttcaagacc agcctggtta    11460
acacggtgaa atcccgtctc tactaaaaat acaaaaacaa aaattagccg ggtgtggtgg    11520
tgggcgcctg tagtcccagc tactcgggag gctgaggcag gagaatggcg tgaacccggg    11580
aggtggagct tgcagtgagc cgagattgca cccctgcact ccagcctggg cgacagagcg    11640
agactccatc tcaaaaaaaa aaaaaaaaaa aaagccaagc caggtatggt gatgcacacc    11700
tgtaatcctc aggaggctga agtaggagaa tcatttgagc tcaagagttt aagaccaacg    11760
gccggacacg gtggctcatg cctgtaatcc cagcactttg gaaggcaagg gggtgggcca    11820
cttgaggtca ggagttccag accaacctgg ccaacatggt gaaaccccgt ctctaccata    11880
aaaatatgaa aattagctgt gcgtggtggc acacacctgt agtcccagcg actcaggagg    11940
ctgaggtggg aagatcgttt gagcccagga gttcaaggct acagtgagct atgattgtgc    12000
cactgcacta cagcctaggt gacagagcaa aactgtgtct caaaagcaaa aacaggccag    12060
gtccggtggc tcacgcctgt aatcctagca cttagggagg ctgagatggg cagatcacct    12120
aaggtcaaga gttcaagact ggccaggcga ggtggctcac gcttgtaatc ccagcacttt    12180
gggaggccga ggcgggcgga tcacgaggtc aggagatcaa gatcatcctg ctaacacag    12240 tcaccccgtc tctactaaaa atacaaaaaa tattagccag gcacggtggt gggcccctgt    12300
agtcccagct actcgggagg ctgaggcagg agaatggcgt gaacccggga ggtggagctt    12360
gcagtgagcc gagatagcgc cactgcagtc cggcctgggc aaaagagcga gactccatct    12420
caaaaaaaaa aaaaaaaaaa aaagagtttg agaccagcct ggccaacatg aagaaatgcc    12480
atctctacta aaaatacata gtgaaactcc gtctctacta aaaataaata caaaaaatg    12540 gccgggcgcg gtggctcacg cctgtaatcc cagcactttg ggaggctaag gcgggtggat    12600
cacaaggtca ggagatcgag accatcctgg ctaacacggt gaaaccccat ctctactaaa    12660
aaaatacaaa aaaacttagc tgggcgtggt cgcgggcgcc tgtagtccca gctaatcggg    12720
aggctgaggc aggagaatgg cgtgaaccca ggaggcggag gttgcagcaa gcggagatcg    12780
ctccactgca ctccagcctg gcgacagag caagactgtc tccaaaaaaa aaaaaaaat    12840 tagctgctct ggaggcacac tcctgtaatc ctagctactt gggaggctga ggcaggagaa    12900
tcacttgaac ctgggtggcg gaggttgcag tgaagcaaga tcacaccact gcactccagc    12960
```

```
ttgggcaaca gagtaagaat ccatatcaaa ataaaataaa ataaaataaa aattaacggg    13020
gcatggtggt aggtgcctgt aatgtcagct acttgagagg ctgaggcagg agaattgctt    13080
gaacctggga ggcagaggtt gcagtgagcc tagatcatgc cactgcactc cagcctgggt    13140
gacagagtga gactctgtct caaaaaccaa agccaaatga taccccaggg tacacgatct    13200
actgagtctt tgcccatttt cctgagtcct gatgacatac ttggcacata gtattaactc    13260
tttttttttt ttcttt gaga cagagtcttg ctctgtcgcc caggctggag tgcagtggcg    13320
caatatcggc tcactgcaac ctccgcctcc cgcctcccgg gttcaagcga ttcttctgct    13380
tcagcctccc gagtagctgg gactagaggc gtgtgccacc acaccc gggt aattttt gta    13440 tttttagtag agatggggtt tcaccatatt ggccaggctt gtctctcaac tcctgacctc    13500
gtgatccgcc agcctcggcc tcccaaagtg ctggcattac aggcgtgagc caccgcgccc    13560
ggcaggatta actcatttag tcatcacaat gtacgcggtt cctattattt gaatccccat    13620
ttagcagata aggaagctga gactgtcagc ggcagtgata agttacttgt cccggtcctg    13680
cttggtgagg tgtgggggtg actggagagt cagcccgtcc cactgtcgcc ctctgcaggt    13740
ggccaagcaa gaggagttct tcaacctgtc ccactgccaa ctggtgaccc tcatcagccg    13800
ggacgacctg aacgtgcgct gcgagtccga ggtcttccac gcctgcatca actgggtcaa    13860
gtacgactgc gaacagcgac ggttctacgt ccaggcgctg ctgcgggccg tgcgctgcca    13920
ctcgttgacg ccgaacttcc tgcagatgca gctgcagaag tgcgagatcc tgcagtccga    13980
ctcccgctgc aaggactacc tggtcaagat cttcgaggag ctcaccctgc acaagcccac    14040
gcaggtgatg ccctgccggg cgcccaaggt gggccgcctg atctacaccg cgggcggcta    14100
cttccgacag tcgctcagct acctggaggc ttacaacccc agtgacggca cctggctccg    14160
gttggcggac ctgcaggtgc cgcggagcgg cctggccggc tgcgtggtgg gcgggctgtt    14220
gtacgccgtg ggcggcagga acaactcgcc cgacggcaac accgactcca cgccctgga    14280 ctgttacaac cccatgacca atcagtggtc gccctgcgcc cccatgagcg tgccccgtaa    14340
ccgcatcggg gtgggggtca tcgatggcca catctatgcc gtcggcggct cccacggctg    14400
catccaccac aacagtgtgg agaggtgagt ggcagggcct gggggtgggc tcggagggtc    14460
ctgctcctgg caagtcccaa gacactgaga tccgggtatt cttcctgagg ctgtttcctc    14520
ttcctgtctt cagggagtgg aggcctcagg atgaagctaa gctccttgga gagttctagt    14580
cagtgacctt tgattctgtg cctgggggctg ggaaatgctt agg ggactgt cacaaaccca    14640 tatggttcct ttgtgcggag ttggaaaatg ttccatcagt ttgaaattgt tgggctaggc    14700
actgtggccc ataactataa tcagggactt tgggaggctg aggtgggagg attgcttgag    14760
tccaggagac tagcctgggc aatagagtaa gaccctgtct ctcttgctct gttgcccagg    14820
ctggagtgca tcttgggtca ctgcaacctc gcctcccagg ttcaagtgat tctcctgcct    14880
cagaccctgg ggtagctggg actacaagta cccaccacca cgcctggtta atttttgtat    14940 ttttt gtaga gatggggttt caccatgttg gccaggctgg tcttgaactc ctgtcctcaa    15000
gggattctcc cacctcaacc tcccaaagtg ctgcgattac aggtgtgagc cactgtgccg    15060
gacctaaagg actctttgag catcaaagag tgatgctgaa tgtgtgattt ctcctttctg    15120
agatgttatc ttgttatctg tgaagtgggg gatctggctg agccactagg ggtttatcag    15180
atgtgttttt gaacttgagc aattgatggc taggaggctc agttttgtca tttggaaaat    15240
ggagttgcta atacctcaat ccttggagaa caactgcaag cactagagtt cgagtggagg    15300
tgggcacggt ggtgtgcacc tgtagtccca gctactcagg aggctgagcc aggagggttc    15360
```

```
cttgagccca agagttgata gctgcaggct gggtgtggtg gctcatgcct ataatcccag   15420
ccctttggaa agctgaggca ggcagatcac ttgaggtcag gtgtttgaga ccagcctggc   15480
caacatggcg aaacccaatt tctactaaaa atacaaaaat tagccgggcg tggtggtggg   15540
tgcctgttat cccagctact tgtgaggctg aggctgaata actgcttgaa cccaggaggt   15600
ggaggttgca gtgagccatg ctctcaccat tgcactccat ctcaaaaaaa aaaaaaaaaa   15660
aaaagtttga agcttcagtg attgcaccac tgcactccag cctggacaac ggagcaagac   15720
cctgtctctt ttttctttt tttttttttg agatggagtc tcgctctgtt gcccaggttg   15780
gagtgcagtg gcatgatctc agctcgctgc aacctccgcc tcccaggttc aagtgattat   15840
ctcgcctcag cctcccgagt agctgggatt acaggcatct gccatcacac ccagctaatt   15900
tttgtacttt tagtagagac aggttttac catgttggcc aggctggtct caaactcctg   15960
agctcaggtg atccgccctc ctcggcctcc caaagtgctg ggattacagg catgagccat   16020
cgcgccggat gaacctgtct ctttaagggg gaaaaaaaaa aggaaaaaaa agagtatctg   16080
gcccttaagt attccacgaa ggtcagctat aatggccatt gtccccattt ttcttacgcc   16140
cttgcaggta tgagccagag cgggatgagt ggcacttggt ggcccaatg ctgacacgaa   16200 ggatcggggt gggcgtggct gtcctcaatc gtctcctta tgccgtgggg ggctttgacg   16260
ggacaaaccg ccttaattca gctgagtgtt actacccaga gaggaacgag tggcgaatga   16320
tcacagcaat gaacaccatc cgaagcgggg caggtgggtg gggacggtag ggaggggagc   16380
acccaggaac accccctacc atcctggggt gaaactgagc caggcctggg agagaccccc   16440
tgttgcaacc ctcatgctgg ggtaaccaca gaagccctgg attctgatag agtccaagct   16500
tctctctctc cccgcttcat ttctgagggt gagaagggag aggagagagg aaaggtctcc   16560
ctcaaggagg tgatggctgg ggttcccaaa gccagacccc cagagtcacc ttctctgcat   16620
ggtgcccttt aggcgtctgc gtcctgcaca actgtatcta tgctgctggg ggctatgatg   16680
gtcaggacca gctgaacagc gtggagcgct acgatgtgga aacagagacg tggactttcg   16740
tagcccccat gaagcaccgg cgaagtgccc tggggatcac tgtccaccag gggagaatct   16800
acgtccttgg tgaggccctg ggggcgggga agagtcctga ctagcccatc ttttgtggac   16860
tgcttttgct tttgctttcc tttttttttt tttttttttt ttttttagaa acaaggtctc   16920
gctctgttgc ccagctggag tgcagtggtg tgatcacagc tcgctggagc ctcaacagcc   16980
tgggctccag ccatcctcct gcctcagcct cccaagtagc agggaccaca ggcgcgcacc   17040
accacacccg gctaatgttt ttttctttt gagatggtgt ctcacagtgt tgcccaggct   17100
ggagtgcaat ggcatgatct cagctcactg caacctccac ctcctgggtt caagcgattc   17160
tcctgtctca gcctcctgag tagctgcgac tacaggcaca tgccaccaca ccaggctaat   17220 ttttgtatt ttagtagaga cagggtttca ccatgttggc caggatggtc tcgaactcct   17280
gacctcgtga tccacctgcc tcggcctccc aaagtgctag gattagaggc atgagccacc   17340
gcgcccggcc tgttttgttt tttgttttgt tttgttttgt tttgttttt gagacagagt   17400 ctcagtctgt tgccaggctg gagtgcaatg gcacgatctc agctcactgc aacctccgcc   17460
tcctggtttc aagtgattct cccccatcag cctcccaagt agctgagatt acaggcgcct   17520
gccactatgc ccagctaatt tttgtatttt agtagagatg gggtttcacc atgttggtca   17580
ggctggtctt gaacgcctga cctcaggtga tctgcccacc tcagcctccc aaagtgctgg   17640
gattacaggt gtgagccacc gcgcccagct taatgttttt gtttattttt atttatttt   17700
```

```
attttattt   tttgagacag   agttttgctc   atgttgccca   ggctggagtg   caatggcgca   17760
atcttggctc   actgcaacct   ctgcttccca   ggttcaagtg   attctcctgt   ctcagcctcc   17820
tgagtagctg   ggaatacagg   cacgtgccac   cacgcctagc   taattttttt   ttgagatgga   17880
gttcacttt    cgttgcccat   gctggagtgc   aatggctcga   tctcggctca   ctgcaacctc   17940
cacctggcag   gttcaagcga   ttttcctccc   tcagcctccc   gagtagctga   ggttacaggc   18000
atgcgccacc   acgcccggct   aattttgtat   ttttagtaga   gaagggtttt   ctccatgttg   18060
gtcaggctgg   tctcgaactc   ctgacctcag   gtgatctgcc   cgcctcggcc   tcccagaggg   18120
atgggattac   aggtgtgagc   caccatgccc   ggccaatttt   gattttagt   agagacgggg   18180
tttcacaatg   ttagccaggc   tggtcttgaa   ctcctgacct   caggtgatcc   acctgcctca   18240
gcctccgaaa   gtcctgggat   tacaggcatg   agccactgtg   cccggccttt   attttatttt   18300
attttatt    ttttatttt   tgtttattta   tttatttatt   tattttgagg   tggagtcttg   18360
ctctgtcacc   aggctggagt   gcagtggcac   aatctcagct   cactgcaacc   tccgcctccc   18420
gggttcaagc   gattctccta   cctcagtctc   ccaggtagct   gagattacag   gcgtgcatca   18480
ccaatcgcat   ctaattttgt   attttagta   gatacagggt   ttcactctgt   tggcgaggct   18540
ggcctcgaac   tcctgatctc   aggtgatctg   cccgcctcgg   cctcccaaag   tgctgggatt   18600
gcaggcatga   gccaccgcga   gtggcctatt   ttcctatttt   tatttattta   ttttgagata   18660
gggtctcact   ctgttgccta   ggctagagta   cagtggtgca   gcctctgctc   actgcaacct   18720
ctgcctccca   gactcaactg   atcctcccca   cctcagcctc   cctaatagct   aggactacag   18780
gcgcgcacca   ccaagcctgg   ctaaattttt   atgttttttt   gtagagatgg   ggcttcacca   18840
tgttgcccag   gctggtctca   aactcctgga   ctcaagtgat   ccacccacct   cagtctccca   18900
aagtgctggg   attataggcg   tgagctacca   agcctggcca   tttttttttt   tttttttt    18960
ttttagtaag   agactaaggt   tttgctatgt   tgcccaggct   ggcttcgaac   tcctggcctc   19020
aagcaatcct   cctgcctcag   ccctgcaaag   tgctaggatt   ataggcgtga   gccaccacgc   19080
ccggcctgct   tttgcatctc   acagctgcat   ctctctcttt   ctgtcccctg   ctcttggatg   19140
tggtgtgaca   ggtggtgacc   atcccttctg   ttcttcccgc   aggaggctat   gatggtcaca   19200
cgttcctgga   cagtgtggag   tgttacgacc   cagatacaga   cacctggagc   gaggtgaccc   19260
gaatgacatc   gggccggagt   ggggtgggcg   tggctgtcac   catggagccc   tgccggaagc   19320
agattgacca   gcagaactgt   acctgttgag   gcacttttgt   ttcttgggca   aaaatacagt   19380
ccaatgggga   gtatcattgt   ttttgtacaa   aaaccgggac   taaaagaaaa   gacagcactg   19440
caaataaccc   atcttccggg   aagggaggcc   aggatgcctc   agtgttaaaa   tgacatctca   19500
aaagaagtcc   aaagcgggaa   tcatgtgccc   ctcagcggag   ccccgggagt   gtccaagaca   19560
gcctggctgg   gaaaggggt   gtggaaagag   caggcttcca   ggagagaggc   ccccaaaccc   19620
tctggccggg   taataggcct   gggtcccact   cacccatgcc   ggcagctgtc   accatgtgat   19680
ttattcttgg   atacctggga   gggggccaat   ggggcctca   ggggaggcc   ccctctggaa   19740
atgtggttcc   cagggatggg   cctgtacata   gaagccaccg   gatggcactt   ccccaccgga   19800
tggacagtta   ttttgttgat   aagtaaccct   gtaattttcc   aaggaaaata   agaacagac   19860
taactagtgt   ctttcaccct   ggctctgggc   tggaggcctg   aaaccggggg   ccagaaaggg   19920
ctcttcttct   gaaacacact   cctctttgac   ttagggctgg   tatttgaaac   cagtttgtaa   19980
tctttgccca   tcgcatttt   atatgtaggg   catcttctc   cccgtaggca   agccacacag   20040
ttgtccttca   gtttcagctg   ccttggaaga   caagcagcta   attcctagtc   acatctccta   20100
```

```
gggctcccca aggtcatttt ttttttttt tgagatggag ttttgccctt gtggcccagg    20160
ctgaagtgcg atggcgggat ctcagctcac tgcgacctct gcctcctagg ttcaagtgat    20220
tctcctgcct cagcctcccg agtagctggg attacaggca tgtgccacca cgcctggcta    20280
gttttgtatt tcagtaggat ttctccatgt tggtgaggct gatctcaact cctgacctca    20340
ggtgatccgc ccacctcggc ctcccaaagt gctgggatta caggcgtgag ccaccatgcc    20400
cggcctactt ttttttttca agacggagtt ttgcaacctc ctcctccagg gttcaagcga    20460
ttctcctgcc tcagcctctc gagtctctag gattacagct gcgcaccacc acacccagct    20520
aatttttgta tttttagtag aaacagtgtt tcaccatatt ggccaggctg gtctcgaact    20580
cctgacctca agtgatccac ccaccttggc ctcccacagt gctgggatta taggcatgag    20640
ccaccacgtg cagcctggta aatttagaca caaccaaagg tatcacccct ttccttcctc    20700
aatagttctt ctcttttcaag ttttttcttt ttttttcccag agacaaggtc ttgctctgtt    20760
gccccggctg aagtggaggg atagtagctc acttcagcgt tgaattcctg ggctcaagtg    20820
atcctcccac ctcagcctcc tcagtaactg ggactacaga catgtgccac tatgcccagc    20880 taattttttgt atttttttata gaaatgaggt tttgccttat tgcccaggct ggtcttgaac    20940
tcctgggctc aagggatccc ctgactcggc ctcccaaagt gctgggatta caggtgtgtg    21000
tcaccttgcc ttgtaatgta gtattattta cttaggaatg agttaagtac tggaaacctg    21060
aaatgctgaa attgggcaga attgtcaaga ctgttgacgt tagaatgatc atgataacat    21120
ttcacagcag accactttag ttgtataatt taaaattcat ggctgggcgc agtggctcac    21180
gcctgtaatc ccagctcttt ggaggccgag gacgggcgga tcacaaggtc aggagatcga    21240
gaccatcctg gctaacacgg tgaaaccccg tctctactaa aaatacaaaa aaaaaaaaaa    21300
attagccggg cgcagtggct ggcgcctgta gtcccagcta cttgggagac tgaggcagga    21360
aaatggcgta aacccaggag gcagagcttg cagtgagcca agatcgcgcc actgcacccc    21420
agcctgggct actgagcgag acaccgtctc aaaaaataat aataataaat aaataaatag    21480
ataaaattca taggctgggc caggtgtggt ggctcctgcc tataatccca acagtttggg    21540
aggccaaggt aggtggattg tttaagctca ggagttggga ggccagcctg gacagcgtag    21600
tgtgaccctg tctctactaa aaaatacaaa aattatctgg gggtgctggt gcacgcctgt    21660
aatcccagct actcaggagg ctgaggcacg agaatcactt gaactcgaga ggcagaggtt    21720
gtggtgagcc aagatcgcgc cgctgcactc cagcctgggc agcagagtaa gactctgtct    21780
caaaaataaa aataataaat aagtaaaatt cacaggctgt ccaggtacaa tggctcatgc    21840
cagtaatcac aactctttgg gaggctgagg cgggaggtga cttgagccca ggagtttgag    21900
gctgcactga gctatgactg caccactgca ctctagcctg ggtgacacag caatacccct    21960
gactctaaaa taaaataagg ctgggtgtgg tggctcacgc ctgtaatccc agcactttgg    22020
gaggctgagg caggcggatc acctgaggtc aggagttcaa gaccagcctg gccaacatgg    22080
tgaaacactg tctctactaa aaatacaaaa attagctgcc cgtggtggca tgtgcctgta    22140
atcccagcta ctcgggaggc tgaggcagga gaatcgcttg aacccgggag gtatagctct    22200
gggatgaata ccctcaggc agagtcagga agttccatct aaaaggcaga cagcaccctc    22260
ttgtgggcct ctgggtgaaa gaggcccaga gaaagaaagt tagaaaagga actatttcca    22320
gagaaagaaa gttagaaaag gaacaagatt ggatgagctc ctggcttgtt cctattttta    22380
aaagtagcat tctccgggcc aggtgggtg gctcacgcct gtaatcgcag caatttggga    22440
```

| | | | |
|---|---|---|---|
| ggcccagatg | ggtagatcac | ctaagctcgg gagttctaga ctagcctgac taacatggag | 22500 |
| aaaccctgtc | tctactaaaa | atacaaaatt agccgggcgt ggtggcacat gcctgtaatc | 22560 |
| ctagctactc | gggaggctga | ggaaggagaa ccgcttgaac ccgggaggtg gaggttgtgg | 22620 |
| taagccgaga | tcttaaccac | tgcactccag catgggcaac aagagcaaac atctgtttca | 22680 |
| ttcttcaaaa | ctttggacca | aatgatattt cttataaatc aaataaaagt gcacatgctt | 22740 |
| tgagggagtt | ccctatttaa | aggactcgcc ctcctgcaag caccagcacc ctatccactg | 22800 |
| ctcagggttg | taactaattt | tatggcgcaa actttttttt tttttttttt gagacagagt | 22860 |
| ctcgctttgt | tgcccaggct | ggagcgcagt ggtgtgatct tggctcactg caacctctgc | 22920 |
| ctcctgggtt | cgagcgattc | tcctgcctca gccttccaag tagctgggac tacaggcatg | 22980 |
| tgccaccatg | tcccgctaat | | 23000 |

<210> SEQ ID NO 4
<211> LENGTH: 3434
<212> TYPE: DNA
<213> ORGANISM: Mus musculus

<400> SEQUENCE: 4

| | | | |
|---|---|---|---|
| agacccacgc | cctgctccct | ccgcccggca cctgcaggaa gggctggaac tgcctctgcg | 60 |
| tacccgccgc | ccgtttccgc | cctcccgctc ctcccacgcg tgccgccggg accccgcag | 120 |
| caccgctgcc | ccgatccgag | ccctccaccc ccactccggt cccctcctc tcttcccgga | 180 |
| agcgcggcgc | gtggcggccc | ggcggcgcgg attggacgcg tggcacctac agagacaccc | 240 |
| gggggggtgg | gacggaggtg | agcgagcgcc cgcggaggat gcgtggggga gccagctccg | 300 |
| ggagctgccc | gcggtcgcgc | gtggggccgt gcacgcggtg gggggaagcg cgtgcccttc | 360 |
| tccaagcgcg | caccccgccg | ccgagcccgt gagccctcgt aggtggtgg ccgcggcgag | 420 |
| tagaggtagg | ggtcgcccgc | ggccggcgcc ccgggactct tattgtgaca gggtggcgcg | 480 |
| ctgtgcttag | tcaccgtgac | ccgcgcgcg gaggcggagg cagagcgcgg ccatggcggg | 540 |
| gcccctaacg | gctagcagag | gaactgtgtc ttgtcatcag gaaccccatg cagcccgaac | 600 |
| ccaagcttag | cggggctccc | cgcagcagcc agttcctgcc cctgtggtca agtgccccg | 660 |
| agggggccgg | ggacgcagtg | atgtatgcct ccacggagtg caaggcagag gtgacgccct | 720 |
| cgcaggacgg | taaccgaacc | ttcagctaca cactagagga tcacaccaag caggcttttg | 780 |
| gcgtcatgaa | cgagcttcgc | ctgagccagc aactctgtga cgtgaccctg caggtcaaat | 840 |
| atgaggacat | cccagctgcc | caattcatgg ctcacaaagt ggtgctggcc tcctccagcc | 900 |
| cagtctttaa | agccatgttc | accaacgggc ttcgggagca gggcatggag gtggtgtcca | 960 |
| tcgaaggcat | ccaccctaag | gtcatggaaa ggcttattga gttcgcctac acggcctcca | 1020 |
| tctccgtggg | cgagaagtgt | gtcctgcacg tgatgaacgg ggcggtcatg taccagattg | 1080 |
| acagcgtggt | tcgagcctgc | agcgacttcc tcgtgcagca gctggacccc agcaacgcca | 1140 |
| ttggcatcgc | caacttcgcg | gagcagatcg gctgcactga actgcaccag cgtgcccggg | 1200 |
| agtatatcta | catgcacttc | ggggaggtgg ccaagcagga ggagttcttc aacctgtcac | 1260 |
| actgccagct | ggccacgctc | atcagccggg atgatctgaa cgtacgctgc gagtccgagg | 1320 |
| tgttccacgc | gtgcatcgac | tgggtcaaat acgactgccc gcagcggcgc ttctacgtgc | 1380 |
| aggcactgct | gcgggccgtg | cgctgccatg cgctcacgcc gcgcttcctg cagacgcagc | 1440 |
| tgcagaaagtg | tgagatcctg | caggccgacg cgcgctgcaa ggactacctg gtgcagatat | 1500 |
| tccaggagct | cacgctgcac | aagcccacgc aggcagtgcc ctgccgcgcg cccaaagtgg | 1560 |

```
gccgcctcat ctacacagcg ggcggttact tccgacagtc gctcagctac ctggaggcct    1620
acaacccgag caatggctcc tggctgcgcc tggccgatct acaggtgccg cgcagtgggc    1680
tggcaggctg cgtggtgggt gggctgctat acgctgtggg cggccgcaac aactctccgg    1740
atggcaacac tgactccagc gccctggact gctacaaccc catgaccaac cagtggtcgc    1800
cctgtgcctc tatgagcgtg ccacgcaacc gcatcggggt gggggtcata gatggccaca    1860
tctacgcagt cggggttcc cacgctgca tccaccacag cagcgtggag agatatgagc      1920
cagagcggga cgagtggcat ctagtcgcgc caatgttgac acggaggatt ggcgtgggcg    1980
tggcagtgct caaccgcttg ctgtatgcag tgggggcttt tgacgggact aaccggctta    2040
actccgcaga atgttactat ccagagagga atgagtggcg gatgatcaca ccgatgaata    2100
ccatccggag cggggccggg gtctgcgtgc tgcacaactg tatctatgca caggggct      2160 acgatgggca ggaccagttg aacagtgtgg agcgctacga cgtggagaca gagacctgga    2220
ctttcgtagc ccccatgagg catcaccgta gtgcgctggg gattactgtg caccagggca    2280
agatctacgt cctcggaggc tatgatggcc acactttcct ggacagtgtg aatgctatg    2340 acccggacag tgatacctgg agtgaggtga cccgcatgac atctggccgc agcggggtgg    2400
gtgtggccgt caccatggaa ccctgtcgga agcaaattga tcaacaaaac tgtacctgct    2460
gaagcacttg gaatacctga gcactgacaa caggacagaa aaacagtctg tgtatcactg    2520
cttctctgta ctaaagaaaa aagaagaaaa caaagcataa acagaaaaca cagggccgaa    2580
gaggcggcag aagaagtcat cccttcttcc aggaagggcg actgggatgc cttgtaaagg    2640
accttgtgga agaccagaac tcaaatccat gggcccatct gtcatagccc tggagcgtcc    2700
aagtctggga tggggtatgg gcggggcacc ctcacaggtg agaagccctt gaactcccac    2760
caccagaagg gggggacag gcaaagcagg agatcacatg ttttttttctt tggttcctgc    2820 aactcggtga tcaattccag tggacagggg aagaagggac agctgaggcc aaggggctga    2880
ggctccctct ggaactgggg cccaagggac aagccggcac agagaagcct ctgggctctg    2940
agccctgaac agttatttg ttaaataacc ctgtaagttt cccatgggaa taaagaatgg     3000
agtaggcaca caggtcttca gagggcggtc ggaatccctc agggagagac agctcttcta    3060
ttgaaataca cgcagatcct gatggggctg gtatctgaaa cccgtctatt gtctctgctt    3120
gccattgtac attctgctca gacagggcat cttgcttctt gtgggacaca cagttgtctg    3180
tcagtttcag ggcattagaa gccaatgacc taacttctgt gcctcctaac ttctcctggg    3240
gcctcctgtg tttagcttta ttttgaggca gggactcacg tcgtccggga tggccttcag    3300
ttcagacctt gaactgacgc tgccgcctgt cccagcctac cgagtgctgg gctacatct     3360 gtatagcgca atgcctggtt cctgcttatt attttgtac ccaagcagga aaataaaggt     3420
ttctgggaca ttgg                                                     3434
```

<210> SEQ ID NO 5
<211> LENGTH: 4470
<212> TYPE: DNA
<213> ORGANISM: Mus musculus

<400> SEQUENCE: 5

```
agacccacgc cctgctccct ccgccccggca cctgcaggaa gggctggaac tgcctctgcg      60
tacccgccgc ccgtttccgc cctccccgctc ctcccacgcg tgccgcccgg gaccccgcag     120
caccgctgcc ccgatccgag ccctccaccc ccactccggt cccctcctc tcttcccgga      180
```

```
agcgcggcgc gtggcggccc ggcggcgcgg attggacgcg tggcacctac agagacaccc    240
gggggggtgg gacggaggtg agcgagcgcc cgcggaggat gcgtggggga gccagctccg    300
ggagctgccc gcggtcgcgc gtggggccgt gcacgcggtg gggggaagcg cgtgcccttc    360
tccaagcgcg cacccgccg ccgagcccgt gagccctcgt agggtggtgg ccgcggcgag     420
tagaggtagg ggtcgcccgc ggccggcgcc ccgggactct tattgtgaca gggtggcgcg    480
ctgtgcttag tcaccgtgac ccgcgcggcg gaggcggagg cagagcgcgg ccatggcggg    540
gtgagtgagc cgctccaggc cgcggcccgg gaccaggccc tgcgggctct cccggcgtca    600
gggctgcgcc tccgagcggt ggggaggccg ctggagcagg cgccgggtac cgggcggccg    660
ctgcacagcc ccctgcgcaa tgccaggccc gagctccggc agtgtggtca cgcgtgacag    720
tcgctcacta gctggggccc ctggagcatt tcatccccc cctccccacg gtgatctaat      780
agacaaaaca cgcggagtcg cgactccagg ctgagcccag aacctgggga gccagacgca    840
gaccctctct tgtctcccca catcttcttt gaaagcataa ttcctcccct ggccccaggt    900
ctccaagggt ctcctgaatc cctccccgtg ggtgttccag atgctgcaca ctctcttgcc    960
ccaggagctt ggtgttcgct tagtgtttcc tatacagacc ttgctttatt tttaggcctt   1020
ttctgtcttc tcgctgtgtc tctggagctc agagcagtcc caaatacata aatggcaggc   1080
tctgtaaatg ttggtgtggt gttgaaagga atctgacatg ttggacgaag gcaaggggag   1140
ggaaggatgg ctggaacagt gaagaggttg gaaagcgggt gtggagtttt acaggccatt   1200
gacgatttgg ggtttccatt cttgggctcg gtgaaaggtg ttgggtgatt ctgagcagga   1260
aaaggaacat gatatgccct gaaggcccgc gagttgagaa gttagtttga atggagccgg   1320
ctgtgtccag tttacttggc ttggcaaaat ctgcacttag atatcattgc ttagtcttgc   1380
aaaaaaagaa gcctggctgg acatggtggc acatactgta atcccagcac tcgggaggag   1440
ccagctttgg ttgcatagtg agttggaagc cagcctaggc tatgtaagac cctgtctcaa   1500 ataaataaa ataaagtggc agggtctggt ctaacccagc ctctgttccc agcgctgtgc    1560
tcttccctcc ctccaggccc ctaacggcta gcagaggaac tgtgtcttgt catcaggaac   1620
cccatgcagc ccgaacccaa gcttagcggg gctccccgca gcagccagtt cctgcccctg   1680
tggtcaaagt gccccgaggg ggccggggac gcagtgatgt atgcctccac ggagtgcaag   1740
gcagaggtga cgccctcgca ggacggtaac cgaaccttca gctacacact agaggatcac   1800
accaagcagg cttttggcgt catgaacgag cttcgcctga ccagcaact ctgtgacgtg     1860 accctgcagg tcaaatatga ggacatccca gctgcccaat tcatggctca caaagtggtg   1920
ctggcctcct ccagcccagt cttttaaagcc atgttcacca acgggcttcg ggagcagggc  1980
atggaggtga tgtccatcga aggcatccac cctaaggtca tggaaaggct tattgagttc   2040
gcctacacgg cctccatctc cgtgggcgag aagtgtgtcc tgcacgtgat gaacggggcg   2100
gtcatgtacc agattgacag cgtggttcga gcctgcagcg acttcctcgt gcagcagctg   2160
gaccccagca acgccattgg catcgccaac ttcgcggagc agatcggctg cactgaactg   2220
caccagcgtg cccgggagta tatctacatg cacttcgggg aggtggccaa gcaggaggag   2280
ttcttcaacc tgtcacactg ccagctggcc acgctcatca gccgggatga tctgaacgta   2340
cgctgcgagt ccgaggtgtt ccacgcgtgc atcgactggg tcaaatacga ctgcccgcag   2400
cggcgcttct acgtgcaggc actgctgcgg gccgtgcgct gccatgcgct cacgccgcgc   2460
ttcctgcaga cgcagctgca gaagtgtgag atcctgcagg ccgacgcgcg ctgcaaggac   2520
tacctggtgc agatattcca ggagctcacg ctgcacaagc ccacgcaggc agtgcccgc    2580
```

```
cgcgcgccca aagtgggccg cctcatctac acagcgggcg gttacttccg acagtcgctc    2640
agctacctgg aggcctacaa cccgagcaat ggctcctggc tgcgcctggc cgatctacag    2700
gtgccgcgca gtgggctggc aggctgcgtg gtgggtgggc tgctatacgc tgtgggcggc    2760
cgcaacaact ctccggatgg caacactgac tccagcgccc tggactgcta caaccccatg    2820
accaaccagt ggtcgccctg tgcctctatg agcgtgccac gcaaccgcat cggggtgggg    2880
gtcatagatg gccacatcta cgcagtcggg ggttcccacg gctgcatcca ccacagcagc    2940
gtggagagat atgagccaga gcgggacgag tggcatctag tcgcgccaat gttgacacgg    3000
aggattggcg tgggcgtggc agtgctcaac cgcttgctgt atgcagtggg gggctttgac    3060
gggactaacc ggcttaactc cgcagaatgt tactatccag agaggaatga gtggcggatg    3120
atcacaccga tgaataccat ccggagcggg gccggggtct gcgtgctgca caactgtatc    3180
tatgcagcag ggggctacga tgggcaggac cagttgaaca gtgtggagcg ctacgacgtg    3240
gagacagaga cctggacttt cgtagccccc atgaggcatc accgtagtgc gctggggatt    3300
actgtgcacc agggcaagat ctacgtcctc ggaggctatg atggccacac ttttctggac    3360
agtgtggaat gctatgaccc ggacagtgat acctggagtg aggtgacccg catgacatct    3420
ggccgcagcg gggtgggtgt ggccgtcacc atggaaccct gtcggaagca aattgatcaa    3480
caaaactgta cctgctgaag cacttggaat acctgagcac tgacaacagg acagaaaaac    3540
agtctgtgta tcactgcttc tctgtactaa agaaaaaaga agaaaacaaa gcataaacag    3600
aaaacacagg gccgaagagg cggcagaaga agtcatccct tcttccagga agggcgactg    3660
ggatgccttg taaaggacct tgtggaagac cagaactcaa atccatgggc ccatctgtca    3720
tagccctgga gcgtccaagt ctgggatggg gtatgggcgg ggcaccctca caggtgagaa    3780
gcccttgaac tcccaccacc agaagggggg ggacaggcaa agcaggagat cacatgtttt    3840 tttcttttggt tcctgcaact cggtgatcaa ttccagtgga caggggaaga agggacagct    3900
gaggccaagg ggctgaggct ccctctggaa ctggggccca agggacaagc cggcacagag    3960
aagcctctgg gctctgagcc ctgaacagtt attttgttaa ataaccctgt aagtttccca    4020
tgggaataaa gaatggagta ggcacacagg tcttcagagg gcggtcggaa tccctcaggg    4080
agagacagct cttctattga aatacacgca gatcctgatg gggctggtat ctgaaacccg    4140
tctattgtct ctgcttgcca ttgtacattc tgctcagaca gggcatcttg cttcttgtgg    4200
gacacacagt tgtctgtcag tttcagggca ttagaagcca atgacctaac ttctgtgcct    4260
cctaacttct cctggggcct cctgtgttta gctttatttt gaggcaggga ctcacgtcgt    4320
ccgggatggc cttcagttca gaccttgaac tgacgctgcc gcctgtccca gcctaccgag    4380
tgctggggct acatctgtat agcgcaatgc ctggttcctg cttattattt ttgtacccaa    4440
gcaggaaaat aaaggtttct gggacattgg                                    4470
```

<210> SEQ ID NO 6
<211> LENGTH: 15000
<212> TYPE: DNA
<213> ORGANISM: Mus musculus

<400> SEQUENCE: 6

```
ctgtgccgtg gacaggttcc tggactcaga tggttctgca cgtcgaggct gctcctgtgc      60
actccaggtt cagcatgagc acacacccccg cagcccccac actgagacaa cgcttcttgt     120
acccagactg actttaaata tactacgaag ccaaaaaaac gactttatac ttgtgaattt     180
```

```
tgtttcctgt gagcaaaggt gtgctctgcc acacgtggct tatgctgtgt ggcgacaaaa      240
cccagtccca gccctcaacc tccatttggt agatgaagaa actaacagat ttcccttgcc      300
ccagggtctt agtacggctt taccettggg accccatgc aggaggggct tgcctggtat       360
tcgctgctct tagtctaaga ttcccttgaa gtctctgggt gtgggcgcca ccttgcagta      420
gctctgagaa ttgcctgggt tctgctttta gccgctggtt aaggaacagc gcgtcccttg      480
aggtaattct gggaactgca agcagagtga aagcaggtgg tgaaggggat gcgctcaggt      540
tgggattgcg ggccaacttg cataaaatga attttttccc cagaagttcg cgaaaagcta      600
gcaggggtga ggggtgggga tacagtccgg ctggctccca gagaccctcc ctcagatctc      660
atatctttcc tggtgtgttg gcttggtggt ttaacagtag ggaacttaga gattctgata      720
ttaaatttaa aaagtactca gttccctatt taaataccaa atttaaaaag cactgttggg      780
atttgtagag accttccaga catattctgt gggaaaatga cctgagatgg gttttttggt      840
tgttgttttt tgccattttg attttggaag agggtctcac tatgtaaggc aggctgtacc      900
actttgtagc caaggacgtc cttcactttt ctgatccttc tcctccagct tcctgggtgc      960
tggcattaca agtgtgtccc aatttcagct gtcctgcatt tttgttgttg ttttgtttaa     1020
attattaagt taatagaaca aagtaaggtt ttaccatgca gtccaggctg gcctggaact     1080
tgctatgagc cctggcttgt ctcaaattca cagagatcca cctgtctctg cttcttctaa     1140 aattaaggg atacgacacc atgcctggct ttccttgcct ccctgacccc agacagagtc      1200
tcactgtgta gtctgggctg ttctcaaaca ttcaaccctc tgcttcagac tcccgtggta     1260
aatttctttt gaaactatcc ttttctttga tatttattca tttgttttct gatataaggt     1320
cttgctaggt cgagcaggct tactgtgaac tggaggtaat cctcctgctt cagtgccctg     1380
gtggctggga ttacagatgt gtcccctcaa tattcttatt tttagattta tttccttta     1440 tgtacacgag tactttgctt gcctgtatgt ctgcgcacca cctacctgca tggtgcccac     1500
agaggtcaga agacagcatg gggtcccctt gaactggagc tatggatggc tgtgaggcat     1560
cgtggcagtg gactccaggt cctctgcaaa agcaacacgt gttctaaacc acctttcctg     1620
gttttccgag acagggtttc tctgtgtagc ctggctgtcc tggaactcac tgggtagacc     1680
aggctggcct ctgcctccca agtgctggga ttaaaggcgt gcgccaccac gcctggctta     1740
actttatgtt tcaaagttaa tttatgtgtg tatgtggagg ttatcggaca acaacctgaa     1800
ggaggaagct ttctactact atgtgagtac cagaggtgga acttaggtgg ccagaattgg     1860
ccagacgctc ctttacccac tgagccatct tgatagttca agaaaataac tttctctcat     1920
aaatgccata tgcagcaaat aagtatctct taccattaaa aatatataaa gatgttacga     1980
gaaatacaaa gaggcagctc tgggcattcc aacactccaa cacccctcaga tgaatgccat    2040 acctctcctc atgaaaacat gaacacacag agaggagagt gtgtctctgg agcactcgag     2100
ctgcactttg caggctccac atagggaag agaatcagtt tctgccagcc gtccccgacc      2160
tcaacacaag cacacacaca aattaatgta cacaaagccc agagtgatat cccagccttt     2220
aaccacagca cacgaaggag gcagaggcag aggcaggaag gtttctgtgt gttcaaggcc     2280
agccagggct atgtaatgag gcctgtctca aaagaagtt ataaggctgg agtgatggct      2340
cagcagttaa gagtacttgc tgctcctgca gtggtccagg gttcaattcc cccatttgca     2400
tggtagctaa caaccacctg taactttagg ggacactgca cagcccacgt tgcacagaca     2460
tacatataca ggcaaaacac ccacacgcac aaagtaaaat acaaattgaa ataaaaacat     2520
taaaaagtta ttttacaaga agataaatat cgcaaccagg tagatgggtc tagttggacc     2580
```

```
gtgcaggctg tgggagggtc cgccggtgca ggttcagctg gaggcgtacc ggacagccta   2640
acccggaggc agcctcctag ggccgcccag acccacgccc tgctccctcc gcccggcacc   2700
tgcaggaagg gctggaactg cctctgcgta cccgccgccc gtttccgccc tcccgctcct   2760
cccacgcgtg ccgcccggga ccccgcagca ccgctgcccc gatccgagcc ctccaccccc   2820
actccggtcc ccctcctctc ttcccggaag cgcggcgcgt ggcggcccgg cggcgcggat   2880
tggacgcgtg gcacctacag agacacccgg ggggtgggga cggaggtgag cgagcgcccg   2940
cggaggatgc ggtggggagc cagctccggg agctgcccgc ggtcgcgcgt ggggccgtgc   3000
acgcggtggg gggaagcgcg tgcccttctc caagcgcgca ccccgccgcc gagcccgtga   3060
gccctcgtag ggtggtggcc gcggcgagta gaggtagggg tcgcccgcgg ccggcgcccc   3120
gggactctta ttgtgacagg gtggcgcgct gtgcttagtc accgtgaccc gcgcggcgga   3180
ggcggaggca gagcgcggcc atggcggggt gagtgagccg ctccaggccg cggccgggga   3240
ccaggccctg cgggctctcc cggcgtcagg gctgcgcctc cgagcggtgg ggaggccgct   3300
ggagcaggcg ccgggtaccg ggcggccgct gcacagcccc ctgcgcaatg ccaggcccga   3360
gctccggcag tgtggtcacg cgtgacagtc gctcactagc tggggcccct ggagcatttc   3420 atccccccccc tccccacggt gatctaatag acaaaacacg cggagtcgcg actccaggct   3480
gagcccagaa cctggggagc cagacgcaga ccctctcttg tctccccaca tcttctttga   3540
aagcataatt cctcccctgg ccccaggtct ccaagggtct cctgaatccc tccccgtggg   3600
tgttccagat gctgcacact ctcttgcccc aggagcttgg tgttcgctta gtgtttccta   3660
tacagacctt gctttatttt taggcctttt ctgtcttctc gctgtgtctc tggagctcag   3720
agcagtccca aatacataaa tggcaggctc tgtaaatgtt ggtgtggtgt tgaaaggaat   3780
ctgacatgtt ggacgaaggc aaggggaggg aaggatggct ggaacagtga agaggttgga   3840
aagcgggtgt ggagttttac aggccattga cgatttgggg tttccattct tgggctcggt   3900
gaaaggtgtt gggtgattct gagcaggaaa aggaacatga tatgccctga aggcccgcga   3960
gttgagaagt tagtttgaat ggagccggct gtgtccagtt tacttggctt ggcaaaatct   4020
gcacttagat atcattgctt agtcttgcaa aaaagaagc ctggctggac atggtggcac   4080
atactgtaat cccagcactc gggaggagcc agctttggtt gcatagtgag ttggaagcca   4140
gcctaggcta tgtaagaccc tgtctcaaat aaaataaaat aaagtggcag ggtctggtct   4200
aacccagcct ctgttcccag cgctgtgctc ttccctccct ccaggcccct aacggctagc   4260
agaggaactg tgtcttgtca tcaggaaccc catgcagccc gaacccaagc ttagcggggc   4320
tccccgcagc agccagttcc tgcccctgtg gtcaaagtgc cccgagggggg ccggggacgc   4380 agtgatgtat gcctccacgg agtgcaaggc agaggtgacg ccctcgcagg acggtaaccg   4440
aaccttcagc tacacactag aggatcacac caagcaggct tttggcgtca tgaacgagct   4500
tcgcctgagc cagcaactct gtgacgtgac cctgcaggtc aaatatgagg acatcccagc   4560
tgcccaattc atggctcaca aagtggtgct ggcctcctcc agcccagtct ttaaagccat   4620
gttcaccaac gggcttcggg agcagggcat ggaggtggtg tccatcgaag gcatccaccc   4680
taaggtcatg gaaaggctta ttgagttcgc ctacacggcc tccatctccg tgggcagaaa   4740
gtgtgtcctg cacgtgatga acggggcggt catgtaccag attgacagcg tggttcgagc   4800
ctgcagcgac ttcctcgtgc agcagctgga ccccagcaac gccattggca tcgccaactt   4860
cgcggagcag atcggctgca ctgaactgca ccagcgtgcc cggagtata tctacatgca   4920
```

```
cttcggggag gtgagtgaag ccgggctttg ggctcagaag tgggataggc cagcgtggcg    4980
ttctcccctg cgacaggctg gaggaaaact gttgggtgtt ttcttttttcc ttccttcttt    5040 tctcccatag ggtctcatgt agtccaggct ggccctaatc tggttgggta tctgaggatg    5100
actttaaatt cctgattcct gtctcagtct gtcgagtact gtagttacag acgttcgccc    5160
tcccaatact taatagaatg gaggccagca gtgccccgga acttgatttt acttttgttt    5220 ttaaatctttt tttaaaaaat tatttgcctt tagtttctgt ggattggcgt tttgtctgaa    5280
tgtttgtctg tgtgtgaggt gtcagacctt ggagttacag acagttgtga gctgccatgt    5340
gggtgctggg atttgaactc gagtcttctg gaagaggcca gtagtaccct caactgtgag    5400
cacctgtggt cttatttttt gacagtattc ttcttcttct tcttcttctt cttcttctta    5460
ttattattat tattattatt ttggttttgg tttttcaagg caggatttct ctgtgtagcc    5520
ctggctgtcc tggaactcac tccgtagacc aggctggcct cgaactcaga aattagcctg    5580
cctctgcctc ccaagtgctg ggatgaaagg cgtgcgccac cacacctggc ttgacagtct    5640
tctttagctg aagcttttttt gttttattta tttttgtttt tcaggacagg gtaacagtcc    5700
tgtctgtcat ggacctcaat gtgtagacca gcctggcctt gaactaacag agatcttcct    5760
gcctttggga gtaaaggccg catgtgccac cacacctggc tattgaagtt gcttttttgtt    5820 ttgttttgtt ttaagtcctg tctttgctgt cactttctga gtgctgagta acaccaaact    5880
ctgaagaagt taaaaaaaaa aaaagatta tatttatttg tgtgtgtata catgtactga    5940
tcttgtgtgc aagtcggagg acaaattgca ggaggtggct ctcgctacct tatatacgtt    6000
tctaggttaa actcaggtag gcctggcaga aaagtgcctt tacccacaaa gccacattgc    6060
tggcccaaaa actcagattc tgagcccta atccaaatac agagagccct taggaatagg    6120
taaagatgtg ccctcccagt gcctcagcag cctgatctcc ctggggttaa aagttgtgat    6180
ggccagcctg agctacacag cgagactctg tctaaaaaaa gtggtgtgtg tgtgtgtgtg    6240
tgtggtggtg gtgcggcac tcaggaggca gaggcagagg caggcagatc tctgagttca    6300
tggctagcct gatctaccaa gggaattcca agatagccag ggctacagag agaaaccctg    6360
tcttgatctc ctccagagca gggcaaagtg tgatgagcag gcaggcacca gcacccgcca    6420
gcctcaccca tgcaggctcc agctttgctt ggctttccct gggttcactt ggtattgctt    6480
tcattttcgt ttctcagtgc aggaagtctg caagagaaag taatgggaca gtgctgggga    6540
aagccttgct cttgggtggc agtgactaga aaagtcccct ggacacgact gcattctgaa    6600
tatcaccaac tctgaagtgc acccaaggct tttgaacacc atgtgccgtc cacacctgac    6660
ctcaccagat gggtggcagt gaccgcacag gcacactgtg catagggcat accatcttca    6720
gagggcccat gtgctgctgg attgctagga cactttccca gcatgcgtga agccctgggt    6780
tccatgccca cctcacataa accaagtgtg gctgtgcaca cctttaatcc cagcactggg    6840
taggcaaagg caggcagatc tgtgaggcca gcctgctcta cataaagttc caggccagtt    6900
acacacagac aaacacacac acacacacat acacacacac agagagagag ccttgaagct    6960
gtgtaaggtc aatatggacc agcataaaag tagtttgttt atttatttag attttttgaga    7020 tagcaggttg tcatggccct tggcttttgt ctgaaactca agattctcac atgtcaggtt    7080
cccaagtgct gagacttgac atgggccttg atggctcgag tgaagttgtt tataccatac    7140
tcttattcct taggtgtctc atcatttgtg taaaatattc ctacatctga aaaaaaacaa    7200
gtgccaagct gtaaactgcc agtcattta tgtttttattt ttattaatct aaaaattgta    7260
ttgtattgta ttgatttagg gggcaatgtg tgtgccacag ttcatgtgga ggtcagaaga    7320
```

```
caacttgcag gagttgattc ttccagcata tgagtcctgg ggttaaataa acaaacaaac   7380
aaataaacaa attaagaacc cagtgccttt ctgagctagt aaaggcactc actgccaagc   7440
cagaagacca gtcccaggaa ggtgagaccc cccccccatc agacatgagt acattcacac   7500
acatacacaa taagccaata agtaaatgta attaaaaact atgtagaaca ggtggcctgg   7560
aactcacaga catcttcctc tcccttccaa gtgaatatta gtccaatgct gggattaaag   7620
gccagactag gttcaattgt ttattttgat ataagatctt actatgttgt cctagctggt   7680
ctggaactgg cttatgggga ccaatctggc cttgaattca gacatcctct tgcctctgcc   7740
tcccctgata tgggggatta taggagtgtg ccactacacc tagctatata tatttttt    7800 taaaaaatt aaaactaaaa tcaatacagg agcctaaaga gtccacagtg tgtggcctgt   7860 gtgaccccg tgtatgggt gctcggcctg gatggagggc ttcccttctc acctgagctc     7920
cctgcaggtg gccaagcagg aggagttctt caacctgtca cactgccagc tggccacgct   7980
catcagccgg gatgatctga acgtacgctg cgagtccgag gtgttccacg cgtgcatcga   8040
ctgggtcaaa tacgactgcc cgcagcggcg cttctacgtg caggcactgc tgcgggccgt   8100
gcgctgccat gcgctcacgc cgcgcttcct gcagacgcag ctgcagaagt gtgagatcct   8160
gcaggccgac gcgcgctgca aggactacct ggtgcagata ttccaggagc tcacgctgca   8220
caagcccacg caggcagtgc cctgccgcgc gcccaaagtg ggccgcctca tctacacagc   8280
gggcggttac ttccgacagt cgctcagcta cctggaggcc tacaacccga gcaatggctc   8340
ctggctgcgc ctggccgatc tacaggtgcc gcgcagtggg ctggcaggct gcgtggtggg   8400
tgggctgcta tacgctgtgg gcggccgcaa caactctccg gatggcaaca ctgactccag   8460
cgccctggac tgctacaacc ccatgaccaa ccagtggtcg ccctgtgcct ctatgagcgt   8520
gccacgcaac cgcatcgggg tgggggtcat agatggccac atctacgcag tcggggggttc   8580 ccacggctgc atccaccaca gcagcgtgga gaggtgagca ccgggggccc aaagagacgg   8640
tacctgttct tgtccctgcc ttcatatgag gttgagcggc tgggatgttc attctcagtg   8700
tccagagttg ggaagtactg gaggggggctg tcccaaaacct acaggaacca ccgctgcaca   8760
ctgggggtag taggaattac tctaatacgt gaattatatt gtgcaattta taattacttt   8820
aaaaggtatc atctgaacgg ggatgtagtt cagtggtagt gctctggtat cttttcttttt   8880 aaaaagattt tatttatgtg tataagtaca ctgtagcagt cttcagacac accagaagag   8940
ggcggcagat tcattatgg gtggttgtga gccaccatgt gtttgctggg atttgaactc    9000
aggaccttcc gttggtactc ttaaccactg agccatctct ccagtcctct ggtctctttc   9060
ttgaatccag ggtttaaggt ctcatcccca gccctgccaa aaggaaggag ggaaaagaag   9120
aaaaagggct gggggtgtga ctcagttggc agagcacttg ccccgcgttc aggaagccct   9180
cataaaccca gctgtcatcc cagcgctctg ggggtagagg gaggagaatc aggaattcaa   9240
tatttatctt tggctgtatg gcaagttcaa ggccagcctg ggatataaga gaccctgtct   9300
caagacagac aaacaacccc cccacacaca cacacacaaa tttagggctt ggagcaaggg   9360
taagaaaatg agaaaaaatt ttaattttgt atttgtagtg ctgggaatag aacctagaaa   9420
tctatgcttg ctaggtcagc tgtctacccc aagctaaccc cgcccatgcc tgaaaatgga   9480
aatgtaaaca aatgtgctag gggctctaat gtgtgtggtc tgtgaatagg gtggccctt    9540 caaggactgt aggatgcagg gatggactgg acgctgctgg gctaatgggg cgtgttcacc   9600
catctctgat catgttgctc agagaaccac ctgggagacc cagttagaca tttggagttg   9660
```

```
aacacctgcc cagatgtcac ttagtgaccc tggatgtcct accccacatg tctgtagcaa    9720
atcttgtggt gtgaggcaat gaatcctgct aggggtgaag tgcacaggtg ctgcagccct    9780
aagggataaa gccgtctagg ctagagggaa ttgctgttgc tgtcagtcat aattgatgac    9840
agtgaacctg gattctgatg acccctcact tctggagcca ggctggtgc tgcacatcct     9900 tcatctctcc gcactgggga gactaaagca ggagatcgcg gagagttcaa ggctagcttg    9960
aactacatag cagggttcta tctcaaaaca aacaaaaaac caaccaaaca aaaacctaaa    10020
aataaatgtg caagcagatg gagggccgtg gtgtaagggt tgaccacggg tgaccacggg    10080
gtattatgtc ttttgcagat atgagccaga gcgggacgag tggcatctag tcgcgccaat    10140
gttgacacgg aggattggcg tgggcgtggc agtgctcaac cgcttgctgt atgcagtggg    10200 gggcttttgac gggactaacc ggcttaactc cgcagaatgt tactatccag agaggaatga   10260
gtggcggatg atcacaccga tgaataccat ccggagcggg gccggtgagt ggggggtgga    10320
gtgaggacag cccagcccag cgaggaagcg aggaagcgtt tgctttaccc tcctccctct   10380
gttacatgac tgaggctgcc ctcgaagtcc ttatgtcgct gaggttgact ttgaactcct    10440
gatcctccta ctccagcttc tccagtggtg gagggaaggg cagtggctac taaagtccct    10500
tgtccagtgg ccctgcccc accccccacc ccagaccagg cttacggtga ctcccactgt     10560
gcgctttcct ttaggggtct gcgtgctgca caactgtatc tatgcagcag ggggctacga    10620
tgggcaggac cagttgaaca gtgtggagcg ctacgacgtg gagacagaga cctgactttt     10680
cgtagccccc atgaggcatc accgtagtgc gctgggatt actgtgcacc agggcaagat     10740
ctacgtcctc ggtgaggccc ttggaggctg gatcagggtg aaaaccacac ttgagtgtcc    10800 atatctttc ttctccaagt tttggtgctg agtataaaag ccagagagtc ccgaatgctt      10860
ggcaagtgtc ctttaattgt gccccgcccc actgggggat tctgggccga agctctacta    10920
ctaagccgct ccccccaccca ctcttacaac acttcccacc ctgtaccca ccttcactgg    10980 gaagtttagg caggggctct agactgaacc acattccacc tccaacctat ccatcgcaaa    11040 caggggggctt ctttttccctt ctgttctctg ccgccttgcg tggtaggctg ggcactctga    11100
gggggtgacc attctcttca ttctccctgc aggaggctat gatggccaca cttttctgga   11160
cagtgtggaa tgctatgacc cggacagtga tacctggagt gaggtgaccc gcatgacatc    11220
tggccgcagc ggggtgggtg tggccgtcac catggaaccc tgtcggaagc aaattgatca    11280
acaaaactgt acctgctgaa gcacttggaa tacctgagca ctgacaacag gacagaaaaa    11340
cagtctgtgt atcactgctt ctctgtacta aagaaaaaag aagaaaacaa agcataaaca    11400
gaaaacacag ggccgaagag gcggcagaag aagtcatccc ttcttccagg aagggcgact    11460
gggatgcctt gtaaaggacc ttgtggaaga ccagaactca aatccatggg cccatctgtc    11520
atagccctgg agcgtccaag tctgggatgg ggtatgggcg gggcaccctc acaggtgaga    11580
agcccttgaa ctcccaccac cagaagggg gggacaggca aagcaggaga tcacatgttt    11640
ttttctttgg ttcctgcaac tcggtgatca attccagtgg acaggggaag aagggacagc    11700
tgaggccaag gggctgaggc tccctctgga actggggccc aagggacaag ccggcacaga    11760
gaagcctctg ggctctgagc cctgaacagt tattttgtta aataaccctg taagtttccc    11820
atgggaataa agaatggagt aggcacacag gtcttcagag ggcggtcgga atccctcagg   11880
gagagacagc tcttctattg aaatacacgc agatcctgat ggggctggta tctgaaaccc    11940
gtctattgtc tctgcttgcc attgtacatt ctgctcagac agggcatctt gcttcttgtg    12000
ggacacacag ttgtctgtca gtttcagggc attagaagcc aatgacctaa cttctgtgcc    12060
```

```
tcctaacttc tcctggggcc tcctgtgttt agctttattt tgaggcaggg actcacgtcg   12120
tccgggatgg ccttcagttc agaccttgaa ctgacgctgc cgcctgtccc agcctaccga   12180
gtgctggggc tacatctgta tagcgcaatg cctggttcct gcttattatt tttgtaccca   12240
agcaggaaaa taaaggtttc tgggacattg ggtgtggctc tgaattaacc tgacatgtat   12300
gagccctggg ttccatccct agcacctgta aactaggcac ggtggaccac acctgtaatc   12360
ctagcagcag gggcagaacc atgctggagt tcatacataa ccaatgaagg ccagcctggc   12420
caatagagac cttgtctcag agagtagtgg ccaggcagtg gtggcgcatg cctttaatct   12480 ctgcccttttg gaggcagagg caggaggatt tctgccaagt ttgaggccag tttggtcttc   12540
agagtgaaat tcaggatagg cagggctgtt gttatacaga gaaactgtct ccaaaaaagc   12600
aaagcaaaac aacaacaaaa accatgtgca accaaggctg ggcccttggg actattttga   12660
aaagcaccag aagaaagact cagggtcatc ctgggctctc tgtggagctg gaagctatcc   12720
tgagctacag tagacaaggt caacaaaggt gcacacctttt gatcccagga gccagagatg   12780
gctcagcagt taagggcacc aatgcgttcc agaggctcag cttttgttcc cagtactcag   12840
gtttggtgtt tcactgacac acctgtacct ccatctccac tggaccccccc ccccctttc    12900 actagtttcc ttagatgtct tcatgtgtaa agtgtagctt ggaatggtag cacaaacctg   12960 caacccaat gatgggaagc tgaggcagga ggattgtgac ttcaaggcca gcctgggcta    13020
catctatatg gagctagtgt ggtggcacgc accttgaatc ccaatgctgg aaggggcag    13080 gcagatctct gaattccagc ccaagctaca tgatgagctc atgccacaga tcgactccat   13140
ccacacatta ggctagagag gtggcctctt ggctcttccc aaggacccga gcctggctca   13200
taaccagagc tgtctgtgag gcacctgtcc acaaatgtat ggacagacaa acacacagct   13260
atatatacct aaaaagtctc tcaaaaagct ggaaatgaag ctcaatagag cccttgcaga   13320
tgggggctgg ggggcggcg gcagaaactc ggatctctgt gaattgggac cagcctggtc    13380
ttcatagacc tgggggagaga gagagagaga gagagagaga gagagagaga gagagagaga   13440
gagagagaga gagagagaga gagagaagag agagaagaga gagaggagag agaactaata   13500 ctgagccccct gccctagagt cctacagtga ggagccgggg taagaacact cgctcactct   13560
gcaagcaaag gacctgaacc tgaactccca gctgcatgcc tgtgatccca gcatgccagc   13620
cagcctggct gaaatggtaa atttcaggtt cagtgaaata ccatgggggg aaggggggtg   13680
gggggggtgg gcggggagaa acaccagca ttcctctgtc ctccacctct gtacaaaatg    13740
tgggaataca acacagggag agaggagaag gaagaaagga aggaaagaga aagaaagaga   13800
gagctgctga gctgttcaga gcaccgactg ctccggcaga ggacccaggt tcagtcccta   13860
gcacgatcat cacaactacc tgtgacccttt cagtcctgtg ggctctgatg ccttccggac   13920
tggataggct cctgtacgct gcatgtgaac tcgcaaaagc acacatacat ttaaaaacat   13980
tttttttttt aagagagaag gaagcaaaga ggatttctat gtctgtagca caattggttt   14040
gcagggtctg gaaggaagga aagagaagga aataggaggg aaccttcgac gtgggcagcc   14100
ttgaggaact tcatagatgt cacccgggta gttttttcag cgtttcttac tattttaatt   14160
acacttgttc gtgtttgggg gagaggcaggg gtgcagtcac actgacggtt gtgtgggtgt   14220
cagagaactt tcaggagtgg gttcttctgc cacatggatt ctgggtctca aacacagggc   14280
taagactagc ggcaagcccc tctacccact gagctctctc atcagctcct ttccaggtag   14340
ctcctcagcg tgtggataaa ggaaacaaaa gaaagtcgtg tgcatagccg ggaggggcat   14400
```

```
gcgcagctga gatcagcctc ccagggtggg cggcgactct caccgcagtg gggtgagctc    14460
tgctgcagag cggagggtta gtggagggtt acggccctca ctcaggtcaa ggtcgagtcc    14520
gaggctgctg ggtctcagga tcaggtgcgt ttgctggttg ttatctgtga ggaccggact    14580
ttggacatct attgggcagc acgtcctgcg gcagctgatg gactagggc caagcttgct     14640 gacttgtatg gttttctttt cggtgttggg gcttgaaccc agggtctgtt gtacactaaa    14700
tatgcattct accaatgagc tacaccctca tgccccaaaa tgagcatttc cttcctcccc    14760 ttttttaaaaa tttgttttt taatgttttt cttttcttt tttcttttg gttttttgat      14820 acagggtctc tgtgtagcct tggctgtcct ggaactcact ctgtaggcca ggctggcctc    14880
aaactcagag atctgcctgg ctctgtgtcc agaggcatgt gccaccctg cctgtctccc     14940 agtgtgtttt tccatttctt tattgcgtgt atgtgtttgt gtgttggggt cagtgtcatg    15000
```

<210> SEQ ID NO 7
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 7
tattcagaat gcagtc                                                    16

<210> SEQ ID NO 8
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 8
acatgtcaga ttcctt                                                    16

<210> SEQ ID NO 9
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 9
aatgatatct aagtgc                                                    16

<210> SEQ ID NO 10
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 10
ggccaatacg ccgtca                                                    16

<210> SEQ ID NO 11
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 11
ggctactacg ccgtca                                                    16

<210> SEQ ID NO 12
<211> LENGTH: 25
<212> TYPE: DNA
<213> ORGANISM: Artificial sequence
<220> FEATURE:
<223> OTHER INFORMATION: Primer

<400> SEQUENCE: 12
aaggtcatgg aaaggcttat tgagt                                          25

<210> SEQ ID NO 13
<211> LENGTH: 21
<212> TYPE: DNA
<213> ORGANISM: Artificial sequence
<220> FEATURE:
<223> OTHER INFORMATION: Primer

<400> SEQUENCE: 13
gttcatcacg tgcaggacac a                                              21

<210> SEQ ID NO 14
<211> LENGTH: 16
<212> TYPE: DNA
<213> ORGANISM: Artificial sequence
<220> FEATURE:
<223> OTHER INFORMATION: Probe

<400> SEQUENCE: 14
tctccgtggg cgagaa                                                    16

<210> SEQ ID NO 15
<211> LENGTH: 20
<212> TYPE: DNA
<213> ORGANISM: Artificial sequence
<220> FEATURE:
<223> OTHER INFORMATION: Primer

<400> SEQUENCE: 15
cccctttccc tctgctgaag                                                20

<210> SEQ ID NO 16
<211> LENGTH: 24
<212> TYPE: DNA
<213> ORGANISM: Artificial sequence
<220> FEATURE:
<223> OTHER INFORMATION: Primer

<400> SEQUENCE: 16
tgcagcttca ctgaatcttg aaag                                           24

<210> SEQ ID NO 17
<211> LENGTH: 32
<212> TYPE: DNA
<213> ORGANISM: Artificial sequence
<220> FEATURE:
<223> OTHER INFORMATION: Probe

<400> SEQUENCE: 17
ttccttgctt cttgaatttg ttttgcatcc at                                  32

<210> SEQ ID NO 18
<211> LENGTH: 21
<212> TYPE: DNA
<213> ORGANISM: Artificial sequence
<220> FEATURE:

```
<223> OTHER INFORMATION: Primer

<400> SEQUENCE: 18
cctggaagga tggaagaaac g                                              21

<210> SEQ ID NO 19
<211> LENGTH: 20
<212> TYPE: DNA
<213> ORGANISM: Artificial sequence
<220> FEATURE:
<223> OTHER INFORMATION: Primer

<400> SEQUENCE: 19
caggctgctt ggagcaaaat                                                20

<210> SEQ ID NO 20
<211> LENGTH: 25
<212> TYPE: DNA
<213> ORGANISM: Artificial sequence
<220> FEATURE:
<223> OTHER INFORMATION: Probe

<400> SEQUENCE: 20
aaaccgtctg ggaggagacc ccact                                          25

<210> SEQ ID NO 21
<211> LENGTH: 19
<212> TYPE: DNA
<213> ORGANISM: Artificial sequence
<220> FEATURE:
<223> OTHER INFORMATION: Primer

<400> SEQUENCE: 21
ggccattgcc cagattttc                                                 19

<210> SEQ ID NO 22
<211> LENGTH: 22
<212> TYPE: DNA
<213> ORGANISM: Artificial sequence
<220> FEATURE:
<223> OTHER INFORMATION: Primer

<400> SEQUENCE: 22
cggttgagca gacagtgaat ga                                             22

<210> SEQ ID NO 23
<211> LENGTH: 22
<212> TYPE: DNA
<213> ORGANISM: Artificial sequence
<220> FEATURE:
<223> OTHER INFORMATION: Probe

<400> SEQUENCE: 23
ccagattggc cccttggcaa gc                                             22

<210> SEQ ID NO 24
<211> LENGTH: 22
<212> TYPE: DNA
<213> ORGANISM: Artificial sequence
<220> FEATURE:
<223> OTHER INFORMATION: Primer

<400> SEQUENCE: 24
cactaaggtg gcctacctcc aa                                             22
```

```
<210> SEQ ID NO 25
<211> LENGTH: 23
<212> TYPE: DNA
<213> ORGANISM: Artificial sequence
<220> FEATURE:
<223> OTHER INFORMATION: Primer

<400> SEQUENCE: 25
agctcgcttg aatgctgtat ttc                                            23

<210> SEQ ID NO 26
<211> LENGTH: 22
<212> TYPE: DNA
<213> ORGANISM: Artificial sequence
<220> FEATURE:
<223> OTHER INFORMATION: Probe

<400> SEQUENCE: 26
cccaggcacg gctaaggttg gc                                             22

<210> SEQ ID NO 27
<211> LENGTH: 23
<212> TYPE: DNA
<213> ORGANISM: Artificial sequence
<220> FEATURE:
<223> OTHER INFORMATION: Primer

<400> SEQUENCE: 27
gcgaggtcct gaaagatatt gag                                            23

<210> SEQ ID NO 28
<211> LENGTH: 20
<212> TYPE: DNA
<213> ORGANISM: Artificial sequence
<220> FEATURE:
<223> OTHER INFORMATION: Primer

<400> SEQUENCE: 28
gccacttctg cacgttacca                                                20

<210> SEQ ID NO 29
<211> LENGTH: 27
<212> TYPE: DNA
<213> ORGANISM: Artificial sequence
<220> FEATURE:
<223> OTHER INFORMATION: Probe

<400> SEQUENCE: 29
cttctgaaca tcacagcaga ccctggg                                        27

<210> SEQ ID NO 30
<211> LENGTH: 24
<212> TYPE: DNA
<213> ORGANISM: Artificial sequence
<220> FEATURE:
<223> OTHER INFORMATION: Primer

<400> SEQUENCE: 30
tgactccata tcctcatcca caag                                           24

<210> SEQ ID NO 31
<211> LENGTH: 20
<212> TYPE: DNA
<213> ORGANISM: Artificial sequence
<220> FEATURE:
<223> OTHER INFORMATION: Primer
```

<400> SEQUENCE: 31
aggtgtaagg cgctcatgct                                               20

<210> SEQ ID NO 32
<211> LENGTH: 30
<212> TYPE: DNA
<213> ORGANISM: Artificial sequence
<220> FEATURE:
<223> OTHER INFORMATION: Probe

<400> SEQUENCE: 32
caccttcatc ccacctatca ctgtcttccc                                    30

<210> SEQ ID NO 33
<211> LENGTH: 20
<212> TYPE: DNA
<213> ORGANISM: Artificial sequence
<220> FEATURE:
<223> OTHER INFORMATION: primer

<400> SEQUENCE: 33
tggttgcctt ccgtgtctct                                               20

<210> SEQ ID NO 34
<211> LENGTH: 19
<212> TYPE: DNA
<213> ORGANISM: Artificial sequence
<220> FEATURE:
<223> OTHER INFORMATION: primer

<400> SEQUENCE: 34
tcagctcggg aatgcacaa                                                19

<210> SEQ ID NO 35
<211> LENGTH: 26
<212> TYPE: DNA
<213> ORGANISM: Artificial sequence
<220> FEATURE:
<223> OTHER INFORMATION: probe

<400> SEQUENCE: 35
agattgaagc tttgcagaac gcagcg                                        26

<210> SEQ ID NO 36
<211> LENGTH: 19
<212> TYPE: DNA
<213> ORGANISM: Artificial sequence
<220> FEATURE:
<223> OTHER INFORMATION: primer

<400> SEQUENCE: 36
ggcctcaagg acgacaaca                                                19

<210> SEQ ID NO 37
<211> LENGTH: 22
<212> TYPE: DNA
<213> ORGANISM: Artificial sequence
<220> FEATURE:
<223> OTHER INFORMATION: primer

<400> SEQUENCE: 37
accacccatt cagttgtcaa tg                                            22

<210> SEQ ID NO 38
<211> LENGTH: 25

```
<212> TYPE: DNA
<213> ORGANISM: Artificial sequence
<220> FEATURE:
<223> OTHER INFORMATION: probe

<400> SEQUENCE: 38
catcttctct gtccccaccg accaa                                    25
```

METHODS OF MODULATING KEAP1

SEQUENCE LISTING

The present application is being filed along with a Sequence Listing in electronic format. The Sequence Listing is provided as a file entitled BIOL0291USASEQ_ST25.txt, created on Sep. 13, 2018 which is 72 MB in size. The information in the electronic format of the sequence listing is incorporated herein by reference in its entirety.

FIELD OF THE INVENTION

The present embodiments provide methods, compounds, and compositions for treating, preventing, or ameliorating a disease related to oxidative stress such as insulin resistance, non-alcoholic steatohepatitis (NASH) and non-alcoholic fatty liver disease (NAFLD), by administering a Kelch-like ECH-associated protein 1 (KEAP1) specific inhibitor to an individual.

BACKGROUND

Oxidative stress, which results from an imbalance between the generation of electrophiles (e.g., free radicals) and the antioxidant response in a body, has been linked to a number of pathologic processes including diabetes, insulin resistance, obesity, non-alcoholic steatohepatitis (NASH) and non-alcoholic fatty liver disease (NAFLD). Oxidative stress linked complications of diabetes include stroke, neuropathy, retinopathy and nephropathy.

Kelch-like ECH-associated protein 1 (KEAP1) functions as an oxidative stress-sensitive substrate adaptor protein for a Cul3-based E3 unbiquitin ligase complex. KEAP1 and the substrates it binds are key regulators of the antioxidant response and KEAP1 is a key defence against oxidative stress.

Transcription factor NF-E2-related factor 2 (NRF2) is a substrate of KEAP1. KEAP1 acts upstream of Nrf2 in the cellular response to oxidative and xenobiotic stress. KEAP1 binds NRF2 and, under normal quiescent conditions, KEAP1 sequesters NRF2 in the cytoplasm and targets NRF2 for ubiquitination and degradation. However, in the presence of xenobiotics or oxidative stress (for example the presence of electrophiles such as reactive oxygen species (ROS)), KEAP1 releases NRF2 which then translocates to the nucleus where it binds to antioxidant response elements (AREs) and initiates transcription of a battery of cytoprotective detoxifying and antioxidant genes including glutathione 5-transferase alpha 1 (GSTA1) and NAD(P)H: Quinone Oxidoreductase 1 (NQO1). Thus, KEAP1 represses Nrf2 function by detecting oxidative stress signals, and the stress signals release KEAP1 repression of Nrf2 (Chartoumpekis, et al., 2015, *Biochem. Soc. Trans.* 43:639-644; Padmanabhan, et al., 2006, Molecular Cell 21:689-700; Wakabayashi, et al., 2003, *Nature Genetics* 35:238-245).

Phosphoglycerate mutase family member 5 (PGAM5) is another substrate of KEAP1. KEAP1 interaction with PGAM5 targets it for ubiquitination and degradation and is another defense mechanism against oxidative stress (Lo and Hannink, *J Biol Chem,* 2006, 281(49): 37893-37903).

It has been shown in several mouse models that reducing KEAP1 expression leads to a heightened antioxidant response, making it an attractive pharmacologic target. Studies have been conducted with KEAP1 knockout mice (Ramadori et al., *Free Radic Biol Med,* 2016, 91:114-126; Xu et al., *PLoS One,* 2013 8(11):e79841; Kulkarni et al., *Pharm Res,* 2013, 30(9):2221-31), small molecule inhibitors (Shimozono et al., *Mol Pharmacol,* 2013, 84(1):62-70) and nucleic acid inhibitors such as siRNA (Xu et al., *Cancer Res.* 2013, 73(14): 4406-4417; Soares et al., *Diabetes,* 2016 65(3)633-646; Gonzalez-Rodriguez et al., *Dis Model Mech,* 2014, 7(9):1093-100; Zhong et al., *Invest Ophthalmol Vis Sci,* 2013, 54(6):3941-8; U.S. Pat. No. 8,785,408) to treat a disease related to oxidative stress. However, to date, no therapeutic strategies to target KEAP1 are commercially available. Accordingly, there is an unmet need to develop KEAP1 inhibitors for use in treating KEAP1 related diseases or conditions.

SUMMARY

Certain embodiments disclosed herein provide compounds or compositions comprising a KEAP1 modulator. In certain embodiments, the KEAP1 modulator is a KEAP1 specific inhibitor. In certain embodiments, the KEAP1 specific inhibitor is a nucleic acid, polypeptide, antibody, small molecules, or other agent capable of inhibiting the expression of KEAP1. In certain embodiments, the nucleic acid is a compound or composition targeting KEAP1. In certain embodiments, the compound or composition comprises deoxyribonucleotides. In certain embodiments, the compound or composition comprises ribonucleotides. In certain embodiments, the compound or composition is single stranded. In certain embodiments, the compound or composition is double stranded. In certain embodiments, the compound or composition targeting KEAP1 comprises an oligonucleotide. In certain embodiments, the oligonucleotide is single stranded. In certain embodiments, the oligonucleotide is double stranded. In certain embodiments, the oligonucleotide is a modified oligonucleotide. In certain embodiments, the modified oligonucleotide is single stranded. In certain embodiments, the modified oligonucleotide is double stranded. In any of the foregoing embodiments, the compound can be an antisense compound or oligomeric compound.

Certain embodiments disclosed herein provide a method of reducing KEAP1 expression in an animal comprising administering to the animal a compound or composition comprising a KEAP1 specific inhibitor.

Certain embodiments disclosed herein provide a method of reducing oxidative stress in an animal comprising administering to the animal a therapeutically effective amount of a compound or composition comprising a KEAP1 specific inhibitor.

Certain embodiments disclosed herein provide a method of treating, preventing, delaying or ameliorating a disease, disorder or condition related to oxidative stress in an animal comprising administering to the animal a therapeutically effective amount of a compound or composition comprising a KEAP1 specific inhibitor.

Certain embodiments disclosed herein provide a method of treating an animal at risk for a disease, disorder or condition related to oxidative stress comprising administering to the animal a therapeutically effective amount of a compound or composition comprising a KEAP1 specific inhibitor.

In certain embodiments, the KEAP1 specific inhibitor is a nucleic acid, peptide, antibody, small molecule or other agent capable of inhibiting the expression of KEAP1. In certain embodiments, the KEAP1 specific inhibitor comprises a compound or composition described herein. In certain embodiments, the compound or composition comprises an antisense compound or an oligomeric compound.

In certain embodiments, the compound or composition comprises a modified oligonucleotide. In certain embodiments, the compound or composition comprises a modified oligonucleotide 8 to 80 linked nucleosides in length and having a nucleobase sequence comprising at least an 8, 9, 10, 11, 12, 13, 14, 15, 16, 17, 18, 19 or 20 contiguous nucleobase portion complementary to the sequence of any one of SEQ ID NOs: 1-6. In certain embodiments, the modified oligonucleotide consists of 10 to 30 linked nucleosides. In certain embodiments, the modified oligonucleotide consists of 16 linked nucleosides. In certain embodiments, the modified oligonucleotide consists of 20 linked nucleosides.

In certain embodiments, the disease, disorder or condition related to oxidative stress is a metabolic disease, disorder or condition. In certain embodiments, the metabolic disease, disorder or condition is insulin resistance. In certain embodiments, the disease, disorder or condition related to oxidative stress is NASH and/or NAFLD.

DETAILED DESCRIPTION OF THE INVENTION

It is to be understood that both the foregoing general description and the following detailed description are exemplary and explanatory only and are not restrictive of the embodiments, as claimed. Herein, the use of the singular includes the plural unless specifically stated otherwise. As used herein, the use of "or" means "and/or" unless stated otherwise. Furthermore, the use of the term "including" as well as other forms, such as "includes" and "included", is not limiting.

The section headings used herein are for organizational purposes only and are not to be construed as limiting the subject matter described. All documents, or portions of documents, cited in this application, including, but not limited to, patents, patent applications, articles, books, treatises, and GenBank and NCBI reference sequence records are hereby expressly incorporated by reference for the portions of the document discussed herein, as well as in their entirety.

It is understood that the sequence set forth in each SEQ ID NO in the examples contained herein is independent of any modification to a sugar moiety, an internucleoside linkage, or a nucleobase. As such, compounds defined by a SEQ ID NO may comprise, independently, one or more modifications to a sugar moiety, an internucleoside linkage, or a nucleobase. Compounds described by ISIS number (ISIS #) indicate a combination of nucleobase sequence, chemical modification, and motif.

Unless otherwise indicated, the following terms have the following meanings:

"2'-deoxynucleoside" means a nucleoside comprising 2'-H(H) furanosyl sugar moiety, as found in naturally occurring deoxyribonucleic acids (DNA). In certain embodiments, a 2'-deoxynucleoside may comprise a modified nucleobase or may comprise an RNA nucleobase (uracil).

"2'-O-methoxyethyl" (also 2'-MOE and 2'-O(CH$_2$)$_2$—OCH$_3$) refers to an O-methoxy-ethyl modification at the 2' position of a furanosyl ring. A 2'-O-methoxyethyl modified sugar is a modified sugar.

"2'-MOE nucleoside" (also 2'-O-methoxyethyl nucleoside) means a nucleoside comprising a 2'-MOE modified sugar moiety.

"2'-substituted nucleoside" or "2-modified nucleoside" means a nucleoside comprising a 2'-substituted or 2'-modified sugar moiety. As used herein, "2'-substituted" or "2-modified" in reference to a sugar moiety means a sugar moiety comprising at least one 2'-substituent group other than H or OH.

"3' target site" refers to the nucleotide of a target nucleic acid which is complementary to the 3'-most nucleotide of a particular compound.

"5' target site" refers to the nucleotide of a target nucleic acid which is complementary to the 5'-most nucleotide of a particular compound.

"5-methylcytosine" means a cytosine with a methyl group attached to the 5 position.

"About" means within ±10% of a value. For example, if it is stated, "the compounds affected about 70% inhibition of a KEAP1", it is implied that KEAP1 levels are inhibited within a range of 60% and 80%.

"Administration" or "administering" refers to routes of introducing a compound or composition provided herein to an individual to perform its intended function. An example of a route of administration that can be used includes, but is not limited to parenteral administration, such as subcutaneous, intravenous, or intramuscular injection or infusion.

"Administered concomitantly" or "co-administration" means administration of two or more compounds in any manner in which the pharmacological effects of both are manifest in the patient. Concomitant administration does not require that both compounds be administered in a single pharmaceutical composition, in the same dosage form, by the same route of administration, or at the same time. The effects of both compounds need not manifest themselves at the same time. The effects need only be overlapping for a period of time and need not be coextensive. Concomitant administration or co-administration encompasses administration in parallel or sequentially.

"Amelioration" refers to an improvement or lessening of at least one indicator, sign, or symptom of an associated disease, disorder, or condition. In certain embodiments, amelioration includes a delay or slowing in the progression or severity of one or more indicators of a condition or disease. The progression or severity of indicators may be determined by subjective or objective measures, which are known to those skilled in the art.

"Animal" refers to a human or non-human animal, including, but not limited to, mice, rats, rabbits, dogs, cats, pigs, and non-human primates, including, but not limited to, monkeys and chimpanzees.

"Antisense activity" means any detectable and/or measurable activity attributable to the hybridization of an antisense compound to its target nucleic acid. In certain embodiments, antisense activity is a decrease in the amount or expression of a target nucleic acid or protein encoded by such target nucleic acid compared to target nucleic acid levels or target protein levels in the absence of the antisense compound to the target.

"Antisense compound" means a compound comprising an oligonucleotide and optionally one or more additional features, such as a conjugate group or terminal group. Examples of antisense compounds include single stranded and double stranded compounds, such as, oligonucleotides, ribozymes, siRNAs, shRNAs, ssRNAs, and occupancy-based compounds.

"Antisense inhibition" means reduction of target nucleic acid levels in the presence of an antisense compound complementary to a target nucleic acid compared to target nucleic acid levels in the absence of the antisense compound.

"Antisense mechanisms" are all those mechanisms involving hybridization of a compound with target nucleic acid, wherein the outcome or effect of the hybridization is either target degradation or target occupancy with concomitant stalling of the cellular machinery involving, for example, transcription or splicing.

"Antisense oligonucleotide" means an oligonucleotide having a nucleobase sequence that is complementary to a target nucleic acid or region or segment thereof. In certain embodiments, an antisense oligonucleotide is specifically hybridizable to a target nucleic acid or region or segment thereof.

"Bicyclic nucleoside" or "BNA" means a nucleoside comprising a bicyclic sugar moiety. "Bicyclic sugar" or "bicyclic sugar moiety" means a modified sugar moiety comprising two rings, wherein the second ring is formed via a bridge connecting two of the atoms in the first ring thereby forming a bicyclic structure. In certain embodiments, the first ring of the bicyclic sugar moiety is a furanosyl moiety. In certain embodiments, the bicyclic sugar moiety does not comprise a furanosyl moiety.

"Branching group" means a group of atoms having at least 3 positions that are capable of forming covalent linkages to at least 3 groups. In certain embodiments, a branching group provides a plurality of reactive sites for connecting tethered ligands to an oligonucleotide via a conjugate linker and/or a cleavable moiety.

"Cell-targeting moiety" means a conjugate group or portion of a conjugate group that is capable of binding to a particular cell type or particular cell types.

"cEt" or "constrained ethyl" means a bicyclic furanosyl sugar moiety comprising a bridge connecting the 4'-carbon and the 2'-carbon, wherein the bridge has the formula: 4'-CH(CH$_3$)—O-2'.

"Constrained ethyl nucleoside" (also cEt nucleoside) means a nucleoside comprising a cEt.

"Chemical modification" in a compound describes the substitutions or changes through chemical reaction, of any of the units in the compound. "Modified nucleoside" means a nucleoside having, independently, a modified sugar moiety and/or modified nucleobase. "Modified oligonucleotide" means an oligonucleotide comprising at least one modified internucleoside linkage, a modified sugar, and/or a modified nucleobase.

"Chemically distinct region" refers to a region of a compound that is in some way chemically different than another region of the same compound. For example, a region having 2'-O-methoxyethyl nucleotides is chemically distinct from a region having nucleotides without 2'-O-methoxyethyl modifications.

"Chimeric antisense compounds" means antisense compounds that have at least 2 chemically distinct regions, each position having a plurality of subunits.

"Cleavable bond" means any chemical bond capable of being split. In certain embodiments, a cleavable bond is selected from among: an amide, a polyamide, an ester, an ether, one or both esters of a phosphodiester, a phosphate ester, a carbamate, a di-sulfide, or a peptide.

"Cleavable moiety" means a bond or group of atoms that is cleaved under physiological conditions, for example, inside a cell, an animal, or a human.

"Complementary" in reference to an oligonucleotide means the nucleobase sequence of such oligonucleotide or one or more regions thereof matches the nucleobase sequence of another oligonucleotide or nucleic acid or one or more regions thereof when the two nucleobase sequences are aligned in opposing directions. Nucleobase matches or complementary nucleobases, as described herein, are limited to the following pairs: adenine (A) and thymine (T), adenine (A) and uracil (U), cytosine (C) and guanine (G), and 5-methyl cytosine ($^m$C) and guanine (G) unless otherwise specified. Complementary oligonucleotides and/or nucleic acids need not have nucleobase complementarity at each nucleoside and may include one or more nucleobase mismatches. By contrast, "fully complementary" or "100% complementary" in reference to oligonucleotides means that such oligonucleotides have nucleobase matches at each nucleoside without any nucleobase mismatches.

"Conjugate group" means a group of atoms that is attached to an oligonucleotide. Conjugate groups include a conjugate moiety and a conjugate linker that attaches the conjugate moiety to the oligonucleotide.

"Conjugate linker" means a group of atoms comprising at least one bond that connects a conjugate moiety to an oligonucleotide.

"Conjugate moiety" means a group of atoms that is attached to an oligonucleotide via a conjugate linker.

"Contiguous" in the context of an oligonucleotide refers to nucleosides, nucleobases, sugar moieties, or internucleoside linkages that are immediately adjacent to each other. For example, "contiguous nucleobases" means nucleobases that are immediately adjacent to each other in a sequence.

"Designing" or "Designed to" refer to the process of designing a compound that specifically hybridizes with a selected nucleic acid molecule.

"Diabetes mellitus" or "diabetes" is a syndrome characterized by disordered metabolism and abnormally high blood sugar (hyperglycemia) resulting from insufficient levels of insulin or reduced insulin sensitivity. The characteristic symptoms are excessive urine production (polyuria) due to high blood glucose levels, excessive thirst and increased fluid intake (polydipsia) attempting to compensate for increased urination, blurred vision due to high blood glucose effects on the eye's optics, unexplained weight loss, and lethargy.

"Diluent" means an ingredient in a composition that lacks pharmacological activity, but is pharmaceutically necessary or desirable. For example, the diluent in an injected composition can be a liquid, e.g. saline solution.

"Differently modified" mean chemical modifications or chemical substituents that are different from one another, including absence of modifications. Thus, for example, a MOE nucleoside and an unmodified DNA nucleoside are "differently modified," even though the DNA nucleoside is unmodified. Likewise, DNA and RNA are "differently modified," even though both are naturally-occurring unmodified nucleosides. Nucleosides that are the same but for comprising different nucleobases are not differently modified. For example, a nucleoside comprising a 2'-OMe modified sugar and an unmodified adenine nucleobase and a nucleoside comprising a 2'-OMe modified sugar and an unmodified thymine nucleobase are not differently modified.

"Dose" means a specified quantity of a compound or pharmaceutical agent provided in a single administration, or in a specified time period. In certain embodiments, a dose may be administered in two or more boluses, tablets, or injections. For example, in certain embodiments, where subcutaneous administration is desired, the desired dose may require a volume not easily accommodated by a single injection. In such embodiments, two or more injections may be used to achieve the desired dose. In certain embodiments, a dose may be administered in two or more injections to minimize injection site reaction in an individual. In other embodiments, the compound or pharmaceutical agent is administered by infusion over an extended period of time or continuously. Doses may be stated as the amount of pharmaceutical agent per hour, day, week or month.

"Dosing regimen" is a combination of doses designed to achieve one or more desired effects.

"Double stranded compound" means a compound comprising two oligomeric compounds that are complementary to each other and form a duplex, and wherein one of the two said oligomeric compounds comprises an oligonucleotide.

"Effective amount" means the amount of compound sufficient to effectuate a desired physiological outcome in an individual in need of the compound. The effective amount may vary among individuals depending on the health and physical condition of the individual to be treated, the taxonomic group of the individuals to be treated, the formulation of the composition, assessment of the individual's medical condition, and other relevant factors.

"Ensembl ID" is an identification number consisting of letters and numbers assigned to a gene sequence by Ensembl, which is a joint project between EMBL-EBI and the Wellcome Trust Sanger Institute to develop a software system that produces and maintans automatic annotation of selected eukaryotic genomes. Ensembl annotation helps identify a gene location in a particular genome and can be used to configure the equivalent gene on another species' genome.

"Expression" includes all the functions by which a gene's coded information is converted into structures present and operating in a cell. Such structures include, but are not limited to the products of transcription and translation.

"Gapmer" means an oligonucleotide comprising an internal region having a plurality of nucleosides that support RNase H cleavage positioned between external regions having one or more nucleosides, wherein the nucleosides comprising the internal region are chemically distinct from the nucleoside or nucleosides comprising the external regions. The internal region may be referred to as the "gap" and the external regions may be referred to as the "wings."

"Glucose" is a monosaccharide used by cells as a source of energy and metabolic intermediate. "Plasma glucose" refers to glucose present in the plasma.

"Glucose tolerance test" or "GTT" is a test to measure how well an animal breaks down glucose. Glucose is administered to the animal by injection or oral ingestion ("oral glucose tolerance test" or "OGTT") and blood samples are then drawn periodically and measured for the amount of glucose present.

"Hybridization" means annealing of oligonucleotides and/or nucleic acids. While not limited to a particular mechanism, the most common mechanism of hybridization involves hydrogen bonding, which may be Watson-Crick, Hoogsteen or reversed Hoogsteen hydrogen bonding, between complementary nucleobases. In certain embodiments, complementary nucleic acid molecules include, but are not limited to, an antisense compound and a nucleic acid target. In certain embodiments, complementary nucleic acid molecules include, but are not limited to, an oligonucleotide and a nucleic acid target.

"Immediately adjacent" means there are no intervening elements between the immediately adjacent elements of the same kind (e.g. no intervening nucleobases between the immediately adjacent nucleobases).

"Individual" means a human or non-human animal selected for treatment or therapy.

"Inhibiting the expression or activity" refers to a reduction or blockade of the expression or activity relative to the expression of activity in an untreated or control sample and does not necessarily indicate a total elimination of expression or activity.

"Insulin resistance" is defined as the condition in which normal amounts of insulin are inadequate to produce a normal insulin response from cells, e.g., fat, muscle and/or liver cells. Insulin resistance in fat cells results in hydrolysis of stored triglycerides, which elevates free fatty acids in the blood plasma. Insulin resistance in muscle reduces glucose uptake whereas insulin resistance in liver reduces glucose storage, with both effects serving to elevate blood glucose. High plasma levels of insulin and glucose due to insulin resistance often leads to metabolic syndrome and type 2 diabetes.

"Insulin sensitivity" is a measure of how effectively an individual processes glucose. An individual having high insulin sensitivity effectively processes glucose whereas an individual with low insulin sensitivity does not effectively process glucose.

"Internucleoside linkage" means a group or bond that forms a covalent linkage between adjacent nucleosides in an oligonucleotide. "Modified internucleoside linkage" means any internucleoside linkage other than a naturally occurring, phosphate internucleoside linkage. Non-phosphate linkages are referred to herein as modified internucleoside linkages.

"Intravenous administration" means administration into a vein.

"Lengthened oligonucleotides" are those that have one or more additional nucleosides relative to an oligonucleotide disclosed herein, e.g. a parent oligonucleotide.

"Linked nucleosides" means adjacent nucleosides linked together by an internucleoside linkage.

"Linker-nucleoside" means a nucleoside that links an oligonucleotide to a conjugate moiety. Linker-nucleosides are located within the conjugate linker of a compound. Linker-nucleosides are not considered part of the oligonucleotide portion of a compound even if they are contiguous with the oligonucleotide.

"KEAP1" means any nucleic acid or protein of KEAP1. "KEAP1 nucleic acid" means any nucleic acid encoding KEAP1. For example, in certain embodiments, a KEAP1 nucleic acid includes a DNA sequence encoding KEAP1, a RNA sequence transcribed from DNA encoding KEAP1 (including genomic DNA comprising introns and exons), including a non-protein encoding (i.e. non-coding) RNA sequence, and an mRNA sequence encoding KEAP1. "KEAP1 mRNA" means a mRNA encoding a KEAP1 protein. The target may be referred to in either upper or lower case.

"KEAP1 specific inhibitor" refers to any agent capable of specifically inhibiting KEAP1 expression or activity at the molecular level. For example, KEAP1-specific inhibitors include nucleic acids (including antisense compounds), peptides, antibodies, small molecules, and other agents capable of inhibiting the expression of KEAP1.

"Metabolic disorder" or "metabolic disease" refers to a condition characterized by an alteration or disturbance in metabolic function. "Metabolic" and "metabolism" are terms well known in the art and generally include the whole range of biochemical processes that occur within a living organism. Metabolic disorders include, but are not limited to, hyperglycemia, prediabetes, diabetes (type I and type 2), obesity, insulin resistance, NASH, NAFLD, metabolic syndrome and dyslipidemia due to type 2 diabetes.

"Metabolic syndrome" means a condition characterized by a clustering of lipid and non-lipid cardiovascular risk factors of metabolic origin. In certain embodiments, metabolic syndrome is identified by the presence of any 3 of the following factors: waist circumference of greater than 102 cm in men or greater than 88 cm in women; serum triglyceride of at least 150 mg/dL; HDL-C less than 40 mg/dL in men or less than 50 mg/dL in women; blood pressure of at least 130/85 mmHg; and fasting glucose of at least 110 mg/dL. These determinants can be readily measured in clinical practice (JAMA, 2001, 285: 2486-2497).

"Mismatch" or "non-complementary" means a nucleobase of a first oligonucleotide that is not complementary to the corresponding nucleobase of a second oligonucleotide or target nucleic acid when the first and second oligonucleotides are aligned. For example, nucleobases including but not limited to a universal nucleobase, inosine, and hypoxanthine, are capable of hybridizing with at least one nucleobase but are still mismatched or non-complementary with respect to nucleobase to which it hybridized. As another example, a nucleobase of a first oligonucleotide that is not capable of hybridizing to the corresponding nucleobase of a second oligonucleotide or target nucleic acid when the first and second oligonucleotides are aligned is a mismatch or non-complementary nucleobase.

"Modulating" refers to changing or adjusting a feature in a cell, tissue, organ or organism. For example, modulating a KEAP1 can mean to increase or decrease the level of the KEAP1 in a cell, tissue, organ or organism. A "modulator" effects the change in the cell, tissue, organ or organism. For example, a compound can be a modulator of KEAP1 that decreases the amount of KEAP1 in a cell, tissue, organ or organism.

"MOE" means methoxyethyl.

"Monomer" refers to a single unit of an oligomer. Monomers include, but are not limited to, nucleosides and nucleotides.

"Motif" means the pattern of unmodified and/or modified sugar moieties, nucleobases, and/or internucleoside linkages, in an oligonucleotide.

"Non-alcoholic fatty liver disease" or "NAFLD" means a condition characterized by fat accumulation in the liver that is not due to excessive alcohol use (for example, alcohol consumption of over 20 g/day). In certain embodiments, NAFLD is related to insulin resistance and metabolic syndrome. NAFLD encompasses a disease spectrum ranging from simple triglyceride accumulation in hepatocytes (hepatic steatosis) to hepatic steatosis with inflammation (steatohepatitis), fibrosis, and cirrhosis.

"Nonalcoholic steatohepatitis" (NASH) occurs from progression of NAFLD beyond deposition of triglycerides. A "second hit" capable of inducing necrosis, inflammation, and fibrosis is required for development of NASH. Candidates for the second-hit can be grouped into broad categories: factors causing an increase in oxidative stress and factors promoting expression of proinflammatory cytokines. It has been suggested that increased liver triglycerides lead to increased oxidative stress in hepatocytes of animals and humans, indicating a potential cause-and-effect relationship between hepatic triglyceride accumulation, oxidative stress, and the progression of hepatic steatosis to NASH (Browning and Horton, *J Clin Invest*, 2004, 114, 147-152). Hypertriglyceridemia and hyperfattyacidemia can cause triglyceride accumulation in peripheral tissues (Shimamura et al., *Biochem Biophys Res Commun,* 2004, 322, 1080-1085).

"Natural" or "naturally occurring" means found in nature.

"Non-bicyclic modified sugar" or "non-bicyclic modified sugar moiety" means a modified sugar moiety that comprises a modification, such as a substituent, that does not form a bridge between two atoms of the sugar to form a second ring.

"Nucleic acid" refers to molecules composed of monomeric nucleotides. A nucleic acid includes, but is not limited to, ribonucleic acids (RNA), deoxyribonucleic acids (DNA), single stranded nucleic acids, and double stranded nucleic acids.

"Nucleobase" means a heterocyclic moiety capable of pairing with a base of another nucleic acid. As used herein a "naturally occurring nucleobase" is adenine (A), thymine (T), cytosine (C), uracil (U), and guanine (G). A "modified nucleobase" is a naturally occurring nucleobase that is chemically modified. A "universal base" or "universal nucleobase" is a nucleobase other than a naturally occurring nucleobase and modified nucleobase, and is capable of pairing with any nucleobase.

"Nucleobase sequence" means the order of contiguous nucleobases in a nucleic acid or oligonucleotide independent of any sugar or internucleoside linkage.

"Nucleoside" means a compound comprising a nucleobase and a sugar moiety. The nucleobase and sugar moiety are each, independently, unmodified or modified. "Modified nucleoside" means a nucleoside comprising a modified nucleobase and/or a modified sugar moiety. Modified nucleosides include abasic nucleosides, which lack a nucleobase.

"Oligomeric compound" means a compound comprising a single oligonucleotide and optionally one or more additional features, such as a conjugate group or terminal group.

"Oligonucleotide" means a polymer of linked nucleosides each of which can be modified or unmodified, independent one from another. Unless otherwise indicated, oligonucleotides consist of 8-80 linked nucleosides. "Modified oligonucleotide" means an oligonucleotide, wherein at least one sugar, nucleobase, or internucleoside linkage is modified. "Unmodified oligonucleotide" means an oligonucleotide that does not comprise any sugar, nucleobase, or internucleoside modification.

"Parent oligonucleotide" means an oligonucleotide whose sequence is used as the basis of design for more oligonucleotides of similar sequence but with different lengths, motifs, and/or chemistries. The newly designed oligonucleotides may have the same or overlapping sequence as the parent oligonucleotide.

"Parenteral administration" means administration through injection or infusion. Parenteral administration includes subcutaneous administration, intravenous administration, intramuscular administration, intraarterial administration, intraperitoneal administration, or intracranial administration, e.g. intrathecal or intracerebroventricular administration.

"Pharmaceutically acceptable carrier or diluent" means any substance suitable for use in administering to an animal. For example, a pharmaceutically acceptable carrier can be a sterile aqueous solution, such as PBS or water-for-injection.

"Pharmaceutically acceptable salts" means physiologically and pharmaceutically acceptable salts of compounds, such as oligomeric compounds or oligonucleotides, i.e., salts that retain the desired biological activity of the parent compound and do not impart undesired toxicological effects thereto.

"Pharmaceutical agent" means a compound that provides a therapeutic benefit when administered to an individual.

"Pharmaceutical composition" means a mixture of substances suitable for administering to an individual. For example, a pharmaceutical composition may comprise one or more compounds or salt thereof and a sterile aqueous solution.

"Phosphorothioate linkage" means a modified phosphate linkage in which one of the non-bridging oxygen atoms is replaced with a sulfur atom. A phosphorothioate internucleoside linkage is a modified internucleoside linkage.

"Phosphorus moiety" means a group of atoms comprising a phosphorus atom. In certain embodiments, a phosphorus moiety comprises a mono-, di-, or tri-phosphate, or phosphorothioate.

"Portion" means a defined number of contiguous (i.e., linked) nucleobases of a nucleic acid. In certain embodiments, a portion is a defined number of contiguous nucleobases of a target nucleic acid. In certain embodiments, a portion is a defined number of contiguous nucleobases of an oligomeric compound.

"Prevent" refers to delaying or forestalling the onset, development or progression of a disease, disorder, or condition for a period of time from minutes to indefinitely.

"Prodrug" means a compound in a form outside the body which, when administered to an individual, is metabolized to another form within the body or cells thereof. In certain embodiments, the metabolized form is the active, or more active, form of the compound (e.g., drug). Typically conversion of a prodrug within the body is facilitated by the action of an enzyme(s) (e.g., endogenous or viral enzyme) or chemical(s) present in cells or tissues, and/or by physiologic conditions.

"Reduce" means to bring down to a smaller extent, size, amount, or number.

"RefSeq No." is a unique combination of letters and numbers assigned to a sequence to indicate the sequence is for a particular target transcript (e.g., target gene). Such sequence and information about the target gene (collectively, the gene record) can be found in a genetic sequence database. Genetic sequence databases include the NCBI Reference Sequence database, GenBank, the European Nucleotide Archive, and the DNA Data Bank of Japan (the latter three forming the International Nucleotide Sequence Database Collaboration or INSDC).

"Region" is defined as a portion of the target nucleic acid having at least one identifiable structure, function, or characteristic.

"RNAi compound" means an antisense compound that acts, at least in part, through RISC or Ago2, but not through RNase H, to modulate a target nucleic acid and/or protein encoded by a target nucleic acid. RNAi compounds include, but are not limited to double stranded siRNA, single stranded RNA (ssRNA), and microRNA, including microRNA mimics.

"Segments" are defined as smaller or sub-portions of regions within a nucleic acid.

"Side effects" means physiological disease and/or conditions attributable to a treatment other than the desired effects. In certain embodiments, side effects include injection site reactions, liver function test abnormalities, renal function abnormalities, liver toxicity, renal toxicity, central nervous system abnormalities, myopathies, and malaise. For example, increased aminotransferase levels in serum may indicate liver toxicity or liver function abnormality. For example, increased bilirubin may indicate liver toxicity or liver function abnormality.

"Single stranded" in reference to a compound means the compound has only one oligonucleotide. "Self-complementary" means an oligonucleotide that at least partially hybridizes to itself. A compound consisting of one oligonucleotide, wherein the oligonucleotide of the compound is self-complementary, is a single stranded compound. A single stranded compound may be capable of binding to a complementary compound to form a duplex.

"Sites," are defined as unique nucleobase positions within a target nucleic acid.

"Specifically hybridizable" refers to an oligonucleotide having a sufficient degree of complementarity between the oligonucleotide and a target nucleic acid to induce a desired effect, while exhibiting minimal or no effects on non-target nucleic acids. In certain embodiments, specific hybridization occurs under physiological conditions.

"Specifically inhibit" a target nucleic acid means to reduce or block expression of the target nucleic acid while exhibiting fewer, minimal, or no effects on non-target nucleic acids reduction and does not necessarily indicate a total elimination of the target nucleic acid's expression.

"Standard cell assay" means assay(s) described in the Examples and reasonable variations thereof.

"Standard in vivo experiment" means the procedure(s) described in the Example(s) and reasonable variations thereof.

"Sugar moiety" means an unmodified sugar moiety or a modified sugar moiety. "Unmodified sugar moiety" or "unmodified sugar" means a 2'-OH(H) furanosyl moiety, as found in RNA (an "unmodified RNA sugar moiety"), or a 2'-H(H) moiety, as found in DNA (an "unmodified DNA sugar moiety"). Unmodified sugar moieties have one hydrogen at each of the 1', 3', and 4' positions, an oxygen at the 3' position, and two hydrogens at the 5' position. "Modified sugar moiety" or "modified sugar" means a modified furanosyl sugar moiety or a sugar surrogate. "Modified furanosyl sugar moiety" means a furanosyl sugar comprising a non-hydrogen substituent in place of at least one hydrogen of an unmodified sugar moiety. In certain embodiments, a modified furanosyl sugar moiety is a 2'-substituted sugar moiety. Such modified furanosyl sugar moieties include bicyclic sugars and non-bicyclic sugars.

"Sugar surrogate" means a modified sugar moiety having other than a furanosyl moiety that can link a nucleobase to another group, such as an internucleoside linkage, conjugate group, or terminal group in an oligonucleotide. Modified nucleosides comprising sugar surrogates can be incorporated into one or more positions within an oligonucleotide and such oligonucleotides are capable of hybridizing to complementary oligomeric compounds or nucleic acids.

"Subcutaneous administration" means administration just below the skin.

"Target gene" refers to a gene encoding a target.

"Targeting" means specific hybridization of a compound that to a target nucleic acid in order to induce a desired effect.

"Target nucleic acid," "target RNA," "target RNA transcript" and "nucleic acid target" all mean a nucleic acid capable of being targeted by compounds described herein.

"Target region" means a portion of a target nucleic acid to which one or more compounds is targeted.

"Target segment" means the sequence of nucleotides of a target nucleic acid to which a compound described herein is targeted. "5' target site" refers to the 5'-most nucleotide of a target segment. "3' target site" refers to the 3'-most nucleotide of a target segment.

"Terminal group" means a chemical group or group of atoms that is covalently linked to a terminus of an oligonucleotide.

"Therapeutically effective amount" means an amount of a compound, pharmaceutical agent, or composition that provides a therapeutic benefit to an individual.

"Treat" refers to administering a compound or pharmaceutical composition to an animal in order to effect an alteration or improvement of a disease, disorder, or condition in the animal.

Certain Embodiments

Certain embodiments provide KEAP1 nucleic acids disclosed herein. In certain embodiments disclosed herein, KEAP1 has the human sequence as set forth in GenBank Accession No. NM_203500.1 (incorporated herein as SEQ ID NO: 1). In certain embodiments disclosed herein, KEAP1 has the human sequence as set forth in GenBank Accession No. NM_012289.3 (incorporated herein as SEQ ID NO: 2). In certain embodiments, KEAP1 has the human sequence as set forth in GenBank Accession No. NC_000019.10 nucleotides 10483001_10506000 (incorporated herein as SEQ ID NO: 3). In certain embodiments disclosed herein, KEAP1 has the mouse sequence as set forth in GenBank Accession No. NM_001110305.1 (incorporated herein as SEQ ID NO: 4). In certain embodiments disclosed herein, KEAP1 has the mouse sequence as set forth in GenBank Accession No. NM_016679.4 (incorporated herein as SEQ ID NO: 5). In certain embodiments, KEAP1 has the mouse sequence as set forth in GenBank Accession No. NC_000075.6 nucleotides 21227001_21242000 (incorporated herein as SEQ ID NO: 6).

Certain embodiments provide methods, compounds, and compositions for modulating a disease related to oxidative stress, or a symptom thereof, in an animal by administering a therapeutically effective amount of a compound or composition to the animal, wherein the compound or composition comprises a KEAP1 modulator. Modulation of a KEAP1 can lead to a decrease in KEAP1 level or expression in order to treat, prevent, ameliorate or delay oxidative stress or a disease, disorder or condition related to oxidative stress, or a symptom thereof. In certain embodiments, the KEAP1 modulator is a KEAP1 specific inhibitor. In certain embodiments, KEAP1 specific inhibitors are nucleic acids (including antisense compounds), peptides, antibodies, small molecules, and other agents capable of inhibiting the expression of the KEAP1.

Certain embodiments disclosed herein provide compounds or compositions comprising a KEAP1 modulator. In certain embodiments, the KEAP1 modulator is a KEAP1 specific inhibitor. In certain embodiments, the KEAP1 specific inhibitor is a nucleic acid, polypeptide, antibody, small molecules, or other agent capable of inhibiting the expression of KEAP1. In certain embodiments, the nucleic acid is a compound or composition targeting KEAP1. In certain embodiments, the compound or composition comprises deoxyribonucleotides. In certain embodiments, the compound or composition comprises ribonucleotides. In certain embodiments, the compound or composition is single stranded. In certain embodiments, the compound or composition is double stranded. In certain embodiments, the compound or composition targeting KEAP1 comprises an oligonucleotide. In certain embodiments, the oligonucleotide is single stranded. In certain embodiments, the oligonucleotide is double stranded. In certain embodiments, the oligonucleotide is a modified oligonucleotide. In certain embodiments, the modified oligonucleotide is single stranded. In certain embodiments, the modified oligonucleotide is double stranded. In any of the foregoing embodiments, the compound can be an antisense compound or oligomeric compound.

In any of the foregoing embodiments, the compound or composition can consist of 8 to 80, 10 to 30, 12 to 50, 13 to 30, 13 to 50, 14 to 30, 14 to 50, 15 to 30, 15 to 50, 16 to 30, 16 to 50, 17 to 30, 17 to 50, 18 to 22, 18 to 24, 18 to 30, 18 to 50, 19 to 22, 19 to 30, 19 to 50, or 20 to 30 linked nucleosides. In certain embodiments, these compounds are oligonucleotides.

Certain embodiments disclosed herein provide a compound or composition comprising a modified oligonucleotide that is 10 to 30 linked nucleosides in length targeted to a KEAP1. The KEAP1 target can have a nucleobase sequence selected from any one of SEQ ID NOs: 1-6. In certain embodiments, the nucleobase sequence of the modified oligonucleotide is at least 70%, 75%, 80%, 85%, 90%, 95% or 100% complementary to the nucleobase sequences recited in any one of SEQ ID NOs: 1-6 as measured over the entirety of the modified oligonucleotide. In certain embodiments, the modified oligonucleotide comprises a nucleobase sequence comprising a portion of at least 8, at least 9, at least 10, at least 11, at least 12, at least 13, at least 14, at least 15, or 16 contiguous nucleobases complementary to an equal length portion of SEQ ID NO: 1-6.

Certain embodiments provide a compound comprising a modified oligonucleotide 8 to 80 linked nucleosides in length and having a nucleobase sequence comprising the nucleobase sequence of any one of SEQ ID NOs: 7-9. In certain embodiments, the compound is an antisense compound or oligomeric compound. In certain embodiments, the compound is single stranded. In certain embodiments, the compound is double stranded. In certain embodiments, the modified oligonucleotide consists of 12 to 30 linked nucleosides.

Certain embodiments provide a compound comprising a modified oligonucleotide consisting of the nucleobase sequence of any one of SEQ ID NOs: 7-9. In certain embodiments, the compound is an antisense compound or oligomeric compound. In certain embodiments, the compound is single stranded. In certain embodiments, the compound is double stranded.

In certain embodiments, the modified oligonucleotide consists of 10 to 50, 10 to 30, 12 to 30, 13 to 24, 14 to 24, 15 to 30, 15 to 24, 15 to 20, 15 to 18, 16 to 30, 16 to 24, 16 to 20, 16 to 18, 18 to 24 or 19 to 22 linked nucleosides. In certain embodiments, the modified oligonucleotide consists of 8, 9, 10, 11, 12, 13, 14, 15, 16, 17, 18, 19, 20, 21, 22, 23, 24, 25, 26, 27, 28, 29 or 30 linked nucleosides or a range defined by any two of these values.

In certain embodiments, at least one internucleoside linkage of said modified oligonucleotide is a modified internucleoside linkage. In certain embodiments, the at least one internucleoside linkage is a phosphorothioate internucleoside linkage. In certain embodiments, each internucleoside linkage is a phosphorothioate internucleoside linkage.

In certain embodiments, any of the foregoing oligonucleotides comprises at least one modified sugar. In certain embodiments, at least one modified sugar comprises a 2'-O-methoxyethyl group. In certain embodiments, at least one modified sugar is a bicyclic sugar, such as a 4'-CH(CH$_3$)—O-2' group, a 4'-CH$_2$—O-2' group, or a 4'-(CH$_2$)$_2$—O-2' group.

In certain embodiments, at least one nucleoside of said modified oligonucleotide comprises a modified nucleobase. In certain embodiments, the at least one modified nucleobase is a 5-methylcytosine. In certain embodiments, each cytosine nucleobase is a 5-methylcytosine.

Certain embodiments disclosed herein provide a compound or composition comprising a modified oligonucleotide with: a) a gap segment consisting of linked deoxynucleosides; b) a 5' wing segment consisting of linked nucleosides; and c) a 3' wing segment consisting of linked nucleosides. The gap segment is positioned between the 5' wing segment and the 3' wing segment and each nucleoside of each wing segment comprises a modified sugar. In certain embodiments, the modified sugar comprises a bicyclic sugar or 2'-O-methoxyethyl group. In certain embodiments, the bicyclic sugar comprises a 4'-CH(CH$_3$)—O-2' group, a 4'-CH$_2$—O-2' group or a 4'-(CH$_2$)$_2$—O-2' group. In certain embodiments, at least one internucleoside linkage is a phosphorothioate linkage. In certain embodiments, each internucleoside linkage is a phosphorothioate linkage. In certain embodiments, at least one cytosine is a 5-methylcytosine. In certain embodiments, each cytosine is a 5-methylcytosine.

Certain embodiments disclosed herein provide a compound or composition comprising a modified oligonucleotide 16 nucleobases in length with: a) a gap segment consisting of ten linked deoxynucleosides; b) a 5' wing segment consisting of three linked nucleosides; and c) a 3' wing segment consisting of three linked nucleosides. The gap segment is positioned between the 5' wing segment and the 3' wing segment and each nucleoside of each wing segment comprises a modified sugar. In certain embodiments, the modified sugar comprises a bicyclic sugar or 2'-O-methoxyethyl group. In certain embodiments, the bicyclic sugar comprises a 4'-CH(CH$_3$)—O-2' group, a 4'-CH$_2$—O-2' group or a 4'-(CH$_2$)$_2$—O-2' group. In certain embodiments, at least one internucleoside linkage is a phosphorothioate linkage. In certain embodiments, each internucleoside linkage is a phosphorothioate linkage. In certain embodiments, at least one cytosine is a 5-methylcytosine. In certain embodiments, each cytosine is a 5-methylcytosine.

Certain embodiments disclosed herein provide a compound or composition comprising a modified oligonucleotide 20 nucleobases in length with: a) a gap segment consisting of ten linked deoxynucleosides; b) a 5' wing segment consisting of five linked nucleosides; and c) a 3' wing segment consisting of five linked nucleosides. The gap segment is positioned between the 5' wing segment and the 3' wing segment and each nucleoside of each wing segment comprises a modified sugar. In certain embodiments, the modified sugar comprises a bicyclic sugar or 2'-O-methoxyethyl group. In certain embodiments, the bicyclic sugar comprises a 4'-CH(CH$_3$)—O-2' group, a 4'-CH$_2$—O-2' group or a 4'-(CH$_2$)$_2$—O-2' group. In certain embodiments, at least one internucleoside linkage is a phosphorothioate linkage. In certain embodiments, each internucleoside linkage is a phosphorothioate linkage. In certain embodiments, at least one cytosine is a 5-methylcytosine. In certain embodiments, each cytosine is a 5-methylcytosine.

In certain embodiments, the compounds or compositions disclosed herein further comprise a conjugate group. In certain embodiments, the conjugate group is a carbohydrate group. In certain embodiments, the conjugate group is a GalNAc group.

In certain embodiments, the compounds or compositions disclosed herein comprise a salt of the compound. In certain embodiments, the compounds or compositions disclosed herein comprise a salt of the modified oligonucleotide. In certain embodiments, the salt is a sodium salt. In certain embodiments, the salt is a potassium salt.

In certain embodiments, the compounds or compositions disclosed herein further comprise a pharmaceutically acceptable carrier or diluent.

Certain embodiments disclosed herein provide a method of reducing KEAP1 expression in an animal comprising administering to the animal a compound or composition comprising a KEAP1 specific inhibitor. Certain embodiments disclosed herein provide use of a KEAP1 specific inhibitor for reducing KEAP1 expression in an animal. In certain embodiments, the KEAP1 specific inhibitor is a nucleic acid, peptide, antibody, small molecule or other agent capable of inhibiting the expression of KEAP1. In certain embodiments, the KEAP1 specific inhibitor comprises a compound or composition described herein. In certain embodiments, the compound or composition comprises an antisense compound or an oligomeric compound. In certain embodiments, the compound or composition comprises a modified oligonucleotide. In certain embodiments, the modified oligonucleotide consists of 10 to 30 linked nucleosides. In certain embodiments, the modified oligonucleotide consists of 16 linked nucleosides. In certain embodiments, the modified oligonucleotide consists of 20 linked nucleosides.

Certain embodiments disclosed herein provide a method of reducing oxidative stress in an animal comprising administering to the animal a therapeutically effective amount of a compound or composition comprising a KEAP1 specific inhibitor. Certain embodiments disclosed herein provide use of a KEAP1 specific inhibitor for reducing oxidative stress in an animal. In certain embodiments, the KEAP1 specific inhibitor is a nucleic acid, peptide, antibody, small molecule or other agent capable of inhibiting the expression of KEAP1. In certain embodiments, the KEAP1 specific inhibitor comprises a compound or composition described herein. In certain embodiments, the compound or composition comprises an antisense compound or an oligomeric compound. In certain embodiments, the compound or composition comprises a modified oligonucleotide. In certain embodiments, the modified oligonucleotide consists of 10 to 30 linked nucleosides. In certain embodiments, the modified oligonucleotide consists of 16 linked nucleosides. In certain embodiments, the modified oligonucleotide consists of 20 linked nucleosides.

Certain embodiments disclosed herein provide a method of treating, preventing, delaying or ameliorating a disease, disorder or condition related to oxidative stress in an animal comprising administering to the animal a therapeutically effective amount of a compound or composition comprising a KEAP1 specific inhibitor. Certain embodiments disclosed herein provide use of a KEAP1 specific inhibitor for treating, preventing, delaying or ameliorating a disease, disorder or condition related to oxidative stress. In certain embodiments, the KEAP1 specific inhibitor is a nucleic acid, peptide, antibody, small molecule or other agent capable of inhibiting the expression of KEAP1. In certain embodiments, the KEAP1 specific inhibitor comprises a compound or composition described herein. In certain embodiments, the compound or composition comprises an antisense compound or an oligomeric compound. In certain embodiments, the compound or composition comprises a modified oligonucleotide. In certain embodiments, the modified oligonucleotide consists of 10 to 30 linked nucleosides. In certain embodiments, the modified oligonucleotide consists of 16 linked nucleosides. In certain embodiments, the modified oligonucleotide consists of 20 linked nucleosides.

Certain embodiments disclosed herein provide a method of treating an animal at risk for a disease, disorder or condition related to oxidative stress comprising administering to the animal a therapeutically effective amount of a compound or composition comprising a KEAP1 specific inhibitor. Certain embodiments disclosed herein provide use of a KEAP1 specific inhibitor for treating an animal at risk for a disease, disorder or condition related to oxidative stress. In certain embodiments, the KEAP1 specific inhibitor is a nucleic acid, peptide, antibody, small molecule or other agent capable of inhibiting the expression of KEAP1. In certain embodiments, the KEAP1 specific inhibitor comprises a compound or composition described herein. In certain embodiments, the compound or composition comprises an antisense compound or an oligomeric compound. In certain embodiments, the compound or composition comprises a modified oligonucleotide. In certain embodiments, the modified oligonucleotide consists of 10 to 30 linked nucleosides. In certain embodiments, the modified oligonucleotide consists of 16 linked nucleosides. In certain embodiments, the modified oligonucleotide consists of 20 linked nucleosides.

In certain embodiments the disease, disorder or condition related to oxidative stress is a metabolic disease, disorder or condition. In certain embodiments the metabolic disease, disorder or condition is metabolic syndrome, type 2 diabetes, diabetic nephropathy, diabetic cardiomyopathy and/or insulin resistance. In certain embodiments the disease, disorder or condition related to oxidative stress is a fatty liver disease, disorder or condition. In certain embodiments the fatty liver disease, disorder or condition is hepatic steatosis, NASH and/or NAFLD. In certain embodiments the disease, disorder or condition related to oxidative stress is an inflammatory disease. In certain embodiments the inflammatory disease, disorder or condition is asthma, chronic obstructive pulmonary disease (COPD), cystic fibrosis (CF) and/or airway hyperresponsiveness. In certain embodiments the disease, disorder or condition related to oxidative stress is an allergic disease, disorder or condition. In certain embodiments the allergic disease, disorder or condition is asthma. In certain embodiments the disease, disorder or condition related to oxidative stress is a fibrotic disease, disorder or condition. In certain embodiments, the fibrotic disease, disorder or condition is pulmonary fibrosis, renal fibrosis, cystic fibrosis, or hepatic fibrosis. In certain embodiments the disease, disorder or condition related to oxidative stress is cancer, age related macular degeneration, atherosclerosis, hyperlipidemia, and neurologic disorders.

Certain embodiments disclosed herein provide a method of treating, preventing, delaying or ameliorating organ damage in an animal comprising administering to the animal a therapeutically effective amount of a compound or composition comprising a KEAP1 specific inhibitor. Certain embodiments disclosed herein provide use of a KEAP1 specific inhibitor for treating, preventing, delaying or ameliorating a disease, disorder or condition related to organ damage. In certain embodiments, the organ damage is due to fibrosis. In certain embodiments, the fibrotic organ is lung or liver. In certain embodiments, the fibrotic disease, disorder or condition is hepatic fibrosis, NAFLD, NASH, pulmonary fibrosis, cystic fibrosis, or hepatic fibrosis. In certain embodiments, the KEAP1 specific inhibitor is a nucleic acid, peptide, antibody, small molecule or other agent capable of inhibiting the expression of KEAP1. In certain embodiments, the KEAP1 specific inhibitor comprises a compound or composition described herein. In certain embodiments, the compound or composition comprises an antisense compound or an oligomeric compound. In certain embodiments, the compound or composition comprises a modified oligonucleotide. In certain embodiments, the modified oligonucleotide consists of 10 to 30 linked nucleosides. In certain embodiments, the modified oligonucleotide consists of 16 linked nucleosides. In certain embodiments, the modified oligonucleotide consists of 20 linked nucleosides Certain embodiments provide methods of using the compounds and compositions described herein for inhibiting a KEAP1 expression. In certain embodiments, the compounds or compositions inhibit KEAP1 by at least 5%, at least 10%, at least 20%, at least 30%, at least 35%, at least 40%, at least 45%, at least 50%, at least 55%, at least 60%, at least 65%, at least 70%, at least 75%, at least 80%, at least 85%, or at least 90%.

Certain embodiments provide methods of using the compounds and compositions described herein for use in therapy. In certain embodiments, the therapy is used in treating, preventing, delaying the onset or slowing progression of a disease, disorder or condition related to KEAP1. In certain embodiments, the KEAP1 disease, disorder or condition is related to oxidative stress. In certain embodiments the disease, disorder or condition related to oxidative stress is a metabolic disease, disorder or condition. In certain embodiments the metabolic disease, disorder or condition is metabolic syndrome, type 2 diabetes, diabetic nephropathy, diabetic cardiomyopathy and/or insulin resistance. In certain embodiments the disease, disorder or condition related to oxidative stress is a fatty liver disease, disorder or condition. In certain embodiments the fatty liver disease, disorder or condition is hepatic steatosis, NASH and/or NAFLD. In certain embodiments the disease, disorder or condition related to oxidative stress is an inflammatory disease. In certain embodiments the inflammatory disease, disorder or condition is asthma, chronic obstructive pulmonary disease (COPD), cystic fibrosis (CF) and/or airway hyperresponsiveness. In certain embodiments the disease, disorder or condition related to oxidative stress is an allergic disease, disorder or condition. In certain embodiments the allergic disease, disorder or condition is asthma. In certain embodiments the disease, disorder or condition related to oxidative stress is a fibrotic disease, disorder or condition. In certain embodiments, the fibrotic disease, disorder or condition is pulmonary fibrosis, renal fibrosis, cystic fibrosis, or hepatic fibrosis. In certain embodiments the disease, disorder or condition related to oxidative stress is cancer, age related macular degeneration, atherosclerosis, hyperlipidemia, and neurologic disorders.

Certain embodiments provide methods of using the compounds and compositions described herein for use in the manufacture of a medicament. In certain embodiments, the medicament is used in treating, preventing, delaying the onset or slowing progression of a disease, disorder or condition related to KEAP1. In certain embodiments, the disease is related to oxidative stress. In certain embodiments the disease, disorder or condition related to oxidative stress is a metabolic disease, disorder or condition. In certain embodiments the metabolic disease, disorder or condition is metabolic syndrome, type 2 diabetes, diabetic nephropathy, diabetic cardiomyopathy and/or insulin resistance. In certain embodiments the disease, disorder or condition related to oxidative stress is a fatty liver disease, disorder or condition. In certain embodiments the fatty liver disease, disorder or condition is hepatic steatosis, NASH and/or NAFLD. In certain embodiments the disease, disorder or condition related to oxidative stress is an inflammatory disease. In certain embodiments the inflammatory disease, disorder or condition is asthma, chronic obstructive pulmonary disease (COPD), cystic fibrosis (CF) and/or airway hyperresponsiveness. In certain embodiments the disease, disorder or condition related to oxidative stress is an allergic disease, disorder or condition. In certain embodiments the allergic disease, disorder or condition is asthma. In certain embodiments the disease, disorder or condition related to oxidative stress is a fibrotic disease, disorder or condition. In certain embodiments, the fibrotic disease, disorder or condition is pulmonary fibrosis, renal fibrosis, cystic fibrosis, or hepatic fibrosis. In certain embodiments the disease, disorder or condition related to oxidative stress is cancer, age related macular degeneration, atherosclerosis, hyperlipidemia, and neurologic disorders.

In certain embodiments, the animal is a human.

In any of the foregoing methods or uses, the compound or composition can be administered parenterally. For example, in certain embodiments the compound or composition can be administered through injection or infusion. Parenteral administration includes subcutaneous administration, intravenous administration, intramuscular administration, intraarterial administration, intraperitoneal administration, or intracranial administration.

In certain embodiments, the compounds or compositions disclosed herein are designated as a first agent and the methods or uses disclosed herein further comprise administering a second agent. In certain embodiments, the first agent and the second agent are co-administered. In certain embodiments the first agent and the second agent are co-administered sequentially or concomitantly.

Certain embodiments provide a method of using a compound or composition disclosed herein to reduce a biomarker of oxidative stress by at least 5%, at least 10%, at least 20%, at least 30%, at least 35%, at least 40%, at least 45% or at least 50%. In certain embodiments, the biomarker reduced is liver triglyceride, liver cholesterol, liver ballooning degeneration, fibrosis (e.g., fibrosis in an organ such as the liver or lung), body weight, organ weight, hyperinsulinemia, fasting hyperleptinemia, liver hydroxyproline, collagen (e.g., Col1a2), liver glutathione (GSH), asthma, airway hyperresponsiveness (AHR), eosinophil infiltration into the lungs, mucus production (e.g., as measured by expression of GOBS, SPDEF and/or MUC5B) and inflammation (e.g., as measured by macrophage-restricted F4/80). In certain embodiments, the biomarker of fibrosis is hydroxyproline or collagen (e.g., Col1a2). Certain embodiments provide a method of using a compound or composition disclosed herein to increase an antioxidant biomarker by at least 5%, at least 10%, at least 20%, at least 30%, at least 35%, at least 40%, at least 45% or at least 50%. In certain embodiments, the biomarker increased is insulin sensitivity, glucose tolerance, NRF2, PGAM5, Glutathione S-transferases (GSTs e.g., GSTA1), GCLM, NQO1, NQO2, HO-1.

Certain embodiments provided herein relate to methods of using the KEAP1 targeting compounds described herein in combination with one or more agent or therapy to treat oxidative stress or a disease, disorder or condition related to oxidative stress. In certain embodiments, the agents are antioxidants. In certain embodiments, the agents are anti-inflammatory drugs. In certain embodiments, the agents are anti-allergy drugs. In certain embodiments, the agents are insulin sensitizing drugs. In certain embodiments, the agents are glucose absorption inhibitors. In certain embodiments, the agents are glucose-lowering drugs. In some embodiments, the drugs include, but are not limited to: a PPAR agonist (gamma, dual, or pan), a dipeptidyl peptidase (IV) inhibitor, a GLP-1 analog, insulin or an insulin analog, an insulin secretagogue, a SGLT2 inhibitor, a human amylin analog, a biguanide, or an alpha-glucosidase inhibitor. In certain embodiments, the drug is metformin, sulfonylurea, or rosiglitazone. Agents or therapies can be administered concomitantly or sequentially to an animal.

In certain embodiments, provided is a kit for treating, preventing, or ameliorating an oxidative stress related disease and/or condition, disease, disorder or condition, wherein the kit comprises: (i) a KEAP1 specific inhibitor as described herein; and optionally (ii) an additional agent or therapy as described herein.

A kit of the present invention may further include instructions for using the kit to treat, prevent, or ameliorate an oxidative stress related disease, disorder or condition as described herein.

Certain Indications

Certain embodiments provided herein relate to methods of inhibiting KEAP1 expression, which can be useful for treating, preventing, or ameliorating a disease, disorder or condition associated with a KEAP1 in an individual, by administration of a compound that specifically targets KEAP1. An example of a disease, disorder or condition associated with KEAP1 is oxidative stress.

Certain embodiments provided herein relate to methods of reducing, treating or ameliorating oxidative stress in an animal by administration of a compound that specifically targets KEAP1 to the animal suffering from oxidative stress.

Certain embodiments provided herein relate to methods of preventing oxidative stress in an animal by administration of a compound that specifically targets KEAP1 to an animal suffering prone to oxidative stress.

Certain embodiments provided herein relate to methods of reducing oxidative stress in an animal, which can be useful for treating, preventing, or ameliorating a disease, disorder or condition associated with oxidative stress, by administration of a compound that specifically targets KEAP1 to the animal suffering from the disease, disorder or condition associated with oxidative stress.

In certain embodiments the disease, disorder or condition related to oxidative stress is a metabolic disease, disorder or condition. In certain embodiments the metabolic disease, disorder or condition is metabolic syndrome, type 2 diabetes, diabetic nephropathy, diabetic cardiomyopathy and/or insulin resistance.

In certain embodiments the disease, disorder or condition related to oxidative stress is a fatty liver disease, disorder or condition. In certain embodiments the fatty liver disease, disorder or condition is hepatic steatosis, NASH and/or NAFLD.

In certain embodiments the disease, disorder or condition related to oxidative stress is an inflammatory disease. In certain embodiments the inflammatory disease, disorder or condition is asthma, chronic obstructive pulmonary disease (COPD), fibrosis (e.g., hepatic fibrosis, cystic fibrosis (CF), renal fibrosis) and/or airway hyperresponsiveness.

In certain embodiments the disease, disorder or condition related to oxidative stress is an allergic disease, disorder or condition. In certain embodiments the allergic disease, disorder or condition is asthma.

In certain embodiments the disease, disorder or condition related to oxidative stress is a fibrotic disease, disorder or condition. In certain embodiments, the fibrotic disease, disorder or condition is pulmonary fibrosis, renal fibrosis, cystic fibrosis, or hepatic fibrosis.

In certain embodiments the disease, disorder or condition related to oxidative stress is cancer, age related macular degeneration, atherosclerosis, hyperlipidemia, and neurologic disorders.

In certain embodiments, the compound targeting KEAP1 is a KEAP1 specific inhibitor. In certain embodiments, the compound is an antisense compound or an oligomeric compound targeted to a KEAP1. In certain embodiments, the compound comprises an oligonucleotide targeted to a KEAP1 nucleic acid. In certain embodiments, the compound comprises a modified oligonucleotide targeted to a KEAP1 nucleic acid. In certain embodiments disclosed herein, the KEAP1 target has the human or murine sequences as recited in any one of SEQ ID NOs: 1-6.

Certain Compounds

In certain embodiments, compounds described herein are antisense compounds. In certain embodiments, the antisense compound comprises or consists of an oligomeric compound. In certain embodiments, the oligomeric compound comprises a modified oligonucleotide. In certain embodiments, the modified oligonucleotide has a nucleobase sequence complementary to that of a target nucleic acid.

In certain embodiments, a compound described herein comprises or consists of a modified oligonucleotide. In certain embodiments, the modified oligonucleotide has a nucleobase sequence complementary to that of a target nucleic acid.

In certain embodiments, a compound or antisense compound is single stranded. Such a single stranded compound or antisense compound comprises or consists of an oligomeric compound. In certain embodiments, such an oligomeric compound comprises or consists of an oligonucleotide and optionally a conjugate group. In certain embodiments, the oligonucleotide is an antisense oligonucleotide. In certain embodiments, the oligonucleotide is modified. In certain embodiments, the oligonucleotide of a single stranded antisense compound or oligomeric compound comprises a self-complementary nucleobase sequence.

In certain embodiments, compounds are double stranded. Such double stranded compounds comprise a first modified oligonucleotide having a region complementary to a target nucleic acid and a second modified oligonucleotide having a region complementary to the first modified oligonucleotide. In certain embodiments, the modified oligonucleotide is an RNA oligonucleotide. In such embodiments, the thymine nucleobase in the modified oligonucleotide is replaced by a uracil nucleobase. In certain embodiments, compound comprises a conjugate group. In certain embodiments, one of the modified oligonucleotides is conjugated. In certain embodiments, both the modified oligonucleotides are conjugated. In certain embodiments, the first modified oligonucleotide is conjugated. In certain embodiments, the second modified oligonucleotide is conjugated. In certain embodiments, each modified oligonucleotide is 12-30 linked nucleosides in length.

In certain embodiments, compounds are double stranded. Such double stranded compounds comprise a first oligomeric compound having a region complementary to a target nucleic acid and a second oligomeric compound having a region complementary to the first oligomeric compound. The first oligomeric compound of such double stranded compounds typically comprises or consists of a modified oligonucleotide and optionally a conjugate group. The oligonucleotide of the second oligomeric compound of such double stranded compound may be modified or unmodified. Either or both oligomeric compounds of a double stranded compound may comprise a conjugate group. The oligomeric compounds of double stranded compounds may include non-complementary overhanging nucleosides.

Examples of single stranded and double stranded compounds include but are not limited to oligonucleotides, siRNAs, microRNA targeting oligonucleotides, and single stranded RNAi compounds, such as small hairpin RNAs (shRNAs), single stranded siRNAs (ssRNAs), and microRNA mimics.

In certain embodiments, a compound described herein has a nucleobase sequence that, when written in the 5' to 3' direction, comprises the reverse complement of the target segment of a target nucleic acid to which it is targeted.

In certain embodiments, a compound described herein comprises an oligonucleotide 10 to 30 linked subunits in length. In certain embodiments, compound described herein comprises an oligonucleotide is 12 to 30 linked subunits in length. In certain embodiments, compound described herein comprises an oligonucleotide is 12 to 22 linked subunits in length. In certain embodiments, compound described herein comprises an oligonucleotide is 14 to 30 linked subunits in length. In certain embodiments, compound described herein comprises an oligonucleotide is 14 to 20 linked subunits in length. In certain embodiments, compound described herein comprises an oligonucleotide is 15 to 30 linked subunits in length. In certain embodiments, compound described herein comprises an oligonucleotide is 15 to 20 linked subunits in length. In certain embodiments, compound described herein comprises an oligonucleotide is 16 to 30 linked subunits in length. In certain embodiments, compound described herein comprises an oligonucleotide is 16 to 20 linked subunits in length. In certain embodiments, compound described herein comprises an oligonucleotide is 17 to 30 linked subunits in length. In certain embodiments, compound described herein comprises an oligonucleotide is 17 to 20 linked subunits in length. In certain embodiments, compound described herein comprises an oligonucleotide is 18 to 30 linked subunits in length. In certain embodiments, compound described herein comprises an oligonucleotide is 18 to 21 linked subunits in length. In certain embodiments, compound described herein comprises an oligonucleotide is 18 to 20 linked subunits in length. In certain embodiments, compound described herein comprises an oligonucleotide is 20 to 30 linked subunits in length. In other words, such oligonucleotides are from 12 to 30 linked subunits, 14 to 30 linked subunits, 14 to 20 subunits, 15 to 30 subunits, 15 to 20 subunits, 16 to 30 subunits, 16 to 20 subunits, 17 to 30 subunits, 17 to 20 subunits, 18 to 30 subunits, 18 to 20 subunits, 18 to 21 subunits, 20 to 30 subunits, or 12 to 22 linked subunits, respectively. In certain embodiments, a compound described herein comprises an oligonucleotide 14 linked subunits in length. In certain embodiments, a compound described herein comprises an oligonucleotide 16 linked subunits in length. In certain embodiments, a compound described herein comprises an oligonucleotide 17 linked subunits in length. In certain embodiments, compound described herein comprises an oligonucleotide 18 linked subunits in length. In certain embodiments, a compound described herein comprises an oligonucleotide 19 linked subunits in length. In certain embodiments, a compound described herein comprises an oligonucleotide 20 linked subunits in length. In other embodiments, a compound described herein comprises an oligonucleotide 8 to 80, 12 to 50, 13 to 30, 13 to 50, 14 to 30, 14 to 50, 15 to 30, 15 to 50, 16 to 30, 16 to 50, 17 to 30, 17 to 50, 18 to 22, 18 to 24, 18 to 30, 18 to 50, 19 to 22, 19 to 30, 19 to 50, or 20 to 30 linked subunits. In certain such embodiments, the compound described herein comprises an oligonucleotide 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 linked subunits in length, or a range defined by any two of the above values. In some embodiments the linked subunits are nucleotides, nucleosides, or nucleobases.

In certain embodiments, the compound may further comprise additional features or elements, such as a conjugate group, that are attached to the oligonucleotide. In certain embodiments, such compounds are antisense compounds. In certain embodiments, such compounds are oligomeric compounds. In embodiments where a conjugate group comprises a nucleoside (i.e. a nucleoside that links the conjugate group to the oligonucleotide), the nucleoside of the conjugate group is not counted in the length of the oligonucleotide.

In certain embodiments, compounds may be shortened or truncated. For example, a single subunit may be deleted from the 5' end (5' truncation), or alternatively from the 3' end (3' truncation). A shortened or truncated compound targeted to a KEAP1 nucleic acid may have two subunits deleted from the 5' end, or alternatively may have two subunits deleted from the 3' end, of the compound. Alternatively, the deleted nucleosides may be dispersed throughout the compound.

When a single additional subunit is present in a lengthened compound, the additional subunit may be located at the 5' or 3' end of the compound. When two or more additional subunits are present, the added subunits may be adjacent to each other, for example, in a compound having two subunits added to the 5' end (5' addition), or alternatively to the 3' end (3' addition), of the compound. Alternatively, the added subunits may be dispersed throughout the compound.

It is possible to increase or decrease the length of a compound, such as an oligonucleotide, and/or introduce mismatch bases without eliminating activity (Woolf et al. (Proc. Natl. Acad. Sci. USA 89:7305-7309, 1992; Gautschi et al. *J. Natl. Cancer Inst.* 93:463-471, March 2001; Maher and Dolnick *Nuc. Acid. Res.* 16:3341-3358, 1988). However, seemingly small changes in oligonucleotide sequence, chemistry and motif can make large differences in one or more of the many properties required for clinical development (Seth et al. *J. Med. Chem.* 2009, 52, 10; Egli et al. *J. Am. Chem. Soc.* 2011, 133, 16642).

In certain embodiments, compounds described herein are interfering RNA compounds (RNAi), which include double stranded RNA compounds (also referred to as short-interfering RNA or siRNA) and single stranded RNAi compounds (or ssRNA). Such compounds work at least in part through the RISC pathway to degrade and/or sequester a target nucleic acid (thus, include microRNA/microRNA-mimic compounds). As used herein, the term siRNA is meant to be equivalent to other terms used to describe nucleic acid molecules that are capable of mediating sequence specific RNAi, for example short interfering RNA (siRNA), double stranded RNA (dsRNA), micro-RNA (miRNA), short hairpin RNA (shRNA), short interfering oligonucleotide, short interfering nucleic acid, short interfering modified oligonucleotide, chemically modified siRNA, post-transcriptional gene silencing RNA (ptgsRNA), and others. In addition, as used herein, the term RNAi is meant to be equivalent to other terms used to describe sequence specific RNA interference, such as post transcriptional gene silencing, translational inhibition, or epigenetics.

In certain embodiments, a double stranded compound described herein can comprise any of the oligonucleotide sequences targeted to a KEAP1 described herein. In certain embodiments, a double stranded compound comprises a first strand comprising sequence complementary to any one of SEQ ID NOs: 1-6 and a second strand.

In certain embodiments, a double stranded compound comprises a first strand comprising the nucleobase sequence complementary to any one of SEQ ID NOs: 1-6 and a second strand. In certain embodiments, the double stranded compound comprises ribonucleotides in which the first strand has uracil (U) in place of thymine (T) and is complementary to any one of SEQ ID NOs: 1-6. In certain embodiments, a double stranded compound comprises (i) a first strand comprising a nucleobase sequence complementary to the site on a KEAP1 of any of SEQ ID NOs: 1-6, and (ii) a second strand. In certain embodiments, the double stranded compound comprises one or more modified nucleotides in which the 2' position in the sugar contains a halogen (such as fluorine group; 2'-F) or contains an alkoxy group (such as a methoxy group; 2'-OMe). In certain embodiments, the double stranded compound comprises at least one 2'-F sugar modification and at least one 2'-OMe sugar modification. In certain embodiments, the at least one 2'-F sugar modification and at least one 2'-OMe sugar modification are arranged in an alternating pattern for at least 2, 3, 4, 5, 6, 7, 8, 9, 10, 11, 12, 13, 14, 15, 16, 17, 18, 19, or 20 contiguous nucleobases along a strand of the dsRNA compound. In certain embodiments, the double stranded compound comprises one or more linkages between adjacent nucleotides other than a naturally-occurring phosphodiester linkage. Examples of such linkages include phosphoramide, phosphorothioate, and phosphorodithioate linkages. The double stranded compounds may also be chemically modified nucleic acid molecules as taught in U.S. Pat. No. 6,673,661. In other embodiments, the dsRNA contains one or two capped strands, as disclosed, for example, by WO 00/63364, filed Apr. 19, 2000. In certain embodiments, the first strand of the double stranded compound is an siRNA guide strand and the second strand of the double stranded compound is an siRNA passenger strand. In certain embodiments, the second strand of the double stranded compound is complementary to the first strand. In certain embodiments, each strand of the double stranded compound consists of 16, 17, 18, 19, 20, 21, 22, or 23 linked nucleosides. In certain embodiments, the first or second strand of the double stranded compound can comprise a conjugate group.

In certain embodiments, a single stranded compound described herein can comprise any of the oligonucleotide sequences targeted to a KEAP1 described herein. In certain embodiments, such a single stranded compound is a single stranded RNAi (ssRNAi) compound. In certain embodiments, a ssRNAi compound comprises at least an 8, 9, 10, 11, 12, 13, 14, 15, 16, 17, 18, 19, or 20 contiguous nucleobase portion complementary to any one of SEQ ID NOs: 7-9. In certain embodiments, a ssRNAi compound comprises the nucleobase sequence complementary to any one of SEQ ID NOs: 1-6. In certain embodiments, the ssRNAi compound comprises ribonucleotides in which uracil (U) is in place of thymine (T). In certain embodiments, ssRNAi compound comprises a nucleobase sequence complementary to the site on a KEAP1 with any of the sequences of SEQ ID NOs: 1-6. In certain embodiments, a ssRNAi compound comprises one or more modified nucleotides in which the 2' position in the sugar contains a halogen (such as fluorine group; 2'-F) or contains an alkoxy group (such as a methoxy group; 2'-OMe). In certain embodiments, a ssRNAi compound comprises at least one 2'-F sugar modification and at least one 2'-OMe sugar modification. In certain embodiments, the at least one 2'-F sugar modification and at least one 2'-OMe sugar modification are arranged in an alternating pattern for at least 2, 3, 4, 5, 6, 7, 8, 9, 10, 11, 12, 13, 14, 15, 16, 17, 18, 19, or 20 contiguous nucleobases along a strand of the ssRNAi compound. In certain embodiments, the ssRNAi compound comprises one or more linkages between adjacent nucleotides other than a naturally-occurring phosphodiester linkage. Examples of such linkages include phosphoramide, phosphorothioate, and phosphorodithioate linkages. The ssRNAi compounds may also be chemically modified nucleic acid molecules as taught in U.S. Pat. No. 6,673,661. In other embodiments, the ssRNAi contains a capped strand, as disclosed, for example, by WO 00/63364, filed Apr. 19, 2000. In certain embodiments, the ssRNAi compound consists of 16, 17, 18, 19, 20, 21, 22, or 23 linked nucleosides. In certain embodiments, the ssRNAi compound can comprise a conjugate group.

In certain embodiments, compounds described herein comprise modified oligonucleotides. Certain modified oligonucleotides have one or more asymmetric center and thus give rise to enantiomers, diastereomers, and other stereoisomeric configurations that may be defined, in terms of absolute stereochemistry, as (R) or (S), as a or 13 such as for sugar anomers, or as (D) or (L) such as for amino acids etc. Included in the modified oligonucleotides provided herein are all such possible isomers, including their racemic and optically pure forms, unless specified otherwise. Likewise, all cis- and trans-isomers and tautomeric forms are also included.

Certain Mechanisms

In certain embodiments, compounds described herein comprise or consist of modified oligonucleotides. In certain embodiments, compounds described herein are antisense compounds. In certain embodiments, such antisense compounds comprise oligomeric compounds. In certain embodiments, compounds described herein are capable of hybridizing to a target nucleic acid, resulting in at least one antisense activity. In certain embodiments, compounds described herein selectively affect one or more target nucleic acid. Such selective compounds comprise a nucleobase sequence that hybridizes to one or more target nucleic acid, resulting in one or more desired antisense activity and does not hybridize to one or more non-target nucleic acid or does not hybridize to one or more non-target nucleic acid in such a way that results in a significant undesired antisense activity.

In certain antisense activities, hybridization of a compound described herein to a target nucleic acid results in recruitment of a protein that cleaves the target nucleic acid. For example, certain compounds described herein result in RNase H mediated cleavage of the target nucleic acid. RNase H is a cellular endonuclease that cleaves the RNA strand of an RNA:DNA duplex. The DNA in such an RNA:DNA duplex need not be unmodified DNA. In certain embodiments, compounds described herein are sufficiently "DNA-like" to elicit RNase H activity. Further, in certain embodiments, one or more non-DNA-like nucleoside in the gap of a gapmer is tolerated.

In certain antisense activities, compounds described herein or a portion of the compound is loaded into an RNA-induced silencing complex (RISC), ultimately resulting in cleavage of the target nucleic acid. For example, certain compounds described herein result in cleavage of the target nucleic acid by Argonaute. Compounds that are loaded into RISC are RNAi compounds. RNAi compounds may be double stranded (siRNA) or single stranded (ssRNA).

In certain embodiments, hybridization of compounds described herein to a target nucleic acid does not result in recruitment of a protein that cleaves that target nucleic acid. In certain such embodiments, hybridization of the compound to the target nucleic acid results in alteration of splicing of the target nucleic acid. In certain embodiments, hybridization of the compound to a target nucleic acid results in inhibition of a binding interaction between the target nucleic acid and a protein or other nucleic acid. In certain such embodiments, hybridization of the compound to a target nucleic acid results in alteration of translation of the target nucleic acid.

Antisense activities may be observed directly or indirectly. In certain embodiments, observation or detection of an antisense activity involves observation or detection of a change in an amount of a target nucleic acid or protein encoded by such target nucleic acid, a change in the ratio of splice variants of a nucleic acid or protein, and/or a phenotypic change in a cell or animal.

Target Nucleic Acids, Target Regions and Nucleotide Sequences

In certain embodiments, compounds described herein comprise or consist of an oligonucleotide comprising a region that is complementary to a target nucleic acid. In certain embodiments, the target nucleic acid is an endogenous RNA molecule. In certain such embodiments, the target nucleic acid is selected from: an mRNA and a pre-mRNA, including intronic, exonic and untranslated regions. In certain embodiments, the target nucleic acid is a pre-mRNA. In certain such embodiments, the target region is entirely within an intron. In certain embodiments, the target region spans an intron/exon junction. In certain embodiments, the target region is at least 50% within an intron.

Human sequences that encode KEAP1 include, without limitation, the following sequences: GenBank Accession No. NM_203500.1 (incorporated herein as SEQ ID NO: 1), GenBank Accession No. NM_012289.3 (incorporated herein as SEQ ID NO: 2) and GenBank Accession No. NC_000019.10 nucleotides 10483001_10506000 (incorporated herein as SEQ ID NO: 3).

Mouse sequences that encode KEAP1 include, without limitation, the following sequences: GenBank Accession No. NM_001110305.1 (incorporated herein as SEQ ID NO: 4), GenBank Accession No. NM_016679.4 (incorporated herein as SEQ ID NO: 5), GenBank Accession No. NC_000075.6 nucleotides 21227001_21242000 (incorporated herein as SEQ ID NO: 6).

Hybridization

In some embodiments, hybridization occurs between a compound disclosed herein and a KEAP1 nucleic acid. The most common mechanism of hybridization involves hydrogen bonding (e.g., Watson-Crick, Hoogsteen or reversed Hoogsteen hydrogen bonding) between complementary nucleobases of the nucleic acid molecules.

Hybridization can occur under varying conditions. Hybridization conditions are sequence-dependent and are determined by the nature and composition of the nucleic acid molecules to be hybridized.

Methods of determining whether a sequence is specifically hybridizable to a target nucleic acid are well known in the art. In certain embodiments, the compounds provided herein are specifically hybridizable with a KEAP1 nucleic acid.

Complementarity

An oligonucleotide is said to be complementary to another nucleic acid when the nucleobase sequence of such oligonucleotide or one or more regions thereof matches the nucleobase sequence of another oligonucleotide or nucleic acid or one or more regions thereof when the two nucleobase sequences are aligned in opposing directions. Nucleobase matches or complementary nucleobases, as described herein, are limited to adenine (A) and thymine (T), adenine (A) and uracil (U), cytosine (C) and guanine (G), and 5-methyl cytosine (mC) and guanine (G) unless otherwise specified. Complementary oligonucleotides and/or nucleic acids need not have nucleobase complementarity at each nucleoside and may include one or more nucleobase mismatches. An oligonucleotide is fully complementary or 100% complementary when such oligonucleotides have nucleobase matches at each nucleoside without any nucleobase mismatches.

In certain embodiments, compounds described herein comprise or consist of modified oligonucleotides. In certain embodiments, compounds described herein are antisense compounds. In certain embodiments, compounds comprise oligomeric compounds. Non-complementary nucleobases between a compound and a KEAP1 nucleic acid may be tolerated provided that the compound remains able to specifically hybridize to a target nucleic acid. Moreover, a compound may hybridize over one or more segments of a KEAP1 nucleic acid such that intervening or adjacent segments are not involved in the hybridization event (e.g., a loop structure, mismatch or hairpin structure).

In certain embodiments, the compounds provided herein, or a specified portion thereof, are, or are at least, 70%, 80%, 85%, 86%, 87%, 88%, 89%, 90%, 91%, 92%, 93%, 94%, 95%, 96%, 97%, 98%, 99%, or 100% complementary to a KEAP1 nucleic acid, a target region, target segment, or specified portion thereof. Percent complementarity of a compound with a target nucleic acid can be determined using routine methods.

For example, a compound in which 18 of 20 nucleobases of the compound are complementary to a target region, and would therefore specifically hybridize, would represent 90 percent complementarity. In this example, the remaining non-complementary nucleobases may be clustered or interspersed with complementary nucleobases and need not be contiguous to each other or to complementary nucleobases. As such, a compound which is 18 nucleobases in length having four non-complementary nucleobases which are flanked by two regions of complete complementarity with the target nucleic acid would have 77.8% overall complementarity with the target nucleic acid and would thus fall within the scope of the present invention. Percent complementarity of a compound with a region of a target nucleic acid can be determined routinely using BLAST programs (basic local alignment search tools) and PowerBLAST programs known in the art (Altschul et al., *J. Mol. Biol.*, 1990, 215, 403 410; Zhang and Madden, Genome Res., 1997, 7, 649 656). Percent homology, sequence identity or complementarity, can be determined by, for example, the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482 489).

In certain embodiments, compounds described herein, or specified portions thereof, are fully complementary (i.e. 100% complementary) to a target nucleic acid, or specified portion thereof. For example, a compound may be fully complementary to a KEAP1 nucleic acid, or a target region, or a target segment or target sequence thereof. As used herein, "fully complementary" means each nucleobase of a compound is capable of precise base pairing with the corresponding nucleobases of a target nucleic acid. For example, a 20 nucleobase compound is fully complementary to a target sequence that is 400 nucleobases long, so long as there is a corresponding 20 nucleobase portion of the target nucleic acid that is fully complementary to the compound. Fully complementary can also be used in reference to a specified portion of the first and/or the second nucleic acid. For example, a 20 nucleobase portion of a 30 nucleobase compound can be "fully complementary" to a target sequence that is 400 nucleobases long. The 20 nucleobase portion of the 30 nucleobase compound is fully complementary to the target sequence if the target sequence has a corresponding 20 nucleobase portion wherein each nucleobase is complementary to the 20 nucleobase portion of the compound. At the same time, the entire 30 nucleobase compound may or may not be fully complementary to the target sequence, depending on whether the remaining 10 nucleobases of the compound are also complementary to the target sequence.

In certain embodiments, compounds described herein comprise one or more mismatched nucleobases relative to the target nucleic acid. In certain such embodiments, antisense activity against the target is reduced by such mismatch, but activity against a non-target is reduced by a greater amount. Thus, in certain such embodiments selectivity of the compound is improved. In certain embodiments, the mismatch is specifically positioned within an oligonucleotide having a gapmer motif. In certain such embodiments, the mismatch is at position 1, 2, 3, 4, 5, 6, 7, or 8 from the 5'-end of the gap region. In certain such embodiments, the mismatch is at position 9, 8, 7, 6, 5, 4, 3, 2, 1 from the 3'-end of the gap region. In certain such embodiments, the mismatch is at position 1, 2, 3, or 4 from the 5'-end of the wing region. In certain such embodiments, the mismatch is at position 4, 3, 2, or 1 from the 3'-end of the wing region. In certain embodiments, the mismatch is specifically positioned within an oligonucleotide not having a gapmer motif. In certain such embodiments, the mismatch is at position 1, 2, 3, 4, 5, 6, 7, 8, 9, 10, 11, or 12 from the 5'-end of the oligonucleotide. In certain such embodiments, the mismatch is at position, 2, 3, 4, 5, 6, 7, 8, 9, 10, 11, or 12 from the 3'-end of the oligonucleotide.

The location of a non-complementary nucleobase may be at the 5' end or 3' end of the compound. Alternatively, the non-complementary nucleobase or nucleobases may be at an internal position of the compound. When two or more non-complementary nucleobases are present, they may be contiguous (i.e. linked) or non-contiguous. In one embodiment, a non-complementary nucleobase is located in the wing segment of a gapmer oligonucleotide.

In certain embodiments, compounds described herein that are, or are up to 11, 12, 13, 14, 15, 16, 17, 18, 19, or 20 nucleobases in length comprise no more than 4, no more than 3, no more than 2, or no more than 1 non-complementary nucleobase(s) relative to a target nucleic acid, such as a KEAP1 nucleic acid, or specified portion thereof.

In certain embodiments, compounds described herein that are, or are up to 11, 12, 13, 14, 15, 16, 17, 18, 19, 20, 21, 22, 23, 24, 25, 26, 27, 28, 29, or 30 nucleobases in length comprise no more than 6, no more than 5, no more than 4, no more than 3, no more than 2, or no more than 1 non-complementary nucleobase(s) relative to a target nucleic acid, such as a KEAP1 nucleic acid, or specified portion thereof.

In certain embodiments, compounds described herein also include those which are complementary to a portion of a target nucleic acid. As used herein, "portion" refers to a defined number of contiguous (i.e. linked) nucleobases within a region or segment of a target nucleic acid. A "portion" can also refer to a defined number of contiguous nucleobases of a compound. In certain embodiments, the compounds, are complementary to at least an 8 nucleobase portion of a target segment. In certain embodiments, the compounds are complementary to at least a 9 nucleobase portion of a target segment. In certain embodiments, the compounds are complementary to at least a 10 nucleobase portion of a target segment. In certain embodiments, the compounds are complementary to at least an 11 nucleobase portion of a target segment. In certain embodiments, the compounds are complementary to at least a 12 nucleobase portion of a target segment. In certain embodiments, the compounds are complementary to at least a 13 nucleobase portion of a target segment. In certain embodiments, the compounds are complementary to at least a 14 nucleobase portion of a target segment. In certain embodiments, the compounds are complementary to at least a 15 nucleobase portion of a target segment. In certain embodiments, the compounds are complementary to at least a 16 nucleobase portion of a target segment. Also contemplated are compounds that are complementary to at least a 9, 10, 11, 12, 13, 14, 15, 16, 17, 18, 19, 20, or more nucleobase portion of a target segment, or a range defined by any two of these values.

Identity

The compounds provided herein may also have a defined percent identity to a particular nucleotide sequence, SEQ ID NO, or compound represented by a specific Isis number, or portion thereof. In certain embodiments, compounds described herein are antisense compounds or oligomeric compounds. In certain embodiments, compounds described herein are modified oligonucleotides. As used herein, a compound is identical to the sequence disclosed herein if it has the same nucleobase pairing ability. For example, a RNA which contains uracil in place of thymidine in a disclosed DNA sequence would be considered identical to the DNA sequence since both uracil and thymidine pair with adenine. Shortened and lengthened versions of the compounds described herein as well as compounds having non-identical bases relative to the compounds provided herein also are contemplated. The non-identical bases may be adjacent to each other or dispersed throughout the compound. Percent identity of an compound is calculated according to the number of bases that have identical base pairing relative to the sequence to which it is being compared.

In certain embodiments, compounds described herein, or portions thereof, are, or are at least, 70%, 75%, 80%, 85%, 90%, 91%, 92%, 93%, 94%, 95%, 96%, 97%, 98%, 99% or 100% identical to one or more of the compounds or SEQ ID NOs, or a portion thereof, disclosed herein. In certain embodiments, compounds described herein are about 70%, 75%, 80%, 85%, 90%, 91%, 92%, 93%, 94%, 95%, 96%, 97%, 98%, or 99% identical, or any percentage between such values, to a particular nucleotide sequence, SEQ ID NO, or compound represented by a specific Isis number, or portion thereof, in which the compounds comprise an oligonucleotide having one or more mismatched nucleobases. In certain such embodiments, the mismatch is at position 1, 2, 3, 4, 5, 6, 7, 8, 9, 10, 11, or 12 from the 5'-end of the oligonucleotide. In certain such embodiments, the mismatch is at position 1, 2, 3, 4, 5, 6, 7, 8, 9, 10, 11, or 12 from the 3'-end of the oligonucleotide.

In certain embodiments, compounds described herein are antisense compounds. In certain embodiments, a portion of the compound is compared to an equal length portion of the target nucleic acid. In certain embodiments, an 8, 9, 10, 11, 12, 13, 14, 15, 16, 17, 18, 19, 20, 21, 22, 23, 24, or 25 nucleobase portion is compared to an equal length portion of the target nucleic acid.

In certain embodiments, compounds described herein are oligonucleotides. In certain embodiments, a portion of the oligonucleotide is compared to an equal length portion of the target nucleic acid. In certain embodiments, an 8, 9, 10, 11, 12, 13, 14, 15, 16, 17, 18, 19, 20, 21, 22, 23, 24, or 25 nucleobase portion is compared to an equal length portion of the target nucleic acid.

Certain Modified Compounds

In certain embodiments, compounds described herein comprise or consist of oligonucleotides consisting of linked nucleosides. Oligonucleotides may be unmodified oligonucleotides (RNA or DNA) or may be modified oligonucleotides. Modified oligonucleotides comprise at least one modification relative to unmodified RNA or DNA (i.e., comprise at least one modified nucleoside (comprising a modified sugar moiety and/or a modified nucleobase) and/or at least one modified internucleoside linkage).

A. Modified Nucleosides

Modified nucleosides comprise a modified sugar moiety or a modified nucleobase or both a modified sugar moiety and a modified nucleobase.

1. Modified Sugar Moieties

In certain embodiments, sugar moieties are non-bicyclic modified sugar moieties. In certain embodiments, modified sugar moieties are bicyclic or tricyclic sugar moieties. In certain embodiments, modified sugar moieties are sugar surrogates. Such sugar surrogates may comprise one or more substitutions corresponding to those of other types of modified sugar moieties.

In certain embodiments, modified sugar moieties are non-bicyclic modified sugar moieties comprising a furanosyl ring with one or more acyclic substituent, including but not limited to substituents at the 2', 4', and/or 5' positions. In certain embodiments one or more acyclic substituent of non-bicyclic modified sugar moieties is branched. Examples of 2'-substituent groups suitable for non-bicyclic modified sugar moieties include but are not limited to: 2'-F, 2'-OCH$_3$ ("OMe" or "O-methyl"), and 2'-O(CH$_2$)$_2$OCH$_3$ ("MOE"). In certain embodiments, 2'-substituent groups are selected from among: halo, allyl, amino, azido, SH, CN, OCN, CF$_3$, OCF$_3$, alkoxy, O—C$_1$-C$_{10}$ substituted alkoxy, O—C$_1$-C$_{10}$ alkyl, O—C$_1$-C$_{10}$ substituted alkyl, S-alkyl, N(R$_m$)-alkyl, O-alkenyl, S-alkenyl, N(R$_m$)-alkenyl, O-alkynyl, S-alkynyl, N(R$_m$)-alkynyl, O-alkylenyl-O-alkyl, alkynyl, alkaryl, aralkyl, O-alkaryl, O-aralkyl, O(CH$_2$)$_2$SCH$_3$, O(CH$_2$)$_2$ON(R$_m$)(R$_n$) or OCH$_2$C(=O)—N(R$_m$)(R$_n$), where each R$_m$ and R$_n$ is, independently, H, an amino protecting group, or substituted or unsubstituted C$_1$-C$_{10}$ alkyl, and the 2'-substituent groups described in Cook et al., U.S. Pat. No. 6,531,584; Cook et al., U.S. Pat. No. 5,859,221; and Cook et al., U.S. Pat. No. 6,005,087. Certain embodiments of these 2'-substituent groups can be further substituted with one or more substituent groups independently selected from among: hydroxyl, amino, alkoxy, carboxy, benzyl, phenyl, nitro (NO$_2$), thiol, thioalkoxy, thioalkyl, halogen, alkyl, aryl, alkenyl and alkynyl. Examples of 4'-substituent groups suitable for linearlynon-bicyclic modified sugar moieties include but are not limited to alkoxy (e.g., methoxy), alkyl, and those described in Manoharan et al., WO 2015/106128. Examples of 5'-substituent groups suitable for non-bicyclic modified sugar moieties include but are not limited to: 5'-methyl (R or S), 5'-vinyl, and 5'-methoxy. In certain embodiments, non-bicyclic modified sugars comprise more than one non-bridging sugar substituent, for example, 2'-F-5'-methyl sugar moieties and the modified sugar moieties and modified nucleosides described in Migawa et al., WO 2008/101157 and Rajeev et al., US2013/0203836.

In certain embodiments, a 2'-substituted nucleoside or 2'-non-bicyclic modified nucleoside comprises a sugar moiety comprising a linear 2'-substituent group selected from: F, $NH_2$, $N_3$, $OCF_3$, $OCH_3$, $O(CH_2)_3NH_2$, $CH_2CH=CH_2$, $OCH_2$ $CH=CH_2$, $OCH_2CH_2OCH_3$, $O(CH_2)_2SCH_3$, $O(CH_2)_2ON(R_m)(R_n)$, $O(CH_2)_2O(CH_2)_2N(CH_3)_2$, and N-substituted acetamide ($OCH_2C(=O)-N(R_m)(R_n)$), where each $R_m$ and $R_n$ is, independently, H, an amino protecting group, or substituted or unsubstituted $C_1$-$C_{10}$ alkyl.

In certain embodiments, a 2'-substituted nucleoside or 2'-non-bicyclic modified nucleoside comprises a sugar moiety comprising a linear 2'-substituent group selected from: F, $OCF_3$, $OCH_3$, $OCH_2CH_2OCH_3$, $O(CH_2)_2SCH_3$, $O(CH_2)_2ON(CH_3)_2$, $O(CH_2)_2O(CH_2)_2N(CH_3)_2$, and $OCH_2C(=O)-N(H)CH_3$ ("NMA").

In certain embodiments, a 2'-substituted nucleoside or 2'-non-bicyclic modified nucleoside comprises a sugar moiety comprising a linear 2'-substituent group selected from: F, $OCH_3$, and $OCH_2CH_2OCH_3$.

Nucleosides comprising modified sugar moieties, such as non-bicyclic modified sugar moieties, are referred to by the position(s) of the substitution(s) on the sugar moiety of the nucleoside. For example, nucleosides comprising 2'-substituted or 2-modified sugar moieties are referred to as 2'-substituted nucleosides or 2-modified nucleosides.

Certain modified sugar moieties comprise a bridging sugar substituent that forms a second ring resulting in a bicyclic sugar moiety. In certain such embodiments, the bicyclic sugar moiety comprises a bridge between the 4' and the 2' furanose ring atoms. Examples of such 4' to 2' bridging sugar substituents include but are not limited to: 4'-$CH_2$-2', 4'-$(CH_2)_2$-2', 4'-$(CH_2)_3$-2', ("LNA"), $(CH_2)_2$—O-2' ("ENA"), 4'-$CH(CH_3)$—O-2' (referred to as "constrained ethyl" or "cEt" when in the S configuration), 4'-$CH_2$—O—$CH_2$-2', 4'-$CH_2$—N(R)-2', 4'-$CH(CH_2OCH_3)$—O-2' ("constrained MOE" or "cMOE") and analogs thereof (see, e.g., Seth et al., U.S. Pat. No. 7,399,845, Bhat et al., U.S. Pat. No. 7,569,686, Swayze et al., U.S. Pat. No. 7,741,457, and Swayze et al., U.S. Pat. No. 8,022,193), 4'-$C(CH_3)(CH_3)$—O-2' and analogs thereof (see, e.g., Seth et al., U.S. Pat. No. 8,278,283), 4'-$CH_2$—N($OCH_3$)-2' and analogs thereof (see, e.g., Prakash et al., U.S. Pat. No. 8,278,425), 4'-$CH_2$—O—N($CH_3$)-2' (see, e.g., Allerson et al., U.S. Pat. No. 7,696,345 and Allerson et al., U.S. Pat. No. 8,124,745), 4'-$CH_2$—C(H)($CH_3$)-2' (see, e.g., Zhou, et al., J. Org. Chem., 2009, 74, 118-134), 4'-$CH_2$—C(=$CH_2$)-2' and analogs thereof (see e.g., Seth et al., U.S. Pat. No. 8,278,426), 4'-$C(R_aR_b)$—N(R)—O-2', 4'—$CH_2$—O—N(R)-2', and 4'-$CH_2$—N(R)—O-2', wherein each R, $R_a$, and $R_b$ is, independently, H, a protecting group, or $C_1$-$C_{12}$ alkyl (see, e.g. Imanishi et al., U.S. Pat. No. 7,427,672).

In certain embodiments, such 4' to 2' bridges independently comprise from 1 to 4 linked groups independently selected from: —$[C(R_a)(R_b)]_n$—, —$[C(R_a)(R_b)]_n$—O—, —$C(R_a)=C(R_b)$—, —$C(R_a)=N$—, —$C(=NR_a)$—, —$C(=O)$—, —$C(=S)$—, —O—, —$Si(R_a)_2$—, —$S(=O)_x$—, and —$N(R_a)$—;
wherein:
x is 0, 1, or 2;
n is 1, 2, 3, or 4;
each $R_a$ and $R_b$ is, independently, H, a protecting group, hydroxyl, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, heterocycle radical, substituted heterocycle radical, heteroaryl, substituted heteroaryl, $C_5$-$C_7$ alicyclic radical, substituted $C_5$-$C_7$ alicyclic radical, halogen, $OJ_1$, $NJ_1J_2$, $SJ_1$, $N_3$, $COOJ_1$, acyl ($C(=O)$—H), substituted acyl, CN, sulfonyl ($S(=O)_2$-$J_1$), or sulfoxyl ($S(=O)$-$J_1$); and each $J_1$ and $J_2$ is, independently, H, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, acyl ($C(=O)$—H), substituted acyl, a heterocycle radical, a substituted heterocycle radical, $C_1$-$C_{12}$ aminoalkyl, substituted $C_1$-$C_{12}$ aminoalkyl, or a protecting group.

Additional bicyclic sugar moieties are known in the art, see, for example: Freier et al., Nucleic Acids Research, 1997, 25(22), 4429-4443, Albaek et al., J. Org. Chem., 2006, 71, 7731-7740, Singh et al., Chem. Commun., 1998, 4, 455-456; Koshkin et al., Tetrahedron, 1998, 54, 3607-3630; Wahlestedt et al., Proc. Natl. Acad. Sci. U S. A., 2000, 97, 5633-5638; Kumar et al., Bioorg. Med. Chem. Lett., 1998, 8, 2219-2222; Singh et al., J. Org. Chem., 1998, 63, 10035-10039; Srivastava et al., J. Am. Chem. Soc., 20017, 129, 8362-8379; Elayadi et al., Curr. Opinion Invens. Drugs, 2001, 2, 558-561; Braasch et al., Chem. Biol., 2001, 8, 1-7; Orum et al., Curr. Opinion Mol. Ther., 2001, 3, 239-243; Wengel et al., U.S. Pat. No. 7,053,207, Imanishi et al., U.S. Pat. No. 6,268,490, Imanishi et al. U.S. Pat. No. 6,770,748, Imanishi et al., U.S. RE44,779; Wengel et al., U.S. Pat. No. 6,794,499, Wengel et al., U.S. Pat. No. 6,670,461; Wengel et al., U.S. Pat. No. 7,034,133, Wengel et al., U.S. Pat. No. 8,080,644; Wengel et al., U.S. Pat. No. 8,034,909; Wengel et al., U.S. Pat. No. 8,153,365; Wengel et al., U.S. Pat. No. 7,572,582; and Ramasamy et al., U.S. Pat. No. 6,525,191, Torsten et al., WO 2004/106356, Wengel et al., WO 91999/014226; Seth et al., WO 2007/134181; Seth et al., U.S. Pat. No. 7,547,684; Seth et al., U.S. Pat. No. 7,666,854; Seth et al., U.S. Pat. No. 8,088,746; Seth et al., U.S. Pat. No. 7,750,131; Seth et al., U.S. Pat. No. 8,030,467; Seth et al., U.S. Pat. No. 8,268,980; Seth et al., U.S. Pat. No. 8,546,556; Seth et al., U.S. Pat. No. 8,530,640; Migawa et al., U.S. Pat. No. 9,012,421; Seth et al., U.S. Pat. No. 8,501,805; and U.S. Patent Publication Nos. Allerson et al., US2008/0039618 and Migawa et al., US2015/0191727.

In certain embodiments, bicyclic sugar moieties and nucleosides incorporating such bicyclic sugar moieties are further defined by isomeric configuration. For example, an LNA nucleoside (described herein) may be in the α-L configuration or in the β-D configuration.

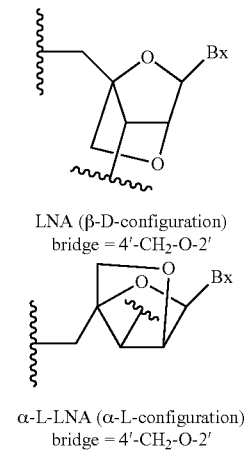

LNA (β-D-configuration)
bridge = 4'-$CH_2$-O-2'

α-L-LNA (α-L-configuration)
bridge = 4'-$CH_2$-O-2'

α-L-methyleneoxy (4'-$CH_2$—O-2') or α-L-LNA bicyclic nucleosides have been incorporated into oligonucleotides that showed antisense activity (Frieden et al., Nucleic Acids

*Research*, 2003, 21, 6365-6372). Herein, general descriptions of bicyclic nucleosides include both isomeric configurations. When the positions of specific bicyclic nucleosides (e.g., LNA or cEt) are identified in exemplified embodiments herein, they are in the β-D configuration, unless otherwise specified.

In certain embodiments, modified sugar moieties comprise one or more non-bridging sugar substituent and one or more bridging sugar substituent (e.g., 5'-substituted and 4'-2' bridged sugars).

In certain embodiments, modified sugar moieties are sugar surrogates. In certain such embodiments, the oxygen atom of the sugar moiety is replaced, e.g., with a sulfur, carbon or nitrogen atom. In certain such embodiments, such modified sugar moieties also comprise bridging and/or non-bridging substituents as described herein. For example, certain sugar surrogates comprise a 4'-sulfur atom and a substitution at the 2'-position (see, e.g., Bhat et al., U.S. Pat. No. 7,875,733 and Bhat et al., U.S. Pat. No. 7,939,677) and/or the 5' position.

In certain embodiments, sugar surrogates comprise rings having other than 5 atoms. For example, in certain embodiments, a sugar surrogate comprises a six-membered tetrahydropyran ("THP"). Such tetrahydropyrans may be further modified or substituted. Nucleosides comprising such modified tetrahydropyrans include but are not limited to hexitol nucleic acid ("HNA"), anitol nucleic acid ("ANA"), manitol nucleic acid ("MNA") (see e.g., Leumann, C J. *Bioorg. & Med. Chem.* 2002, 10, 841-854), fluoro HNA:

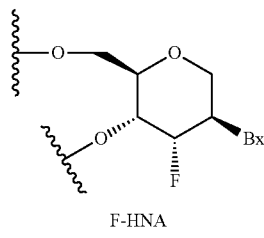

F-HNA ("F-HNA", see e.g., Swayze et al., U.S. Pat. No. 8,088,904; Swayze et al., U.S. Pat. No. 8,440,803; Swayze et al., U.S.; and Swayze et al., U.S. Pat. No. 9,005,906, F-HNA can also be referred to as a F-THP or 3'-fluoro tetrahydropyran), and nucleosides comprising additional modified THP compounds having the formula:

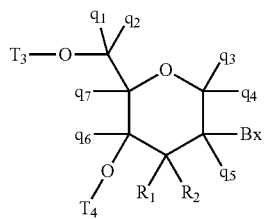

wherein, independently, for each of said modified THP nucleoside: Bx is a nucleobase moiety; $T_3$ and $T_4$ are each, independently, an internucleoside linking group linking the modified THP nucleoside to the remainder of an oligonucleotide or one of $T_3$ and $T_4$ is an internucleoside linking group linking the modified THP nucleoside to the remainder of an oligonucleotide and the other of $T_3$ and $T_4$ is H, a hydroxyl protecting group, a linked conjugate group, or a 5' or 3'-terminal group; $q_1$, $q_2$, $q_3$, $q_4$, $q_5$, $q_6$ and $q_7$ are each, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, or substituted $C_2$-$C_6$ alkynyl; and each of $R_1$ and $R_2$ is independently selected from among: hydrogen, halogen, substituted or unsubstituted alkoxy, $NJ_1J_2$, $SJ_1$, $N_3$, $OC(=X)J_1$, $OC(=X)NJ_1J_2$, $NJ_3C(=X)NJ_1J_2$, and CN, wherein X is O, S or $NJ_1$, and each $J_1$, $J_2$, and $J_3$ is, independently, H or $C_1$-$C_6$ alkyl.

In certain embodiments, modified THP nucleosides are provided wherein $q_1$, $q_2$, $q_3$, $q_4$, $q_5$, $q_6$ and $q_7$ are each H. In certain embodiments, at least one of $q_1$, $q_2$, $q_3$, $q_4$, $q_5$, $q_6$ and $q_7$ is other than H. In certain embodiments, at least one of $q_1$, $q_2$, $q_3$, $q_4$, $q_5$, $q_6$ and $q_7$ is methyl. In certain embodiments, modified THP nucleosides are provided wherein one of $R_1$ and $R_2$ is F. In certain embodiments, $R_1$ is F and $R_2$ is H, in certain embodiments, $R_1$ is methoxy and $R_2$ is H, and in certain embodiments, $R_1$ is methoxyethoxy and $R_2$ is H.

In certain embodiments, sugar surrogates comprise rings having more than 5 atoms and more than one heteroatom. For example, nucleosides comprising morpholino sugar moieties and their use in oligonucleotides have been reported (see, e.g., Braasch et al., Biochemistry, 2002, 41, 4503-4510 and Summerton et al., U.S. Pat. No. 5,698,685; Summerton et al., U.S. Pat. No. 5,166,315; Summerton et al., U.S. Pat. No. 5,185,444; and Summerton et al., U.S. Pat. No. 5,034,506). As used here, the term "morpholino" means a sugar surrogate having the following structure:

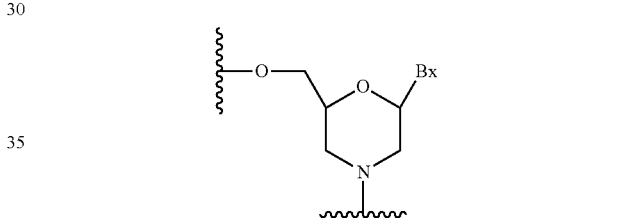

In certain embodiments, morpholinos may be modified, for example by adding or altering various substituent groups from the above morpholino structure. Such sugar surrogates are referred to herein as "modified morpholinos."

In certain embodiments, sugar surrogates comprise acyclic moieites. Examples of nucleosides and oligonucleotides comprising such acyclic sugar surrogates include but are not limited to: peptide nucleic acid ("PNA"), acyclic butyl nucleic acid (see, e.g., Kumar et al., *Org. Biomol. Chem.*, 2013, 11, 5853-5865), and nucleosides and oligonucleotides described in Manoharan et al., WO2011/133876.

Many other bicyclic and tricyclic sugar and sugar surrogate ring systems are known in the art that can be used in modified nucleosides.

2. Modified Nucleobases

Nucleobase (or base) modifications or substitutions are structurally distinguishable from, yet functionally interchangeable with, naturally occurring or synthetic unmodified nucleobases. Both natural and modified nucleobases are capable of participating in hydrogen bonding. Such nucleobase modifications can impart nuclease stability, binding affinity or some other beneficial biological property to compounds described herein.

In certain embodiments, compounds described herein comprise modified oligonucleotides. In certain embodiments, modified oligonucleotides comprise one or more nucleoside comprising an unmodified nucleobase. In certain embodiments, modified oligonucleotides comprise one or more nucleoside comprising a modified nucleobase. In certain embodiments, modified oligonucleotides comprise one or more nucleoside that does not comprise a nucleobase, referred to as an abasic nucleoside.

In certain embodiments, modified nucleobases are selected from: 5-substituted pyrimidines, 6-azapyrimi¬dines, alkyl or alkynyl substituted pyrimidines, alkyl substituted purines, and N-2, N-6 and O-6 substituted purines. In certain embodiments, modified nucleobases are selected from: 2-aminopropyladenine, 5-hydroxymethyl cytosine, 5-methylcytosine, xanthine, hypoxanthine, 2-aminoadenine, 6-N-methylguanine, 6-N-methyladenine, 2-propyladenine, 2-thiouracil, 2-thiothymine and 2-thiocytosine, 5-propynyl (C≡C—CH3) uracil, 5-propynylcytosine, 6-azouracil, 6-azocytosine, 6-azothymine, 5-ribosyluracil (pseudouracil), 4-thiouracil, 8-halo, 8-amino, 8-thiol, 8-thioalkyl, 8-hydroxyl, 8-aza and other 8-substituted purines, 5-halo, particularly 5-bromo, 5-trifluoromethyl, 5-halouracil, and 5-halocytosine, 7-methylguanine, 7-methyladenine, 2-F-adenine, 2-aminoadenine, 7-deazaguanine, 7-deazaadenine, 3-deazaguanine, 3-deazaadenine, 6-N-benzoyladenine, 2-N-isobutyrylguanine, 4-N-benzoylcytosine, 4-N-benzoyluracil, 5-methyl 4-N-benzoylcytosine, 5-methyl 4-N-benzoyluracil, universal bases, hydrophobic bases, promiscuous bases, size-expanded bases, and fluorinated bases. Further modified nucleobases include tricyclic pyrimidines, such as 1,3-diazaphenoxazine-2-one, 1,3-diazaphenothiazine-2-one and 9-(2-aminoethoxy)-1,3-diazaphenoxazine-2-one (G-clamp). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in Merigan et al., U.S. Pat. No. 3,687,808, those disclosed in The Concise Encyclopedia Of Polymer Science And Engineering, Kroschwitz, J. I., Ed., John Wiley & Sons, 1990, 858-859; Englisch et al., Angewandte Chemie, International Edition, 1991, 30, 613; Sanghvi, Y. S., Chapter 15, Antisense Research and Applications, Crooke, S. T. and Lebleu, B., Eds., CRC Press, 1993, 273-288; and those disclosed in Chapters 6 and 15, Antisense Drug Technology, Crooke S. T., Ed., CRC Press, 2008, 163-166 and 442-443.

Publications that teach the preparation of certain of the above noted modified nucleobases as well as other modified nucleobases include without limitation, Manoharan et al., US2003/0158403, Manoharan et al., US2003/0175906; Dinh et al., U.S. Pat. No. 4,845,205; Spielvogel et al., U.S. Pat. No. 5,130,302; Rogers et al., U.S. Pat. No. 5,134,066; Bischofberger et al., U.S. Pat. No. 5,175,273; Urdea et al., U.S. Pat. No. 5,367,066; Benner et al., U.S. Pat. No. 5,432,272; Matteucci et al., U.S. Pat. No. 5,434,257; Gmeiner et al., U.S. Pat. No. 5,457,187; Cook et al., U.S. Pat. No. 5,459,255; Froehler et al., U.S. Pat. No. 5,484,908; Matteucci et al., U.S. Pat. No. 5,502,177; Hawkins et al., U.S. Pat. No. 5,525,711; Haralambidis et al., U.S. Pat. No. 5,552,540; Cook et al., U.S. Pat. No. 5,587,469; Froehler et al., U.S. Pat. No. 5,594,121; Switzer et al., U.S. Pat. No. 5,596,091; Cook et al., U.S. Pat. No. 5,614,617; Froehler et al., U.S. Pat. No. 5,645,985; Cook et al., U.S. Pat. No. 5,681,941; Cook et al., U.S. Pat. No. 5,811,534; Cook et al., U.S. Pat. No. 5,750,692; Cook et al., U.S. Pat. No. 5,948,903; Cook et al., U.S. Pat. No. 5,587,470; Cook et al., U.S. Pat. No. 5,457,191; Matteucci et al., U.S. Pat. No. 5,763,588; Froehler et al., U.S. Pat. No. 5,830,653; Cook et al., U.S. Pat. No. 5,808,027; Cook et al., U.S. Pat. No. 6,166,199; and Matteucci et al., U.S. Pat. No. 6,005,096.

In certain embodiments, compounds targeted to a KEAP1 nucleic acid comprise one or more modified nucleobases. In certain embodiments, the modified nucleobase is 5-methylcytosine. In certain embodiments, each cytosine is a 5-methylcytosine.

Modified Internucleoside Linkages

The naturally occurring internucleoside linkage of RNA and DNA is a 3' to 5' phosphodiester linkage. In certain embodiments, compounds described herein having one or more modified, i.e. non-naturally occurring, internucleoside linkages are often selected over compounds having naturally occurring internucleoside linkages because of desirable properties such as, for example, enhanced cellular uptake, enhanced affinity for target nucleic acids, and increased stability in the presence of nucleases.

In certain embodiments, compounds targeted to a KEAP1 nucleic acid comprise one or more modified internucleoside linkages. In certain embodiments, the modified internucleoside linkages are phosphorothioate linkages. In certain embodiments, at least one internucleoside linkage of the compound is a phosphorothioate internucleoside linkage. In certain embodiments, each internucleoside linkage of the compound is a phosphorothioate internucleoside linkage.

In certain embodiments, compounds described herein comprise oligonucleotides. Oligonucleotides having modified internucleoside linkages include internucleoside linkages that retain a phosphorus atom as well as internucleoside linkages that do not have a phosphorus atom. Representative phosphorus containing internucleoside linkages include, but are not limited to, phosphodiesters, phosphotriesters, methylphosphonates, phosphoramidate, and phosphorothioates. Methods of preparation of phosphorous-containing and non-phosphorous-containing linkages are well known.

In certain embodiments, nucleosides of modified oligonucleotides may be linked together using any internucleoside linkage. The two main classes of internucleoside linking groups are defined by the presence or absence of a phosphorus atom. Representative phosphorus-containing internucleoside linkages include but are not limited to phosphates, which contain a phosphodiester bond ("P═O") (also referred to as unmodified or naturally occurring linkages), phosphotriesters, methylphosphonates, phosphoramidates, and phosphorothioates ("P═S"), and phosphorodithioates ("HS-P═S"). Representative non-phosphorus containing internucleoside linking groups include but are not limited to methylenemethylimino (—CH2-N(CH3)-O-CH2-), thiodiester, thionocarbamate (—O—C(═O)(NH)—S—); siloxane (—O—SiH2-O—); and N,N'-dimethylhydrazine (—CH2-N(CH3)-N(CH3)-). Modified internucleoside linkages, compared to naturally occurring phosphate linkages, can be used to alter, typically increase, nuclease resistance of the oligonucleotide. In certain embodiments, internucleoside linkages having a chiral atom can be prepared as a racemic mixture, or as separate enantiomers. Representative chiral internucleoside linkages include but are not limited to alkylphosphonates and phosphorothioates. Methods of preparation of phosphorous-containing and non-phosphorous-containing internucleoside linkages are well known to those skilled in the art.

Neutral internucleoside linkages include, without limitation, phosphotriesters, methylphosphonates, MMI (3'-CH2-N(CH3)-O-5'), amide-3 (3'-CH2-C(═O)—N(H)-5'), amide-4 (3'-CH2-N(H)—C(═O)-5'), formacetal (3'-O—CH2—O-5'), methoxypropyl, and thioformacetal (3'-S-CH2-O-5'). Further neutral internucleoside linkages include nonionic linkages comprising siloxane (dialkylsiloxane), carboxylate ester, carboxamide, sulfide, sulfonate ester and amides (See for example: Carbohydrate Modifications in Antisense Research; Y. S. Sanghvi and P. D. Cook, Eds., ACS Symposium Series 580; Chapters 3 and 4, 40-65). Further neutral internucleoside linkages include nonionic linkages comprising mixed N, O, S and $CH_2$ component parts.

In certain embodiments, oligonucleotides comprise modified internucleoside linkages arranged along the oligonucleotide or region thereof in a defined pattern or modified internucleoside linkage motif. In certain embodiments, internucleoside linkages are arranged in a gapped motif. In such embodiments, the internucleoside linkages in each of two wing regions are different from the internucleoside linkages in the gap region. In certain embodiments the internucleoside linkages in the wings are phosphodiester and the internucleoside linkages in the gap are phosphorothioate. The nucleoside motif is independently selected, so such oligonucleotides having a gapped internucleoside linkage motif may or may not have a gapped nucleoside motif and if it does have a gapped nucleoside motif, the wing and gap lengths may or may not be the same.

In certain embodiments, oligonucleotides comprise a region having an alternating internucleoside linkage motif. In certain embodiments, oligonucleotides of the present invention comprise a region of uniformly modified internucleoside linkages. In certain such embodiments, the oligonucleotide comprises a region that is uniformly linked by phosphorothioate internucleoside linkages. In certain embodiments, the oligonucleotide is uniformly linked by phosphorothioate. In certain embodiments, each internucleoside linkage of the oligonucleotide is selected from phosphodiester and phosphorothioate. In certain embodiments, each internucleoside linkage of the oligonucleotide is selected from phosphodiester and phosphorothioate and at least one internucleoside linkage is phosphorothioate.

In certain embodiments, the oligonucleotide comprises at least 6 phosphorothioate internucleoside linkages. In certain embodiments, the oligonucleotide comprises at least 8 phosphorothioate internucleoside linkages. In certain embodiments, the oligonucleotide comprises at least 10 phosphorothioate internucleoside linkages. In certain embodiments, the oligonucleotide comprises at least one block of at least 6 consecutive phosphorothioate internucleoside linkages. In certain embodiments, the oligonucleotide comprises at least one block of at least 8 consecutive phosphorothioate internucleoside linkages. In certain embodiments, the oligonucleotide comprises at least one block of at least 10 consecutive phosphorothioate internucleoside linkages. In certain embodiments, the oligonucleotide comprises at least block of at least one 12 consecutive phosphorothioate internucleoside linkages. In certain such embodiments, at least one such block is located at the 3' end of the oligonucleotide. In certain such embodiments, at least one such block is located within 3 nucleosides of the 3' end of the oligonucleotide.

In certain embodiments, oligonucleotides comprise one or more methylphosponate linkages. In certain embodiments, oligonucleotides having a gapmer nucleoside motif comprise a linkage motif comprising all phosphorothioate linkages except for one or two methylphosponate linkages. In certain embodiments, one methylphosponate linkage is in the central gap of an oligonucleotide having a gapmer nucleoside motif.

In certain embodiments, it is desirable to arrange the number of phosphorothioate internucleoside linkages and phosphodiester internucleoside linkages to maintain nuclease resistance. In certain embodiments, it is desirable to arrange the number and position of phosphorothioate internucleoside linkages and the number and position of phosphodiester internucleoside linkages to maintain nuclease resistance. In certain embodiments, the number of phosphorothioate internucleoside linkages may be decreased and the number of phosphodiester internucleoside linkages may be increased. In certain embodiments, the number of phosphorothioate internucleoside linkages may be decreased and the number of phosphodiester internucleoside linkages may be increased while still maintaining nuclease resistance. In certain embodiments it is desirable to decrease the number of phosphorothioate internucleoside linkages while retaining nuclease resistance. In certain embodiments it is desirable to increase the number of phosphodiester internucleoside linkages while retaining nuclease resistance.

Certain Motifs

In certain embodiments, compounds described herein comprise oligonucleotides. Oligonucleotides can have a motif, e.g. a pattern of unmodified and/or modified sugar moieties, nucleobases, and/or internucleoside linkages. In certain embodiments, modified oligonucleotides comprise one or more modified nucleoside comprising a modified sugar. In certain embodiments, modified oligonucleotides comprise one or more modified nucleosides comprising a modified nucleobase. In certain embodiments, modified oligonucleotides comprise one or more modified internucleoside linkage. In such embodiments, the modified, unmodified, and differently modified sugar moieties, nucleobases, and/or internucleoside linkages of a modified oligonucleotide define a pattern or motif. In certain embodiments, the patterns of sugar moieties, nucleobases, and internucleoside linkages are each independent of one another. Thus, a modified oligonucleotide may be described by its sugar motif, nucleobase motif and/or internucleoside linkage motif (as used herein, nucleobase motif describes the modifications to the nucleobases independent of the sequence of nucleobases).

1. Certain Sugar Motifs

In certain embodiments, compounds described herein comprise oligonucleotides. In certain embodiments, oligonucleotides comprise one or more type of modified sugar and/or unmodified sugar moiety arranged along the oligonucleotide or region thereof in a defined pattern or sugar motif. In certain instances, such sugar motifs include but are not limited to any of the sugar modifications discussed herein.

In certain embodiments, modified oligonucleotides comprise or consist of a region having a gapmer motif, which comprises two external regions or "wings" and a central or internal region or "gap." The three regions of a gapmer motif (the 5'-wing, the gap, and the 3'-wing) form a contiguous sequence of nucleosides wherein at least some of the sugar moieties of the nucleosides of each of the wings differ from at least some of the sugar moieties of the nucleosides of the gap. Specifically, at least the sugar moieties of the nucleosides of each wing that are closest to the gap (the 3'-most nucleoside of the 5'-wing and the 5'-most nucleoside of the 3'-wing) differ from the sugar moiety of the neighboring gap nucleosides, thus defining the boundary between the wings and the gap (i.e., the wing/gap junction). In certain embodiments, the sugar moieties within the gap are the same as one another. In certain embodiments, the gap includes one or more nucleoside having a sugar moiety that differs from the sugar moiety of one or more other nucleosides of the gap. In certain embodiments, the sugar motifs of the two wings are the same as one another (symmetric gapmer). In certain embodiments, the sugar motif of the 5'-wing differs from the sugar motif of the 3'-wing (asymmetric gapmer).

In certain embodiments, the wings of a gapmer comprise 1-5 nucleosides. In certain embodiments, the wings of a gapmer comprise 2-5 nucleosides. In certain embodiments, the wings of a gapmer comprise 3-5 nucleosides. In certain embodiments, the nucleosides of a gapmer are all modified nucleosides.

In certain embodiments, the gap of a gapmer comprises 7-12 nucleosides. In certain embodiments, the gap of a gapmer comprises 7-10 nucleosides. In certain embodiments, the gap of a gapmer comprises 8-10 nucleosides. In certain embodiments, the gap of a gapmer comprises 10 nucleosides. In certain embodiment, each nucleoside of the gap of a gapmer is an unmodified 2'-deoxy nucleoside.

In certain embodiments, the gapmer is a deoxy gapmer. In such embodiments, the nucleosides on the gap side of each wing/gap junction are unmodified 2'-deoxy nucleosides and the nucleosides on the wing sides of each wing/gap junction are modified nucleosides. In certain such embodiments, each nucleoside of the gap is an unmodified 2'-deoxy nucleoside. In certain such embodiments, each nucleoside of each wing is a modified nucleoside.

In certain embodiments, a modified oligonucleotide has a fully modified sugar motif wherein each nucleoside of the modified oligonucleotide comprises a modified sugar moiety. In certain embodiments, modified oligonucleotides comprise or consist of a region having a fully modified sugar motif wherein each nucleoside of the region comprises a modified sugar moiety. In certain embodiments, modified oligonucleotides comprise or consist of a region having a fully modified sugar motif, wherein each nucleoside within the fully modified region comprises the same modified sugar moiety, referred to herein as a uniformly modified sugar motif. In certain embodiments, a fully modified oligonucleotide is a uniformly modified oligonucleotide. In certain embodiments, each nucleoside of a uniformly modified comprises the same 2'-modification.

2. Certain Nucleobase Motifs

In certain embodiments, compounds described herein comprise oligonucleotides. In certain embodiments, oligonucleotides comprise modified and/or unmodified nucleobases arranged along the oligonucleotide or region thereof in a defined pattern or motif. In certain embodiments, each nucleobase is modified. In certain embodiments, none of the nucleobases are modified. In certain embodiments, each purine or each pyrimidine is modified. In certain embodiments, each adenine is modified. In certain embodiments, each guanine is modified. In certain embodiments, each thymine is modified. In certain embodiments, each uracil is modified. In certain embodiments, each cytosine is modified. In certain embodiments, some or all of the cytosine nucleobases in a modified oligonucleotide are 5-methylcytosines.

In certain embodiments, modified oligonucleotides comprise a block of modified nucleobases. In certain such embodiments, the block is at the 3'-end of the oligonucleotide. In certain embodiments the block is within 3 nucleosides of the 3'-end of the oligonucleotide. In certain embodiments, the block is at the 5'-end of the oligonucleotide. In certain embodiments the block is within 3 nucleosides of the 5'-end of the oligonucleotide.

In certain embodiments, oligonucleotides having a gapmer motif comprise a nucleoside comprising a modified nucleobase. In certain such embodiments, one nucleoside comprising a modified nucleobase is in the central gap of an oligonucleotide having a gapmer motif. In certain such embodiments, the sugar moiety of said nucleoside is a 2'-deoxyribosyl moiety. In certain embodiments, the modified nucleobase is selected from: a 2-thiopyrimidine and a 5-propynepyrimidine.

3. Certain Internucleoside Linkage Motifs

In certain embodiments, compounds described herein comprise oligonucleotides. In certain embodiments, oligonucleotides comprise modified and/or unmodified internucleoside linkages arranged along the oligonucleotide or region thereof in a defined pattern or motif. In certain embodiments, essentially each internucleoside linking group is a phosphate internucleoside linkage (P=O). In certain embodiments, each internucleoside linking group of a modified oligonucleotide is a phosphorothioate (P=S). In certain embodiments, each internucleoside linking group of a modified oligonucleotide is independently selected from a phosphorothioate and phosphate internucleoside linkage. In certain embodiments, the sugar motif of a modified oligonucleotide is a gapmer and the internucleoside linkages within the gap are all modified. In certain such embodiments, some or all of the internucleoside linkages in the wings are unmodified phosphate linkages. In certain embodiments, the terminal internucleoside linkages are modified.

Certain Modified Oligonucleotides

In certain embodiments, compounds described herein comprise modified oligonucleotides. In certain embodiments, the above modifications (sugar, nucleobase, internucleoside linkage) are incorporated into a modified oligonucleotide. In certain embodiments, modified oligonucleotides are characterized by their modification, motifs, and overall lengths. In certain embodiments, such parameters are each independent of one another. Thus, unless otherwise indicated, each internucleoside linkage of an oligonucleotide having a gapmer sugar motif may be modified or unmodified and may or may not follow the gapmer modification pattern of the sugar modifications. For example, the internucleoside linkages within the wing regions of a sugar gapmer may be the same or different from one another and may be the same or different from the internucleoside linkages of the gap region of the sugar motif. Likewise, such gapmer oligonucleotides may comprise one or more modified nucleobase independent of the gapmer pattern of the sugar modifications. Furthermore, in certain instances, an oligonucleotide is described by an overall length or range and by lengths or length ranges of two or more regions (e.g., a regions of nucleosides having specified sugar modifications), in such circumstances it may be possible to select numbers for each range that result in an oligonucleotide having an overall length falling outside the specified range. In such circumstances, both elements must be satisfied. For example, in certain embodiments, a modified oligonucleotide consists of 15-20 linked nucleosides and has a sugar motif consisting of three regions, A, B, and C, wherein region A consists of 2-6 linked nucleosides having a specified sugar motif, region B consists of 6-10 linked nucleosides having a specified sugar motif, and region C consists of 2-6 linked nucleosides having a specified sugar motif. Such embodiments do not include modified oligonucleotides where A and C each consist of 6 linked nucleosides and B consists of 10 linked nucleosides (even though those numbers of nucleosides are permitted within the requirements for A, B, and C) because the overall length of such oligonucleotide is 22, which exceeds the upper limit of the overall length of the modified oligonucleotide (20). Herein, if a description of an oligonucleotide is silent with respect to one or more parameter, such parameter is not limited. Thus, a modified oligonucleotide described only as having a gapmer sugar motif without further description may have any length, internucleoside linkage motif, and nucleobase motif. Unless otherwise indicated, all modifications are independent of nucleobase sequence.

Certain Conjugated Compounds

In certain embodiments, the compounds described herein comprise or consist of an oligonucleotide (modified or unmodified) and optionally one or more conjugate groups and/or terminal groups. Conjugate groups consist of one or more conjugate moiety and a conjugate linker which links the conjugate moiety to the oligonucleotide. Conjugate groups may be attached to either or both ends of an oligonucleotide and/or at any internal position. In certain embodiments, conjugate groups are attached to the 2'-position of a nucleoside of a modified oligonucleotide. In certain embodiments, conjugate groups that are attached to either or both ends of an oligonucleotide are terminal groups. In certain such embodiments, conjugate groups or terminal groups are attached at the 3' and/or 5'-end of oligonucleotides. In certain such embodiments, conjugate groups (or terminal groups) are attached at the 3'-end of oligonucleotides. In certain embodiments, conjugate groups are attached near the 3'-end of oligonucleotides. In certain embodiments, conjugate groups (or terminal groups) are attached at the 5'-end of oligonucleotides. In certain embodiments, conjugate groups are attached near the 5'-end of oligonucleotides.

In certain embodiments, the oligonucleotide of a compound is modified. In certain embodiments, the oligonucleotide of a compound may have any nucleobase sequence. In certain embodiments, the oligonucleotide of a compound has a nucleobase sequence that is complementary to a target nucleic acid. In certain embodiments, oligonucleotides are complementary to a messenger RNA (mRNA). In certain embodiments, oligonucleotides are complementary to a sense transcript.

Examples of terminal groups include but are not limited to conjugate groups, capping groups, phosphate moieties, protecting groups, modified or unmodified nucleosides, and two or more nucleosides that are independently modified or unmodified.

A. Certain Conjugate Groups

In certain embodiments, oligonucleotides are covalently attached to one or more conjugate groups. In certain embodiments, conjugate groups modify one or more properties of the attached oligonucleotide, including but not limited to pharmacodynamics, pharmacokinetics, stability, binding, absorption, tissue distribution, cellular distribution, cellular uptake, charge and clearance. In certain embodiments, conjugate groups impart a new property on the attached oligonucleotide, e.g., fluorophores or reporter groups that enable detection of the oligonucleotide.

Certain conjugate groups and conjugate moieties have been described previously, for example: cholesterol moiety (Letsinger et al., *Proc. Natl. Acad. Sci. USA,* 1989, 86, 6553-6556), cholic acid (Manoharan et al., *Bioorg. Med. Chem. Lett.,* 1994, 4, 1053-1060), a thioether, e.g., hexyl-S-tritylthiol (Manoharan et al., *Ann. N.Y. Acad. Sci.,* 1992, 660, 306-309; Manoharan et al., *Bioorg. Med. Chem. Lett.,* 1993, 3, 2765-2770), a thiocholesterol (Oberhauser et al., *Nucl. Acids Res.,* 1992, 20, 533-538), an aliphatic chain, e.g., do-decan-diol or undecyl residues (Saison-Behmoaras et al., *EMBO J.,* 1991, 10, 1111-1118; Kabanov et al., *FEBS Lett.,* 1990, 259, 327-330; Svinarchuk et al., *Biochimie,* 1993, 75, 49-54), a phospholipid, e.g., di-hexadecyl-rac-glycerol or triethyl-ammonium 1,2-di-O-hexadecyl-rac-glycero-3-H-phosphonate (Manoharan et al., *Tetrahedron Lett.,* 1995, 36, 3651-3654; Shea et al., *Nucl. Acids Res.,* 1990, 18, 3777-3783), a polyamine or a polyethylene glycol chain (Manoharan et al., *Nucleosides & Nucleotides,* 1995, 14, 969-973), or adamantane acetic acid, a palmityl moiety (Mishra et al., *Biochim. Biophys. Acta,* 1995, 1264, 229-237), an octadecylamine or hexylamino-carbonyl-oxycholesterol moiety (Crooke et al., *J. Pharmacol. Exp. Ther.,* 1996, 277, 923-937), a tocopherol group (Nishina et al., *Molecular Therapy Nucleic Acids,* 2015, 4, e220; doi:10.1038/mtna.2014.72 and Nishina et al., *Molecular Therapy,* 2008, 16, 734-740), or a GalNAc cluster (e.g., WO2014/179620).

1. Conjugate Moieties

Conjugate moieties include, without limitation, intercalators, reporter molecules, polyamines, polyamides, peptides, carbohydrates (e.g., GalNAc), vitamin moieties, polyethylene glycols, thioethers, polyethers, cholesterols, thiocholesterols, cholic acid moieties, folate, lipids, phospholipids, biotin, phenazine, phenanthridine, anthraquinone, adamantane, acridine, fluoresceins, rhodamines, coumarins, fluorophores, and dyes.

In certain embodiments, a conjugate moiety comprises an active drug substance, for example, aspirin, warfarin, phenylbutazone, ibuprofen, suprofen, fen-bufen, ketoprofen, (S)-(+)-pranoprofen, carprofen, dansylsarcosine, 2,3,5-triiodobenzoic acid, fingolimod, flufenamic acid, folinic acid, a benzothiadiazide, chlorothiazide, a diazepine, indomethicin, a barbiturate, a cephalosporin, a sulfa drug, an antidiabetic, an antibacterial or an antibiotic.

2. Conjugate Linkers

Conjugate moieties are attached to oligonucleotides through conjugate linkers. In certain compounds, a conjugate group is a single chemical bond (i.e. conjugate moiety is attached to an oligonucleotide via a conjugate linker through a single bond). In certain embodiments, the conjugate linker comprises a chain structure, such as a hydrocarbyl chain, or an oligomer of repeating units such as ethylene glycol, nucleosides, or amino acid units.

In certain embodiments, a conjugate linker comprises one or more groups selected from alkyl, amino, oxo, amide, disulfide, polyethylene glycol, ether, thioether, and hydroxylamino. In certain such embodiments, the conjugate linker comprises groups selected from alkyl, amino, oxo, amide and ether groups. In certain embodiments, the conjugate linker comprises groups selected from alkyl and amide groups. In certain embodiments, the conjugate linker comprises groups selected from alkyl and ether groups. In certain embodiments, the conjugate linker comprises at least one phosphorus moiety. In certain embodiments, the conjugate linker comprises at least one phosphate group. In certain embodiments, the conjugate linker includes at least one neutral linking group.

In certain embodiments, conjugate linkers, including the conjugate linkers described above, are bifunctional linking moieties, e.g., those known in the art to be useful for attaching conjugate groups to parent compounds, such as the oligonucleotides provided herein. In general, a bifunctional linking moiety comprises at least two functional groups. One of the functional groups is selected to bind to a particular site on a compound and the other is selected to bind to a conjugate group. Examples of functional groups used in a bifunctional linking moiety include but are not limited to electrophiles for reacting with nucleophilic groups and nucleophiles for reacting with electrophilic groups. In certain embodiments, bifunctional linking moieties comprise one or more groups selected from amino, hydroxyl, carboxylic acid, thiol, alkyl, alkenyl, and alkynyl.

Examples of conjugate linkers include but are not limited to pyrrolidine, 8-amino-3,6-dioxaoctanoic acid (ADO), succinimidyl 4-(N-maleimidomethyl) cyclohexane-1-carboxylate (SMCC) and 6-aminohexanoic acid (AHEX or AHA). Other conjugate linkers include but are not limited to substituted or unsubstituted $C_1$-$C_{10}$ alkyl, substituted or unsubstituted $C_2$-$C_{10}$ alkenyl or substituted or unsubstituted $C_2$-$C_{10}$ alkynyl, wherein a nonlimiting list of preferred substituent groups includes hydroxyl, amino, alkoxy, carboxy, benzyl, phenyl, nitro, thiol, thioalkoxy, halogen, alkyl, aryl, alkenyl and alkynyl.

In certain embodiments, conjugate linkers comprise 1-10 linker-nucleosides. In certain embodiments, such linker-nucleosides are modified nucleosides. In certain embodiments such linker-nucleosides comprise a modified sugar moiety. In certain embodiments, linker-nucleosides are unmodified. In certain embodiments, linker-nucleosides comprise an optionally protected heterocyclic base selected from a purine, substituted purine, pyrimidine or substituted pyrimidine. In certain embodiments, a cleavable moiety is a nucleoside selected from uracil, thymine, cytosine, 4-N-benzoylcytosine, 5-methylcytosine, 4-N-benzoyl-5-methylcytosine, adenine, 6-N-benzoyladenine, guanine and 2-N-isobutyrylguanine. It is typically desirable for linker-nucleosides to be cleaved from the compound after it reaches a target tissue. Accordingly, linker-nucleosides are typically linked to one another and to the remainder of the compound through cleavable bonds. In certain embodiments, such cleavable bonds are phosphodiester bonds.

Herein, linker-nucleosides are not considered to be part of the oligonucleotide. Accordingly, in embodiments in which a compound comprises an oligonucleotide consisting of a specified number or range of linked nucleosides and/or a specified percent complementarity to a reference nucleic acid and the compound also comprises a conjugate group comprising a conjugate linker comprising linker-nucleosides, those linker-nucleosides are not counted toward the length of the oligonucleotide and are not used in determining the percent complementarity of the oligonucleotide for the reference nucleic acid. For example, a compound may comprise (1) a modified oligonucleotide consisting of 8-30 nucleosides and (2) a conjugate group comprising 1-10 linker-nucleosides that are contiguous with the nucleosides of the modified oligonucleotide. The total number of contiguous linked nucleosides in such a compound is more than 30. Alternatively, a compound may comprise a modified oligonucleotide consisting of 8-30 nucleosides and no conjugate group. The total number of contiguous linked nucleosides in such a compound is no more than 30. Unless otherwise indicated conjugate linkers comprise no more than 10 linker-nucleosides. In certain embodiments, conjugate linkers comprise no more than 5 linker-nucleosides. In certain embodiments, conjugate linkers comprise no more than 3 linker-nucleosides. In certain embodiments, conjugate linkers comprise no more than 2 linker-nucleosides. In certain embodiments, conjugate linkers comprise no more than 1 linker-nucleoside.

In certain embodiments, it is desirable for a conjugate group to be cleaved from the oligonucleotide. For example, in certain circumstances compounds comprising a particular conjugate moiety are better taken up by a particular cell type, but once the compound has been taken up, it is desirable that the conjugate group be cleaved to release the unconjugated or parent oligonucleotide. Thus, certain conjugate may comprise one or more cleavable moieties, typically within the conjugate linker. In certain embodiments, a cleavable moiety is a cleavable bond. In certain embodiments, a cleavable moiety is a group of atoms comprising at least one cleavable bond. In certain embodiments, a cleavable moiety comprises a group of atoms having one, two, three, four, or more than four cleavable bonds. In certain embodiments, a cleavable moiety is selectively cleaved inside a cell or subcellular compartment, such as a lysosome. In certain embodiments, a cleavable moiety is selectively cleaved by endogenous enzymes, such as nucleases.

In certain embodiments, a cleavable bond is selected from among: an amide, an ester, an ether, one or both esters of a phosphodiester, a phosphate ester, a carbamate, or a disulfide. In certain embodiments, a cleavable bond is one or both of the esters of a phosphodiester. In certain embodiments, a cleavable moiety comprises a phosphate or phosphodiester. In certain embodiments, the cleavable moiety is a phosphate linkage between an oligonucleotide and a conjugate moiety or conjugate group.

In certain embodiments, a cleavable moiety comprises or consists of one or more linker-nucleosides. In certain such embodiments, one or more linker-nucleosides are linked to one another and/or to the remainder of the compound through cleavable bonds. In certain embodiments, such cleavable bonds are unmodified phosphodiester bonds. In certain embodiments, a cleavable moiety is 2'-deoxy nucleoside that is attached to either the 3' or 5'-terminal nucleoside of an oligonucleotide by a phosphate internucleoside linkage and covalently attached to the remainder of the conjugate linker or conjugate moiety by a phosphate or phosphorothioate linkage. In certain such embodiments, the cleavable moiety is 2'-deoxyadenosine.

Compositions and Methods for Formulating Pharmaceutical Compositions

Compounds described herein may be admixed with pharmaceutically acceptable active or inert substances for the preparation of pharmaceutical compositions or formulations. Compositions and methods for the formulation of pharmaceutical compositions are dependent upon a number of criteria, including, but not limited to, route of administration, extent of disease, or dose to be administered.

In certain embodiments, the present invention provides pharmaceutical compositions comprising one or more compounds or a salt thereof. In certain embodiments, the compounds are antisense compounds or oligomeric compounds. In certain embodiments, the compounds comprise or consist of a modified oligonucleotide. In certain such embodiments, the pharmaceutical composition comprises a suitable pharmaceutically acceptable diluent or carrier. In certain embodiments, a pharmaceutical composition comprises a sterile saline solution and one or more compound. In certain embodiments, such pharmaceutical composition consists of a sterile saline solution and one or more compound. In certain embodiments, the sterile saline is pharmaceutical grade saline. In certain embodiments, a pharmaceutical composition comprises one or more compound and sterile water. In certain embodiments, a pharmaceutical composition consists of one compound and sterile water. In certain embodiments, the sterile water is pharmaceutical grade water. In certain embodiments, a pharmaceutical composition comprises one or more compound and phosphate-buffered saline (PBS). In certain embodiments, a pharmaceutical composition consists of one or more compound and sterile PBS. In certain embodiments, the sterile PBS is pharmaceutical grade PBS. Compositions and methods for the formulation of pharmaceutical compositions are dependent upon a number of criteria, including, but not limited to, route of administration, extent of disease, or dose to be administered.

A compound described herein targeted to a KEAP1 nucleic acid can be utilized in pharmaceutical compositions by combining the compound with a suitable pharmaceutically acceptable diluent or carrier. In certain embodiments, a pharmaceutically acceptable diluent is water, such as sterile water suitable for injection. Accordingly, in one embodiment, employed in the methods described herein is a pharmaceutical composition comprising a compound targeted to a KEAP1 nucleic acid and a pharmaceutically acceptable diluent. In certain embodiments, the pharmaceutically acceptable diluent is water. In certain embodiments, the compound comprises or consists of a modified oligonucleotide provided herein.

Pharmaceutical compositions comprising compounds provided herein encompass any pharmaceutically acceptable salts, esters, or salts of such esters, or any other oligonucleotide which, upon administration to an animal, including a human, is capable of providing (directly or indirectly) the biologically active metabolite or residue thereof. In certain embodiments, the compounds are antisense compounds or oligomeric compounds. In certain embodiments, the compound comprises or consists of a modified oligonucleotide. Accordingly, for example, the disclosure is also drawn to pharmaceutically acceptable salts of compounds, prodrugs, pharmaceutically acceptable salts of such prodrugs, and other bioequivalents. Suitable pharmaceutically acceptable salts include, but are not limited to, sodium and potassium salts.

A prodrug can include the incorporation of additional nucleosides at one or both ends of a compound which are cleaved by endogenous nucleases within the body, to form the active compound.

In certain embodiments, the compounds or compositions further comprise a pharmaceutically acceptable carrier or diluent.

RNA-Sequencing

Total RNA was isolated either directly from cryosections of the tumor tissue or from organotypic epithelial cultures using TRIzol (Life Technologies) according to the manufacturer's instructions. For tissue sections, the tumors were embedded in OCT and cryosectioned. Sections from the middle of the tumor were stained using toluidine blue (Sigma) and assayed regarding the homogeneity of the section. Homogenous 30 μm sections comprising >90% malignant cells were immediately dispersed and homogenized in TRIzol. RNA quality was assayed by running an RNA 6000 Nano chip on a 2100 Bioanalyzer (Agilent). For high-throughput sequencing, RNA samples were required to have an RNA integrity number (RIN)≥9. TruSeq (Illumina) libraries for polyA+RNA-Seq were prepared from 0.5-1 μg RNA per sample. To ensure efficient cluster generation, an additional gel purification step of the libraries was applied. The libraries were multiplexed (4-6 libraries per lane) and sequenced paired-end 101 bp on the HiSeq2000 platform (Illumina), resulting in on average 40 Mio reads per library.

Advantages of the Invention

Provided herein are methods and compositions for the modulation of KEAP1 that can treat, prevent and/or ameliorate an oxidative stress related disease, disorder and/or condition such as metabolic disease (e.g., insulin resistance, metabolic syndrome), NASH and NAFLD. In a particular embodiment, provided are KEAP1 antisense oligonucleotides to treat, prevent and/or ameliorate a KEAP1 pathway related disease, disorder and/or condition or symptoms thereof as described herein.

KEAP1 functions as an important regulator of cellular antioxidant responses via its interactions with multiple substrates such as NRF2 and PGAM5. KEAP1 binding of its substrates sequesters the substrates in the cytoplasm and targets them for ubiquitination and degradation. In the presence of oxidative stress, KEAP1 releases its substrate which then can initiate multiple antioxidant response pathways.

Currently, commercially available therapies targeting various oxidative stress components (e.g., antioxidants) have been ineffective in completely inhibiting or blocking the oxidative stress pathways. The mechanism(s) for this ineffective inhibition has not been fully elucidated. An antisense oligonucleotide targeting KEAP1 may block multiple oxidative stress pathways due to its interactions with multiple substrates that respond to oxidative stress by different pathways. Accordingly, KEAP1 inhibition may not be susceptible to the mechanisms confounding commercially approved therapies for oxidative stress. Therefore, a KEAP1 antisense oligonucleotide may provide superior therapeutic efficacy over the current commercial therapeutics used to treat, prevent and/or ameliorate oxidative stress in a subject, especially those subject suffering from fatty liver disease (e.g., hepatic steatosis, steatohepatitis, NASH, NAFLD, inflammation (e.g., asthma, COPD, airway hyperresponsiveness, renal inflammation, pulmonary inflammation, liver inflammation), fibrosis (e.g., pulmonary fibrosis, renal fibrosis, cystic fibrosis, liver fibrosis), cancer, age-related macular degeneration, atherosclerosis, hyperlipidemia, neurologic disorders, and/or a metabolic disease, disorder or condition such as metabolic syndrome, type 2 diabetes, diabetic nephropathy, diabetic cardiomyopathy, and insulin resistance.

Another advantage of KEAP1 ASO therapy is that it impacts the heart less than bardoxolone methyl treatment. Thus, KEAP1 ASO treatment may not have the adverse effects on the heart as seen after bardoxolone methyl treatment.

Another advantage of using a KEAP1 antisense oligonucleotide to combat oxidative stress is that it can be used in combination with commercially available antioxidants to provide an additive therapeutic effect.

Further, the antisense oligonucleotide targeting KEAP1 has been shown to localize to and decrease KEAP1 in multiple organs such as the lungs, liver and kidney. An ability to decrease KEAP1 in the liver tissue indicates that the oligonucleotide can target and inhibit the main source of KEAP1 production and also indicates that a KEAP1 antisense oligonucleotide can be useful in treating liver related diseases such as liver or hepatic fibrosis, cystic fibrosis, hepatic inflammation, steatohepatitis (e.g., NASH), hepatic fibrosis (e.g., NAFLD), hepatic cancer, and the like. An ability to decrease KEAP1 in the kidney tissue indicates that KEAP1 antisense oligonucleotide therapy can be useful in treating kidney related diseases such as nepthropathy (e.g., diabetic nephropathy), renal cancer, renal fibrosis, renal inflammation, cystic fibrosis and other renal diseases with an oxidative stress component. An ability to decrease KEAP1 in the lung tissue indicates that KEAP1 antisense oligonucleotide therapy can be useful in treating lung related diseases such as pulmonary inflammation, pulmonary fibrosis, cystic fibrosis, asthma, COPD, airway hyperresponsiveness and the like.

Reducing KEAP1, and therefore increasing multiple antioxidant pathways (e.g., via NRF2 and PGAM5), may be the most efficacious means of treating oxidative stress.

Examples

Non-Limiting Disclosure and Incorporation by Reference

While certain compounds, compositions and methods described herein have been described with specificity in accordance with certain embodiments, the following examples serve only to illustrate the compounds described herein and are not intended to limit the same. Each of the references recited in the present application is incorporated herein by reference in its entirety.

Example 1: Antisense Oligonucleotides Targeting Murine KEAP1

Newly designed chimeric antisense oligonucleotides (ASOs) targeting KEAP1 were designed as 16 nucleobase long oligonucleotides with a 3-10-3 cEt gapmer motif, wherein a gap segment consisting of ten linked deoxynucleosides is flanked by 5' and 3' wing segments each consisting of three linked nucleosides, wherein each nucleoside of each wing segment comprises a cEt sugar, wherein each internucleoside linkage is a phosphorothioate linkage and wherein each cytosine residue is a 5-methylcytosine. Three potent ASOs identified in an in vitro screen are listed in the table below: ISIS 645938, ISIS 645954 and ISIS 645958.

"Start site" indicates the 5'-most nucleoside to which the chimeric antisense oligonucleotide is targeted in the murine gene sequence. "Stop site" indicates the 3'-most nucleoside to which the chimeric antisense oligonucleotide is targeted in the murine gene sequence. Each ASO listed in the table below is targeted to murine KEAP1 mRNA, designated herein as SEQ ID NO: 5 (GENBANK Accession Number NM_016679.4) and/or the murine KEAP1 genomic sequence, designated herein as SEQ ID NO: 6 (the complement of GENBANK Accession Number NC_000075.6 truncated from nucleotide 21227001 to 21242000). In the table below, 'n/a' indicates that the ASO does not target that particular sequence with 100% complementarity.

TABLE 1

In vitro ASO inhibition of mouse KEAP1

| ISIS NO | SEQ ID NO: 5 Start Site | SEQ ID NO: 5 Stop Site | SEQ ID NO: 6 Start Site | SEQ ID NO: 6 Stop Site | Sequence | Chemistry | IC50 uM | SEQ ID NO |
|---|---|---|---|---|---|---|---|---|
| 645938 | n/a | n/a | 6587 | 6602 | TATTCAGAATGCAGTC | kkk-d10-kkk | 1.7 | 7 |
| 645954 | 1106 | 1121 | 3774 | 3789 | ACATGTCAGATTCCTT | kkk-d10-kkk | 2.0 | 8 |
| 645958 | 1353 | 1368 | 4021 | 4036 | AATGATATCTAAGTGC | kkk-d10-kkk | 1.5 | 9 |

Example 2: Dose-Dependent ASO Inhibition of KEAP1 in Wild Type Mice

The three potent ASOs identified in by an in vitro screen above were assessed in a dose-dependent assay in C57 wildtype mice fed a normal chow diet (D12451 Research Diets, New Brunswick, N.J.) to test their potency in vivo.

Treatment

C57BL/6 wildtype mice were divided into treatment groups consisting of six animals. Mice were injected intraperitoneally with 10 mg/kg, 25 mg/kg or 40 mg/kg of ASO as specified in the table below once a week for four weeks. 40 mg/kg of ISIS 549144 (a 3-10-3 cEt gapmer having the sequence GGCCAATACGCCGTCA, incorporated herein as SEQ ID NO: 10) was used as an antisense control, and PBS alone was used as a control to which the ASO-treated groups were compared. Several clinical endpoints were measured over the course of the study. The body weights were measured weekly, tail bleeds were performed at baseline and weekly thereafter, as well as at the time of sacrifice. The mice were euthanized 24 hours after the last dose; organs and plasma were harvested for further analysis.

RNA Analysis

At the end of the treatment period, RNA was extracted from liver, kidney and white adipose tissue (WAT) for quantitative real-time PCR analysis of RNA expression of KEAP1. Murine KEAP1 primer probe set RTS4398_MGB (forward sequence AAGGTCATGGAAAGGCTTATTGAGT, designated herein as SEQ ID NO: 12; reverse sequence GTTCATCACGTGCAGGACACA, designated herein as SEQ ID NO: 13; probe sequence TCTCCGTGGGCGAGAA, designated herein as SEQ ID NO: 14) was used to measure RNA levels. Results are presented in the table below as percent inhibition of KEAP1, relative to PBS control, normalized against Cyclophilin A. Treatment with the KEAP ASOs resulted in significant dose-dependent reductions of KEAP1 in the liver in comparison to the control ASO and the PBS control.

TABLE 2

ASO inhibition of KEAP1 RNA in organs of wild type mice

| Treatment (ISIS NO) | Dose (mg/kg) | % inhibition liver | % inhibition kidney | % inhibition WAT |
|---|---|---|---|---|
| saline | — | 0 | 0 | 0 |
| 549144 | 40 | 0 | 0 | 0 |
| 645938 | 40 | 91 | 66 | 70 |
|  | 25 | 82 | 66 | 61 |
|  | 10 | 47 | 57 | 56 |
| 645954 | 40 | 86 | 66 | 62 |
|  | 25 | 89 | 66 | 64 |
|  | 10 | 69 | 58 | 49 |
| 645958 | 40 | 83 | 53 | 62 |
|  | 25 | 67 | 51 | 58 |
|  | 10 | 42 | 52 | 48 |

Body and Organ Weights

Body weights were measured weekly, and kidney, liver, spleen and white adipose tissue (WAT) weights were measured at the end of the fourth week of the study. Averages for each treatment group are presented in grams in the table below. Generally, ISIS 645938 and ISIS 645958 did not increase body weight or organ weight.

TABLE 3

Weights (g) of body and organs of wild type mice after ASO treatment

| Treatment | Dose | Body | | | | | | | | |
|---|---|---|---|---|---|---|---|---|---|---|
| (ISIS NO) | (mg/kg) | wk 0 | wk 1 | wk 2 | wk 3 | wk 4 | liver | kidney | spleen | WAT |
| saline | — | 24 | 25 | 25 | 26 | 27 | 1.3 | 0.32 | 0.08 | 0.29 |
| 549144 | 40 | 23 | 24 | 25 | 25 | 26 | 1.4 | 0.32 | 0.08 | 0.33 |
| 645938 | 40 | 23 | 24 | 25 | 25 | 26 | 1.8 | 0.32 | 0.10 | 0.20 |
|  | 25 | 24 | 25 | 26 | 26 | 27 | 1.8 | 0.32 | 0.11 | 0.16 |
|  | 10 | 22 | 24 | 25 | 25 | 26 | 1.3 | 0.32 | 0.09 | 0.25 |
| 645954 | 40 | 23 | 24 | 24 | 25 | 25 | 2.6 | 0.32 | 0.08 | 0.16 |
|  | 25 | 24 | 25 | 26 | 26 | 27 | 2.2 | 0.35 | 0.09 | 0.18 |
|  | 10 | 24 | 25 | 26 | 27 | 27 | 1.6 | 0.35 | 0.09 | 0.23 |
| 645958 | 40 | 25 | 26 | 27 | 28 | 29 | 1.8 | 0.36 | 0.09 | 0.18 |
|  | 25 | 24 | 25 | 27 | 27 | 28 | 1.6 | 0.36 | 0.10 | 0.19 |
|  | 10 | 22 | 23 | 24 | 25 | 25 | 1.3 | 0.31 | 0.07 | 0.25 |

Plasma Chemistry Markers

To evaluate the effect of ASOs on plasma chemistry biomarkers, cardiac punctures were performed and plasma ALT, AST and other biomarkers were measured using an automated clinical chemistry analyzer (Hitachi Olympus AU400e, Melville, N.Y.). The averages for each treatment group are presented in the table below. Generally, ISIS 645938 and ISIS 645958 were found to be tolerable in the mice and these ASOs were used in later studies.

TABLE 4

Plasma biomarkers in wild type mice after ASO treatment

| Treatment (ISIS NO) | Dose (mg/kg) | ALT (U/L) | AST (U/L) | CHOL (mmol/L) | GLU (mg/dL) | HDL (mg/dL) | LDL (mg/dL) | TRIG (mmol/L) | NEFA | 3HB |
|---|---|---|---|---|---|---|---|---|---|---|
| saline | — | 31 | 46 | 81 | 266 | 66.0 | 18.1 | 101 | 0.27 | 218 |
| 549144 | 40 | 38 | 45 | 77 | 237 | 60.8 | 16.7 | 108 | 0.35 | 224 |
| 645938 | 40 | 36 | 61 | 88 | 255 | 66.3 | 23.7 | 89 | 0.36 | 141 |
|  | 25 | 75 | 122 | 99 | 249 | 72.7 | 25.3 | 97 | 0.34 | 167 |
|  | 10 | 42 | 69 | 79 | 255 | 62.4 | 16.9 | 78 | 0.39 | 165 |
| 645954 | 40 | 1305 | 972 | 125 | 190 | 71.2 | 52.8 | 163 | 0.46 | 193 |
|  | 25 | 140 | 105 | 111 | 266 | 83.3 | 29.0 | 114 | 0.46 | 170 |
|  | 10 | 47 | 101 | 96 | 263 | 76.7 | 19.9 | 78 | 0.44 | 163 |
| 645958 | 40 | 38 | 49 | 88 | 289 | 68.4 | 21.4 | 98 | 0.44 | 242 |
|  | 25 | 73 | 68 | 92 | 260 | 71.0 | 23.4 | 95 | 0.49 | 167 |
|  | 10 | 25 | 42 | 78 | 294 | 63.0 | 16.4 | 79 | 0.51 | 185 |

Protein Analysis

Under basal conditions, KEAP1 represses Nrf2 through its molecular interaction. However, in response to oxidative and xenobiotic stress, KEAP1 releases Nrf2 from the KEAP1/Nrf2 complex, allowing nuclear translocation of Nrf2, binding of Nrf2 to Antioxidant Response Elements (AREs) and initiating transcription of a battery of cytoprotective detoxifying and antioxidant genes including glutathione S-transferase alpha 1 (GSTA1) and NAD(P)H: Quinone Oxidoreductase 1 (NQO1).

Murine GSTA1 mRNA levels in wild type mouse liver and WAT samples were quantified using quantitative real-time PCR. GSTA1 mRNA expression was assessed using mouse primer probe set: mGsta1_LTS34766 (Forward Sequence: CCCCTTTCCCTCTGCTGAAG, designated herein as SEQ ID NO: 15; Reverse Sequence: TGCAGCTT-CACTGAATCTTGAAAG, designated herein as SEQ ID NO: 16; Probe Sequence: TTCCTTGCTTCTTGAAT-TTGTTTTGCATCCAT, designated herein as SEQ ID NO: 17).

The results are presented in the table below. The results indicate that treatment with ISIS 645938, 645954 or 645958 resulted in increased GSTA1 mRNA expression levels in both the liver and the WAT. The increase in GSTA1 suggests that ASO inhibition of KEAP1 expression increases Nrf2 activity and allows expression of ARE-containing genes such as GSTA1.

TABLE 5

Expression of GSTA1 in wildtype mice treated with ASOs

| Treatment | Dose | % saline | |
|---|---|---|---|
| (ISIS NO) | (mg/kg) | liver | WAT |
| saline | — | 100 | 100 |
| 549144 | 40 | 104 | 222 |
| 645938 | 40 | 1989 | 3039 |
|  | 25 | 1455 | 2122 |
|  | 10 | 329 | 1054 |

TABLE 5-continued

Expression of GSTA1 in wildtype mice treated with ASOs

| Treatment | Dose | % saline | |
|---|---|---|---|
| (ISIS NO) | (mg/kg) | liver | WAT |
| 645954 | 40 | 4454 | 8700 |
| | 25 | 2768 | 10250 |
| | 10 | 1326 | 1014 |
| 645958 | 40 | 910 | 2183 |
| | 25 | 493 | 1126 |
| | 10 | 342 | 154 |

NQO1 mRNA levels in wild type mouse liver, kidney and WAT were quantified using quantitative real-time PCR. NQO1 mRNA expression was assessed using mouse primer probe set: mNQO1_LTS00751 (Forward Sequence: CCTG-GAAGGATGGAAGAAACG, designated herein as SEQ ID NO: 18; Reverse Sequence: CAGGCTGCTTGGAGC-AAAAT, designated herein as SEQ ID NO: 19; Probe Sequence: AAACCGTCTGGGAGGAGACCCCACTX, designated herein as SEQ ID NO: 20, wherein X is a label).

Results are presented in the table below as percent saline. The results shown indicate that treatment with ISIS 645938, 645954 or 645958 resulted in dose dependent increases in NQO1 mRNA expression levels. The increase in NQO1 suggests that ASO inhibition of KEAP1 expression increases Nrf2 activity and allows expression of ARE-containing genes such as NQO1.

TABLE 6

Expression of NQO1 mRNA in wildtype mice treated with ASOs

| Treatment | Dose | % saline | | |
|---|---|---|---|---|
| (ISIS NO) | (mg/kg) | liver | Kidney | WAT |
| saline | — | 100 | 100 | 100 |
| 549144 | 40 | 119 | 108 | 105 |
| 645938 | 40 | 915 | 441 | 591 |
| | 25 | 594 | 396 | 545 |
| | 10 | 282 | 323 | 271 |
| 645954 | 40 | 2134 | 500 | 739 |
| | 25 | 1436 | 342 | 669 |
| | 10 | 490 | 325 | 379 |
| 645958 | 40 | 454 | 219 | 234 |
| | 25 | 303 | 231 | 204 |
| | 10 | 196 | 204 | 202 |

NQO1 Activity Assay

NQO1 activity was quantified in liver tissue homogenates using the Abcam NQO1 activity assay kit. Averages for each group are presented in the table below. The results show that NQO1 activity is increased after KEAP1 ASO treatment.

TABLE 7

Hepatic NQO1 activity in wild type mice treated with 40 mg/kg/wk of ASO

| Time | Treatment (ISIS NO) | | | |
|---|---|---|---|---|
| (sec) | saline | 549144 | 645938 | 645958 |
| 0 | 0 | 0 | 0 | 0 |
| 20 | 0.003 | 0.001 | 0.014 | 0.008 |
| 40 | 0.014 | −0.004 | 0.027 | 0.012 |
| 60 | 0.015 | −0.006 | 0.043 | 0.020 |
| 80 | 0.012 | 0.000 | 0.046 | 0.025 |
| 100 | 0.012 | 0.008 | 0.061 | 0.031 |
| 120 | 0.011 | 0.001 | 0.067 | 0.040 |
| 140 | 0.013 | 0.002 | 0.080 | 0.046 |
| 160 | 0.015 | 0.002 | 0.088 | 0.054 |
| 180 | 0.016 | 0.004 | 0.103 | 0.063 |
| 200 | 0.017 | 0.005 | 0.110 | 0.068 |
| 220 | 0.018 | 0.006 | 0.128 | 0.077 |
| 240 | 0.019 | 0.007 | 0.135 | 0.086 |
| 260 | 0.019 | 0.007 | 0.148 | 0.092 |
| 280 | 0.020 | 0.08 | 0.161 | 0.101 |
| 300 | 0.023 | 0.011 | 0.171 | 0.108 |

In chow fed wildtype mice, dose titration of KEAP1 ASOs (40, 25, and 10 mg/kg/wk) for four weeks led to dose-dependent decreases in hepatic KEAP1, reaching 90% at the highest dose when compared to saline controls. This reduction in KEAP1 led to significant increases in the hepatic expression of the ARE-containing genes NQO1 and GSTA1, reaching 915% and 1989%, respectively, at the highest dose versus saline controls. Furthermore, administration of the KEAP1 ASO did not produce significant changes in body weight or liver transaminases relative to control, indicating the ASOs were well tolerated.

Example 3: ASO Inhibition of KEAP1 in Diet-Induced Obesity (DIO) Mice

Frequently used in studies of diet-induced obesity (DIO), C57BL/6 mice (Jackson Laboratory, Bar Harbor, Me.) are vulnerable to the development of obesity when fed a high fat diet. ISIS 645938, exhibiting significant in vitro inhibition of murine KEAP1 RNA, was tested in a DIO mouse model.

Six week old test mice were fed a 60 kcal % high-fat diet (HFD) (D12492 Research Diets) for fifteen weeks, while six week old mice in three control groups (eight animals per group) were fed a normal chow diet, D12451 (a diet comprising 45 kcal % fat) or D12450B (a diet comprising 10 kcal % fat) for fifteen weeks.

Treatment

Treatment groups consisted of six to eight animals. Twenty-two week old male DIO mice ranging in weight from 36 g to 52 grams were continued on the high-fat diet for the duration of the study. ASOs were dissolved in 0.9% buffered saline (PBS) and sterilized by filtering through a 0.2 micron filter before injection in the mice.

The treatment groups were injected subcutaneously once a week for 6 weeks with the following:
1) 50 mg/kg of ISIS 645938 targeting murine KEAP1,
2) PBS solution, or
3) 50 mg/kg of control ASO ISIS 549144.

Several clinical endpoints were measured over the course of the study. The body and food weights were measured weekly, and tail bleeds were performed at baseline (after 15 weeks on HFD) and weekly thereafter, as well as at the time of sacrifice. The mice were euthanized 72 hours after the last dose (after 21-weeks on HFD) and after six-weeks of oligonucleotide treatment; organs and plasma were harvested for further analysis.

Plasma Chemistry Markers

To evaluate the effect of antisense oligonucleotides on several plasma chemistry markers (e.g. cholesterols, glucose, triglycerides and liver transaminases (alanine aminotransferase (ALT) and aspartate aminotransferase (AST)), blood and plasma levels were measured at various time points. The results are presented in the table below. "BL"=baseline after four-hour fast. For the 3-week time point, a 16-hour-fasted tail bleed was taken 24-hours after the third dose (after 18 weeks on HFD). For the 6-week time point, a 12-hour-fasted tail bleed was taken 24-hours after the sixth dose (after 21 weeks on HFD). "N/A"=data not available. Treatment with ISIS 645938 was tolerable in the mice with a transitory increase in ALT and AST levels that subsided by the sixth week.

TABLE 8

Plasma liver transaminases in ASO-treated DIO mice

| Diet and Treatment | | ALT (U/L) | | | AST (U/L) | |
|---|---|---|---|---|---|---|
| | BL | 3 wk. | 6 wk. | BL | 3 wk. | 6 wk. |
| PBS normal chow | 39 | 23 | 37 | 48 | 40 | 55 |
| PBS 10% fat D12450B | N/A | 23 | N/A | N/A | 50 | N/A |
| PBS 45% fat D12451 | N/A | 49 | N/A | N/A | 70 | N/A |
| HFD D12492 PBS | 44 | 69 | 104 | 52 | 87 | 110 |
| ISIS 549144 | 51 | 76 | 152 | 62 | 100 | 90 |
| ISIS 645938 | 33 | 205 | 93 | 54 | 197 | 117 |

Plasma levels of glucose ("GLU"), triglycerides ("TG"), total cholesterol ("TC") and HDL were measured at baseline, 3-week and 6-week time points using an automated clinical chemistry analyzer (Hitachi Olympus AU400e, Melville, N.Y.). The results are presented in the table below.

TABLE 9

Plasma chemistry markers in ASO-treated DIO mice

| Diet and Treatment | TC (mg/dL) | | | HDL (mg/dL) | | | GLU (mg/dL) | | | TG (mg/dL) | | |
|---|---|---|---|---|---|---|---|---|---|---|---|---|
| | BL | 3 wk | 6 wk | BL | 3 wk | 6 wk | BL | 3 wk | 6 wk | BL | 3 wk | 6 wk |
| PBS normal chow | 61 | 60 | 78 | 47 | 46 | 57 | 200 | 182 | 141 | 89 | 51 | 131 |
| PBS 10% fat D12450B | N/A | 121 | N/A | N/A | 96 | N/A | N/A | 148 | N/A | N/A | 84 | N/A |
| PBS 45% fat D12451 | N/A | 168 | N/A | N/A | 130 | N/A | N/A | 185 | N/A | N/A | 87 | N/A |
| HFD D12492 PBS | 171 | 193 | 213 | 134 | 149 | 174 | 254 | 190 | 197 | 85 | 110 | 98 |
| 549144 | 150 | 180 | 211 | 113 | 162 | 174 | 242 | 181 | 181 | 66 | 127 | 100 |
| 645938 | 161 | 251 | 199 | 128 | 181 | 151 | 238 | 188 | 169 | 75 | 134 | 90 |

Glucose Tolerance Test (GTT)

At the fourth week of treatment, 24 hours after treatment with the fourth dose of ASO or PBS and the DIO mice having fasted for 16 hours, 2 grams of glucose per kg body weight was administered intraperitonally and blood was drawn at various time points using a One Touch II™ glucose monitor for a Glucose Tolerance Test (GTT). As shown in the table below, ISIS 645938 treated mice were able to clear glucose at a higher rate than control treated mice, indicating an improving trend in glucose tolerance with ISIS 645938 treatment.

TABLE 10

GTT: Blood glucose levels (mg/dL) in ASO treated DIO mice

| Diet and Treatment | Time post glucose challenge (minutes) | | | | | |
|---|---|---|---|---|---|---|
| | 0 | 15 | 30 | 60 | 90 | 120 |
| PBS normal chow | 80 | 264 | 259 | 183 | 167 | 113 |
| PBS 10% fat D12450B | 91 | 281 | 294 | 201 | 140 | 143 |
| PBS 45% fat D12451 | 115 | 282 | 370 | 317 | 237 | 200 |
| HFD D12492 PBS | 162 | 344 | 362 | 298 | 247 | 217 |
| 549144 | 157 | 283 | 345 | 264 | 231 | 199 |
| 645938 | 157 | 299 | 287 | 210 | 190 | 168 |

Insulin Tolerance Test (ITT)

At the fifth week of treatment, 24 hours after treatment with the fifth dose of ASO or PBS and the DIO mice having fasted for four hours, 0.5 U human insulin per kg body weight was administered intraperitonally and blood was drawn at various time points using a One Touch II™ glucose monitor for an insulin tolerance test (ITT). As shown in the table below, blood glucose levels are reduced in DIO mice treated with ISIS 645938 indicating that treatment with a KEAP1 ASO had a tendency to improve insulin sensitivity in the mice.

TABLE 11

ITT: Blood glucose levels (mg/dL) in ASO-treated DIO mice

| Diet and Treatment | Time point (minutes) | | | | | | |
|---|---|---|---|---|---|---|---|
| | 0 | 15 | 30 | 45 | 60 | 90 | 120 |
| PBS normal chow | 135 | 113 | 99 | 118 | 141 | 167 | 170 |
| HFD D12492 PBS | 215 | 213 | 187 | 198 | 218 | 213 | 221 |
| 549144 | 176 | 178 | 152 | 161 | 178 | 177 | 172 |
| 645938 | 194 | 172 | 133 | 136 | 161 | 154 | 177 |

Body and Organ Weights

At the end of the study, 48 hours after treatment with the sixth dose of ASO or PBS, organs (liver, spleen, kidney)

were harvested, animals were euthanized, and blood was drawn for measure of various clinical parameters.

Body weights of the mice were measured each week and at the time of sacrifice ("Sac"), and are presented in the table below. Treatment with ISIS 645938 induced a downward trend in body weight over the course of treatment.

TABLE 12

Body weights (g) of DIO mice after ASO treatment

| ISIS NO | BL | Week 1 | Week 2 | Week 3 | Week 4 | Week 5 | Week 6 | Sac |
|---|---|---|---|---|---|---|---|---|
| PBS | 45 | 46 | 49 | 49 | 48 | 50 | 51 | 51 |
| 549144 | 44 | 45 | 47 | 48 | 50 | 50 | 51 | 51 |
| 645938 | 44 | 49 | 45 | 44 | 44 | 41 | 41 | 40 |

Kidney, liver and spleen weights were measured at the end of the study, and are presented as percent body weight (% BW) in the table below.

TABLE 13

Organ weights (g) of DIO mice after ASO treatment

| Diet and Treatment | | liver (% BW) | kidney (% BW) | spleen (% BW) |
|---|---|---|---|---|
| PBS normal chow | | 4.18 | 1.12 | 0.27 |
| HFD D12492 | PBS | 3.88 | 0.76 | 0.24 |
| | 549144 | 4.68 | 0.91 | 0.29 |
| | 645938 | 6.93 | 1.13 | 0.43 |

ELISA Assays

Insulin: An ALPCO Mouse Ultrasensitive Insulin ELISA kit (80-INSMSU-E01, E10) was used, without dilution, to measure plasma levels of insulin at baseline (BL) after a 4-hour fast, at three weeks after a 16-hour fast and at six weeks after a 16-hour fast, as shown in the table below. Treatment with ISIS 645938 decreased insulin and maintained similar glucose levels over the course of treatment when compared to control ASO indicating an improvement in insulin sensitivity.

TABLE 14

Plasma levels of insulin (ng/mL) in DIO mice after ASO treatment

| Diet and Treatment | | BL | 3 wks | 6 wks |
|---|---|---|---|---|
| PBS normal chow | | 1.63 | 0.32 | 1.07 |
| HFD D12492 | PBS | 13.23 | 1.85 | 2.93 |
| | 549144 | 9.88 | 1.69 | 1.69 |
| | 645938 | 8.52 | 0.98 | 0.65 |

Leptin: A Quantikine Mouse/Rat Leptin ELISA kit (M0B00) was used at a 1:20 dilution to measure plasma Leptin levels, as shown in the table below. 48-hours after the sixth dose, leptin was measured. Leptin was decreased after treatment with ISIS 645938, indicating an improvement in leptin sensitivity. Generally, a reduction in leptin is associated with improvements in obesity and metabolic syndrome.

Adiponectin: A Quantikine Mouse Adiponectin/Acrp30 ELISA kit (MRP300) was used at a 1:2000 dilution, as shown in the table below. 48-hours after the sixth dose, adiponectin was measured. Adiponectin was not changed after treatment with ISIS 645938.

TABLE 15

Plasma Leptin and Adiponectin (ng/mL) in DIO mice after ASO treatment

| Diet and Treatment | | Leptin | Adiponectin |
|---|---|---|---|
| PBS normal chow | | 6 | 12 |
| HFD D12492 | PBS | 103 | 13 |
| | 549144 | 76 | 12 |
| | 645938 | 27 | 14 |

KEAP1 Expression Analysis in the Organs:

Expression levels of KEAP1 in DIO mouse liver, fat, quadriceps muscle and pancreas were determined using real-time PCR and RIBOGREEN® RNA quantification reagent (Molecular Probes, Inc. Eugene, Oreg.) according to standard protocols. RNA was isolated from each organ using standard protocols, and a murine KEAP1 primer probe set RTS4398_MGB was used to measure mRNA levels in the organs harvested from ASO-treated DIO mice. KEAP1 RNA levels were determined relative to total RNA using RIBOGREEN® prior to normalization to PBS-treated control. The results are presented in the table below as the average percent inhibition of KEAP1 RNA levels for each treatment group, relative to PBS-treated control and are denoted as "% inhibition." ISIS 645938 strongly inhibited KEAP1 levels in liver, fat and muscle.

TABLE 16

KEAP1 RNA levels in organs of DIO mice after ASO treatment

| Diet and Treatment | | % inhibition | | | |
|---|---|---|---|---|---|
| | | Liver | fat | muscle | pancreas |
| PBS normal chow | | 4 | 10 | 0 | 1 |
| HFD D12492 | PBS | 0 | 0 | 0 | 0 |
| | 549144 | 2 | 9 | 31 | 0 |
| | 645938 | 93 | 74 | 78 | 0 |

Liver triglyceride (TG) levels (mg/g of liver) were also assayed by biochemical quantitation and are presented in the table below. Liver TG levels are significantly reduced in DIO mice treated with ISIS 645938 indicating that a KEAP1 ASO may be effective in reducing or preventing hepatic steatosis, the initial pathological event in the development of NAFLD.

TABLE 17

Liver TG levels (mg/g of liver) of DIO mice after ASO treatment

| Diet and Treatment | | Liver TG |
|---|---|---|
| PBS normal chow | | 4.4 |
| HFD D12492 | PBS | 95.5 |
| | 549144 | 82.5 |
| | 645938 | 14.2 |

To determine whether KEAP1 inhibition would improve metabolic syndrome in DIO mice, a KEAP1 ASO was administered to the mice. Treatment of mice with the KEAP1 ASO significantly reduced KEAP1 with concordant improvement in glucose tolerance and insulin signaling, as well as reductions in hepatic triglyceride accumulation indicating that a KEAP1 ASO may be beneficial in treating metabolic syndrome in an animal.

Example 4: ASO Inhibition of KEAP1 in Male Gubra Mice

Lep$^{ob}$/Lep$^{ob}$ mice fed a high fat/fructose/cholesterol diet is known herein as the "Gubra" mouse model (Gubra ApS, Horshom, Denmark). The Gubra mouse is an accelerated diet-induced obese mouse model for fatty liver disease including fatty liver, NASH, and fibrosis. The Gubra mouse exhibits elements of liver steatosis, ballooning degeneration of hepatocytes, inflammation and fibrosis and affects metabolic parameters including body weight, hyperinsulinemia, fasting hyperleptinemia and impaired glucose tolerance.

To develop the diet induced Gubra phenotype, five-week old male mice were fed a high fat/fructose/cholesterol diet (40% HFD, 18% fructose, 2% cholesterol) for 19 weeks prior to the start of the study. After 16-17 weeks on the diet, the mice were pre-screened and randomized into treatment groups after liver biopsy and histological assessment (e.g., scoring of fibrosis after staining with Sirius Red and steatosis after staining with H&E).

Treatment

ISIS 645938 was administered to Gubra mice to test its effects on the mice. After 19-weeks on the high fat/fructose/cholesterol diet, a group of ten mice were treated with subcutaneous weekly injections of 40 mg/kg ISIS 645938, 50 mg/kg 549144 or PBS control over the course of eight weeks.

At the end of the study (8-weeks), the mice were sacrificed and livers were removed at the time of sacrifice. Liver RNA was extracted, as well as liver TG and TC, and analyses of hepatic pathology including steatosis, fibrosis stage and NAFLD Activity Score (NAS) were assessed and compared to pre-study biopsies at baseline. RNA was extracted from liver for real-time PCR analysis of liver KEAP1 RNA levels.

Levels of KEAP1 in Gubra mouse liver were determined using real-time PCR and the RTS4398_MGB primer probe set to measure RNA levels. RNA levels were normalized to RIBOGREEN® RNA quantification reagent (Molecular Probes, Inc. Eugene, Oreg.) and the results are presented as percent inhibition with respect to PBS-treated mice in the table below.

TABLE 18

ASO inhibition of KEAP1 in Gubra mouse liver

| ISIS No | % inhibition |
|---|---|
| PBS | 0 |
| 549144 | 3 |
| 645938 | 78 |

Body and Organ Weights

Body weights of the Gubra mice were measured every two days, and liver, left and right kidneys, and spleen weights were measured at week 8, at the end of the study. Also at the end of the study, EchoMRI scanning and terminal necropsy were performed, organs (liver, kidney, spleen, epididymal adipose tissue and quadriceps muscle) were harvested and liver, kidney and spleen weights were measured. Averages for each treatment group were calculated. Several weight points were chosen for presentation in the table below, along with weights of the organs relative to total body weight at the end of the study, and these data are presented (in grams) in the tables below.

TABLE 19

Weights (g) of body and organs of Gubra mice after antisense oligonucleotide treatment

| Treatment (ISIS NO) | Body | | | | | Relative weight | | | |
|---|---|---|---|---|---|---|---|---|---|
| | day 0 | day 16 | day 28 | day 44 | day 54 | Liver | L. Kidney | R. Kidney | Spleen |
| PBS | 59 | 59 | 59 | 59 | 61 | 9.0 | 0.29 | 0.30 | 0.20 |
| 549144 | 59 | 60 | 60 | 61 | 63 | 10.8 | 0.28 | 0.29 | 0.21 |
| 645938 | 58 | 55 | 52 | 49 | 48 | 11.0 | 0.38 | 0.38 | 0.34 |

Over the course of the study, a significant reduction in body weight was observed as mice treated with ISIS 645938 were approximately 83% of their weight before treatment. As compared to control mice, the mice treated with ISIS 645938 exhibited slight increases in relative liver, kidney and spleen weights (expressed as a percentage of body weight) as compared to PBS and ISIS 549144 control.

Plasma Chemistry Markers

To evaluate the effect of ASOs on hepatic function, plasma concentrations of liver transaminases ALT and AST, as well as plasma lipids (TG and TC) were measured in Gubra mice at baseline and at the end of the 8-week study. The averages for each treatment group are presented in the table below. "BL"=baseline.

TABLE 20

Plasma chemistry markers in ASO treated Gubra mice

| ISIS NO | ALT (U/L) | | AST (U/L) | | TC (mmol/L) | | TG (mmol/L) | |
|---|---|---|---|---|---|---|---|---|
| | BL | 8 wk | BL | 8 wk | BL | 8 wk | BL | 8 wk |
| PBS | 586 | 549 | 398 | 425 | 10 | 10 | 0.7 | 0.7 |
| 549144 | 702 | 636 | 445 | 462 | 11 | 11 | 0.7 | 0.6 |
| 645938 | 503 | 178 | 339 | 282 | 10 | 9 | 0.6 | 0.8 |

Overall, it was observed that the mice treated with ISIS 645938 exhibited an over 300 U/L reduction in plasma ALT as compared to baseline, a 57 U/L decrease in plasma AST as compared to baseline, a 1 mmol/L decrease in plasma TC as compared to baseline, and a 0.2 mmol/L increase in plasma TG over baseline. The data indicate that the KEAP1 ASO is decreasing liver damage as measured by ALT/AST.

An Oral Glucose Tolerance Test (OGTT) was performed. At week four of the eight week study, 4-hour fasted mice were subcutaneously injected with ISIS 645938 at time=0 minus one hour, and blood glucose was measured. One hour later, at time 0, glucose (2 g/kg) was ingested by the mice and blood glucose was tested again; thereafter, blood glucose was tested at 15 min, 30 min, 60 min and 120 min time points. Blood glucose area under the curve (AUC) was also calculated mmol/L×minute.

TABLE 21

OGTT: Blood glucose levels (mmol/L) in ASO treated Gubra mice

| Treatment | Time post glucose challenge (minutes) | | | | | AUC |
|---|---|---|---|---|---|---|
| (ISIS NO) | 0 | 15 | 30 | 60 | 120 | mmol/L |
| PBS | 8.5 | 15.2 | 15.8 | 10.3 | 7.6 | 1839 |
| 549144 | 7.9 | 13.4 | 13.5 | 8.9 | 7.2 | 1639 |
| 645938 | 7.2 | 15.2 | 14.2 | 7.5 | 6.9 | 1563 |

Liver TG and liver TC content (mg/g of liver) were also assayed by biochemical analysis, and are presented in the table below. Liver TG and TC levels are significantly reduced in Gubra mice treated with ISIS 645938 indicating that a KEAP1 ASO may be effective in reducing or preventing hepatic steatosis, the initial pathological event in the development of NAFLD.

TABLE 22

Liver TG and TC content (mg/g of liver) in Gubra mice after ASO treatment

| Treatment | Liver TG | Liver TC |
|---|---|---|
| PBS | 695 | 105 |
| 549144 | 739 | 103 |
| 645938 | 379 | 34 |

Histological assessment of NAFLD (steatosis, inflammation, damage/necrosis, and fibrosis), the current preclinical and clinical standard for assessment of NAFLD disease, was performed on sections both pre- and post-treatment using haematoxylin and eosin stain (H&E) stain, and fibrosis was assessed using Sirius Red stain. For liver steatosis, ISIS 645938 reduced steatosis by −37%, compared to no change with PBS treatment, which was in agreement with the biochemical analysis of liver triglyceride. ISIS 645938 treatment reduced ballooning degeneration by 100% versus no change with PBS treatment. Fibrosis was reduced by −16% with ISIS 645938 treatment versus a 73% increase with PBS treatment. Inflammation was increased to a similar extent across all treatment groups. Finally, the ISIS 645938 treatment reduced NAS (the sum of the scores for steatosis (0-3), hepatocellular ballooning (0-2) and lobular inflammation (0-3) by −21% versus a 5% increase with PBS treatment. Taken together, this indicates that a KEAP ASO treatment reduced and reversed NAFLD progression by decreasing steatosis, fibrosis, and degeneration.

TABLE 22

Liver histological assessment after KEAP1 ASO treatment

| | Saline | | ISIS 549144 | | ISIS 645938 | |
|---|---|---|---|---|---|---|
| | Pre-treatment | Post-treatment | Pre-treatment | Post-treatment | Pre-treatment | Post-treatment |
| Steatosis | 3 ± 0 | 3 ± 0 | 3 ± 0 | 3 ± 0 | 3 ± 0 | 1.9 ± 0.1 |
| Ballooning Degeneration | 0.88 ± 0.13 | 0.88 ± 0.13 | 0.78 ± 0.15 | 0.89 ± 0.11 | 0.43 ± 0.2 | 0 ± 0 |
| Fibrosis | 1.5 ± 0.2 | 2.6 ± 0.2 | 1.8 ± 0.2 | 2.4 ± 0.2 | 1.9 ± 0.3 | 1.6 ± 0.2 |
| Inflammation | 1.6 ± 0.2 | 1.9 ± 0.13 | 1.7 ± 0.2 | 2.1 ± 0.1 | 1.4 ± 0.2 | 2.0 ± 0.3 |
| NAS | 5.5 ± 0.2 | 5.8 ± 0.2 | 5.4 ± 0.2 | 6.0 ± 0.2 | 4.9 ± 0.3 | 3.9 ± 0.3 |

Liver fibrosis markers hydroxyproline and collagen were assessed in the mice. Liver collagen mRNA levels were quantified using a Colla2 assay (ThermoFisher Scientific assay ID #Mm00483888_m1). Liver hydroxyproline and collagen were reduced as shown in the table below indicating a reduction in liver fibrosis after treatment with KEAP1 ASO.

TABLE 23

Liver fibrosis markers in Gubra mice after ASO treatment

| Treatment | Hepatic hydroxyproline (µg/mg liver) | Hepatic Colla2 mRNA expression (% saline) |
|---|---|---|
| PBS | 0.53 | 100 |
| 549144 | 0.50 | 101 |
| 645938 | 0.28 | 40 |

Overall, data from this Gubra mouse study indicated that an ASO targeting KEAP1 was active in liver, was well tolerated, decreased several biomarkers of metabolic and liver diseases, and KEAP1 is an important candidate for the treatment of obesity, type 2 diabetes and/or insulin sensitivity, hyperlipidemia, NASH, NAFLD and oxidative stress related diseases, disorders or conditions.

Example 5: ASO Inhibition of KEAP1 in Male Ob/Ob Mice

ASOs described in the studies above will be evaluated for their ability to reduce murine KEAP1 RNA transcript in an 8-week ob/ob mice study.

Treatment

C57BL/6J-Lepr ob ("ob/ob") mice will be divided into treatment groups consisting of eight animals. Mice will be injected subcutaneously once a week for 8 weeks with either 25 or 10 mg/kg of ISIS 549144 control oligonucleotide, 25 or 10 mg/kg of ISIS 645938 or ISIS 645958, and one group of seven ob/ob mice will be injected with PBS as a control to which the antisense oligonucleotide treated groups are compared. Several clinical endpoints will be measured over the course of the study. The body and food weights will be measured weekly, and tail bleeds will be performed at baseline and weekly thereafter, as well as at the time of sacrifice. The mice will be euthanized 72 hours after the last dose and after 8 weeks of ASO treatment organs and plasma will be harvested for further analysis.

RNA Analysis

At the end of the treatment period, RNA will be extracted from liver, kidney, white adipose tissue (WAT) and pancreas for quantitative real-time PCR analysis of RNA expression of KEAP1. Murine KEAP1 primer probe set RTS4398_MGB will be used to measure RNA levels. Results will be presented as percent inhibition of KEAP1, relative to PBS control, normalized against Cyclophilin A. Both ISIS 645938 and ISIS 645958 will be shown as active inhibitors in multiple tissues with ISIS 645938 the more potent inhibitor.

Plasma Chemistry Markers

To evaluate the effect of treatment with ISIS oligonucleotides on plasma levels of various biomarkers of liver and kidney function, plasma levels of liver transaminases (ALT and AST), total cholesterol (CHOL), creatinine (CRE), glucose (GLU), HDL, LDL, triglycerides (TRIG), BUN, non-esterified fatty acids (NEFA), 3HB will be measured using an automated clinical chemistry analyzer (Hitachi Olympus AU400e, Melville, N.Y.).

Overall, the plasma chemistry results will indicate that both ISIS 645938 and ISIS 645958 are tolerable in ob/ob mice.

Protein Analysis

The cytoprotective gene NQO1 is a downstream target gene of Nrf2 in the KEAP1 pathway. NQO1 protein levels in ob/ob mouse liver and kidney will be quantified using a commercially available ELISA kit according to the manufacturer described protocol. The results will indicate that treatment with ASOs targeting KEAP increase NQO1 expression levels. The result will suggest that ASO inhibition of KEAP1 decreases KEAP-mediated repression of Nrf2 activity and allows expression of Nrf2 downstream genes such as NQO1.

Kidney Injury Molecule-1 (Kim-1) and Neutrophil Gelatinase-Associated Lipocalin (NGAL) are biomarkers found in urine or plasma and are used to detect renal tubule injury. Kim-1 and NGAL protein levels in kidneys of ob/ob mice treated with ASOs will be quantified using a commercially available ELISA kit according to the manufacturer described protocol. The results will show a lack of significant increase in the biomarkers Kim-1 and NGAL and indicate that KEAP1 ASO treatment does not injure the kidney.

Body and Organ Weights

Body weights will be measured weekly, and kidney, liver, spleen and white adipose tissue (WAT) weights will be measured at the end of the study. Results showing a lack of significant increases in the body or organ weights in KEAP1 ASO treated mice will indicate that ASO treatment is tolerable for the mice.

Hepatic Triglycerides

Hepatic triglyceride (TG) concentrations (□g/g of liver) will be assayed by ELISA. Liver TG levels will be significantly reduced in KEAP1 ASO treated ob/ob mice indicating that KEAP1 ASOs may be effective in reducing or preventing fatty liver diseases such as hepatic steatosis, NASH and/or NAFLD.

Glucose Tolerance Test (GTT)

At week four of the eight week study, a glucose tolerance test (GTT) will be performed. 24 hours after treatment with the fourth dose of ASO or PBS. 4-hour-fasted ob/ob mice will be intraperitonally administered 2 grams of glucose per kg body weight, and blood will be drawn at various timepoints using a One Touch II™ glucose monitor. KEAP1 ASO treated mice will be able to clear glucose at a higher rate than control treated mice, indicating an improvement in glucose tolerance with KEAP1 ASO treatment.

Example 6: ASO Inhibition of KEAP1 in a House Dust Mite (HDM)-Induced Allergic Asthma Model The House Dust Mite (HDM)-induced mouse model of severe asthma features many similarities to human allergic asthma, including the presence of eosinophilic lung inflammation and the release of inflammatory mediators and cytokines primarily associated with Th2-type inflammation.

As noted in the description above, the KEAP1/Nrf2 system is a major regulator of the intracellular antioxidant response to cellular oxidative and electrophile stress. Oxidative stress occurs when the generation of reactive oxygen species (ROS) and reactive nitrogen species (RNS) exceeds the activity of intracellular antioxidant defense mechanisms. This imbalance causes an accumulation of ROS that leads to greater lipid peroxidation, damage to proteins, cell membranes and DNA and exacerbates the severity of several diseases. For example, oxidative stress plays an important role in various disease pathologies including diabetes, diabetic nephropathy, diabetic cardiomyopathy, insulin resistance, fibrosis (e.g. hepatic fibrosis or pulmonary fibrosis), NAFLD/NASH, cancer, chronic obstructive pulmonary disease (COPD), asthma, age related macular degeneration, atherosclerosis, and neurologic disorders.

In the basal condition, KEAP1 tethers Nrf2 and causes Nrf2 ubiquitination and degradation. Upon cellular stress assault, KEAP1 protein dissociates with Nrf2, allowing Nrf2 to translocate into the nucleus where it acts as a transcriptional activator to induce antioxidant genes including GSTs, GCLM, NQO1, NQO2, HO-1. Current evidence suggests that Nrf2 protein is downregulated in COPD, and activation of Nrf2 prevents COPD in cigarette smoke-exposed mice.

The pathology of chronic asthma shows prominent structural changes in the airway wall—specifically alteration in the extracellular matrix (ECM) and thickening of the airway smooth muscle (ASM). While not to be bound by theory, Nrf2 is currently believed to be an important determinant of smooth muscle function (An, S. S., et al., 2016, *J. Allergy Clin. Immunol*. pii: S0091-6749(16)00116-0. [Epub ahead of print]). In chronic asthma, the aforementioned structural changes may be attributable to defective Nrf2-directed regulation of oxidative stress, leading to abnormal ECM remodeling and increased contractility of the ASM cell, resulting in asthmatic airflow obstruction.

As noted in examples set forth in the present disclosure, it was observed that inhibition of KEAP1 results in increased transcription of antioxidant and detoxifying genes.

Treatment 8- to 10-week old female C57B16 mice, weighing approximately 20 g, were fed a normal chow diet and divided into treatment groups consisting of twelve animals. 10 mg/kg of ISIS 645938 was locally administered to the mouse lung by intratracheal administration twice a week starting two weeks before the first challenge with house dust mite (HDM) allergen at time 0. ISIS 549148 (a 3-10-3 cEt gapmer having the sequence GGCTACTACGCCGTCA, incorporated herein as SEQ ID NO: 11) was used as an ASO control, and saline alone served as a vehicle control to which the ASO-treated groups were compared. At time 0, the mice undergoing treatment with ASOs and the saline control group were then challenged with HDM allergen on days 0, 7, 14. Another group of "naïve" mice was not challenged with ASO or HDM allergen. At the end of study, lung function airway hyperresponsiveness (AHR) was measured for the various groups of mice. After lung function measurements, the mice were then sacrificed and lung tissue was harvested for further analysis.

Several endpoints were measured to examine the effects of targeting KEAP1. Target mRNA knockdown of KEAP1 was measured in addition to the effect on various mucus markers (mRNA). Differential cell counts of inflammatory cells in the lung were performed on the bronchoalveolar lavage (BAL) fluid to evaluate the effects of the ASOs targeting murine KEAP1 on cell recruitment to the airways. Lungs were then inflated and stained for mucus (PAS-stained).

RNA Analysis

At the end of the treatment period, RNA was extracted from lung tissue for quantitative real-time PCR analysis of RNA expression for KEAP1. Murine KEAP1 primer probe set RTS4398_MGB (forward sequence AAGGTCATGGAAAGGCTTATTGAGT, designated herein as SEQ ID NO: 12; reverse sequence GTTCATCACGTGCAGGACACA, designated herein as SEQ ID NO: 13; probe sequence TCTCCGTGGGCGAGAA, designated herein as SEQ ID NO: 14) was used to measure RNA levels. Results are presented in the table below as percent inhibition of KEAP1, relative to PBS control, normalized against RIBOGREEN®. Treatment with the KEAP1 ASOs resulted in a significant reduction of KEAP1 mRNA in the lung in comparison to the control groups.

TABLE 24

ASO inhibition of KEAP1 RNA in organs of HDM mice

| Treatment (ISIS NO) | | % inhibition |
|---|---|---|
| Naïve (no HDM) | | 0 |
| HDM-induced | Saline | 0 |
| | 645938 | 63 |
| | 549148 | 13 |

Mucus Marker RNA analysis

Murine markers of inflammation and mucus overproduction commonly increased during asthma were assessed including:

(1) inflammation marker macrophage-restricted F4/80 using primer probe set: F4/80, mEmr1_LTS00125 (Forward: GGCCATTGCCCAGATTTTC, designated herein as SEQ ID NO: 21; reverse: CGGTTGAGCAGACAGTGAATGA, designated herein as SEQ ID NO: 22; probe: CCAGATTGGCCCCTTGGCAAGCX, designated herein as SEQ ID NO: 23) to measure mRNA levels, (2) mucus marker GOB5 (a member of the calcium-activated chloride channel family, a.k.a. chloride channel accessory 1, or CLCA1) primer probe set: Gob5, RTS1845 (Forward: CACTAAGGTGGCCTACCTCCAA, designated herein as SEQ ID NO: 24; reverse AGCTCGCTTGAATGCTGTATTTC, designated herein as SEQ ID NO: 25; probe: CCCAGGCACGGCTAAGGTTGGCX, designated herein as SEQ ID NO: 26) to measure mRNA levels, (3) mucus marker SPDEF (SAM-pointed domain—containing ETS transcription factor) (primer probe set: SPDEF, RTS4444 (Forward: GCGAGGTCCTGAAAGATATTGAG, designated herein as SEQ ID NO: 27; reverse: GCCACTTCTGCACGTTACCA, designated herein as SEQ ID NO: 29; probe: CTTCTGAACATCACAGCAGACCCTGGG, designated herein as SEQ ID NO: 29) to measure mRNA levels, and (4) mucus marker mucin 5 subtype B (MUC5B) (primer probe set: mMUC5B, RTS3745 (Forward: TGACTCCATATCCTCATCCACAAG, designated herein as SEQ ID NO: 30; reverse AGGTGTAAGGCGCTCATGCT, designated herein as SEQ ID NO: 31; probe: CACCTTCATCCCACCTATCACTGTCTTCCCX, designated herein as SEQ ID NO: 32) to measure mRNA levels.

The results are presented in the table below as % saline. The results indicate that treatment with ISIS 645938 resulted in decreased expression levels of the biomarkers of inflammation and mucus production.

TABLE 25

Expression of markers of inflammation in HDM-induced mice treated with ASOs

| | | % saline | | | |
|---|---|---|---|---|---|
| Treatment (ISIS NO) | | Macrophage (F4/80) | GOB5 | SPDEF | MUC5B |
| Naïve (no HDM) | | 41 | 8 | 79 | 77 |
| HDM-induced | Saline | 100 | 100 | 100 | 100 |
| | 645938 | 34 | 29 | 34 | 41 |
| | 549148 | 84 | 91 | 147 | 92 |

Bronchoalveolar Lavage (BAL)

Differential cell counts of inflammatory cells in the lung were performed on the bronchoalveolar lavage (BAL) fluid to evaluate the effects of the ASOs targeting murine KEAP1. HDM greatly increases the number of eosinophils recruited to the airways. HDM-induced control mice treated with saline or ISIS 549148 showed an induction in eosinophils, whereas HDM-induced mice treated with ISIS 645938 targeting KEAP1 exhibited a shift in the percentage of BAL cells to more macrophages and fewer eosinophils.

TABLE 26

ASO inhibition of KEAP1 Reduces
Eosinophils in HDM treated mice

| Treatment (ISIS NO) | | % BAL Eosinophils |
|---|---|---|
| Naïve (no HDM) | | 0 |
| HDM-induced | PBS | 100 |
| | 645938 | 35 |
| | 549148 | 78 |

Airway Hyperresponsiveness (AHR)

To evaluate the effect of ASOs on airway hyperresponsiveness (AHR), 24 hours after the last HDM allergen challenge, anesthetized but awake mice were exposed to aerosolized PBS using an ultrasonic nebulizer to set a baseline value, and then increasing doses (0, 3, 6, 12 and 25 mg/ml) of aerosolized □-methacholine (Mch), a non-specific cholinergic agonist, were administered to induce bronchospasm and airway obstruction. PenH (enhanced pause) values were measured for 2 minutes after each Mch aerosol dose, using a whole body plethysmograph (Buxco, Electronics, Troy, N.Y., USA). The average PenH values were expressed for the 25 mg/ml Mch concentration as the percentage of PBS control PenH value. KEAP1 ASO treatment moderately, but significantly reduced AHR as compared to PBS- or ASO-control treatment groups.

TABLE 27

ASO inhibition of KEAP1 Effects Lung Function (25 mg/ml Mch)

| Treatment (ISIS NO) | | Penh % PBS Cont |
|---|---|---|
| Naïve (no HDM) | | 47 |
| HDM-induced | PBS | 100 |
| | 645938 | 72 |
| | 549148 | 87 |

Overall, KEAP1 ASO resulted in reduced target RNA in HDM-induced mouse lung tissue, reduced airway eosinophilia, reduced mucus markers, and had a slight effect on AHR, whereas the control ASO- and PBS-treated HDM-induced mice did not show these improvements.

Example 7: ASO Inhibition of KEAP1 in Male Ob/Ob Mice

ASOs described in the studies above were evaluated for their ability to reduce murine KEAP1 RNA transcript in a 10-week ob/ob mice study.

Treatment

C57BL/6J-Lepr ob ("ob/ob") mice were divided into treatment groups consisting of eight animals. Mice were injected subcutaneously once a week for 10 weeks with 25 mg/kg of ISIS 549144 control oligonucleotide, or with 25 mg/kg or 10 mg/kg of ISIS 645938, and one group of eight ob/ob mice were injected with PBS as a control to which the antisense oligonucleotide treated groups are compared. Several clinical endpoints were measured over the course of the study. The body and food weights were measured weekly, and tail bleeds were performed at baseline and weekly thereafter, as well as at the time of sacrifice. The mice were euthanized 72 hours after the last dose and organs and plasma were harvested for further analysis.

KEAP1 RNA Analysis

At the end of the treatment period, RNA was extracted from liver, kidney, heart, white adipose tissue (WAT), lung, pancreas, and spleen for quantitative real-time PCR analysis of mRNA expression of KEAP1. Murine KEAP1 primer probe set RTS4398_MGB was used to measure mRNA levels. Results are presented as percent of KEAP1, relative to PBS control, normalized against Cyclophilin A. ISIS 645938 was shown as an active inhibitor in multiple tissues.

TABLE 28

Expression of KEAP1 in ob/ob mice treated with KEAP1 ASO

| | Dose | KEAP1 mRNA (% saline) | | | | | | |
|---|---|---|---|---|---|---|---|---|
| Treatment | (mg/kg) | Liver | Kidney | Heart | WAT | Lung | Pancreas | Spleen |
| PBS | — | 100 | 100 | 100 | 100 | 100 | 100 | 100 |
| 549144 | 25 | 88 | 93 | 86 | 110 | 106 | 99 | 109 |
| 645938 | 10 | 26 | 41 | 79 | 65 | 113 | 102 | 84 |
| 645938 | 25 | 14 | 27 | 59 | 47 | 66 | 95 | 81 |

NQO1 RNA analysis

At the end of the treatment period, RNA was extracted from heart, liver, kidney, white adipose tissue (WAT), lung, spleen, and pancreas for quantitative real-time PCR analysis of mRNA expression of NQO1. Murine NQO1 primer probe set mNQO1_LTS00751 was used to measure mRNA levels. Results are presented as percent of NQO1, relative to PBS control, normalized against Cyclophilin A. ISIS 645938 was shown to upregulate NQO1 expression in multiple tissues. The result shows that ASO inhibition of KEAP1 decreases KEAP-mediated repression of Nrf2 activity and allows expression of Nrf2 downstream genes such as NQO1.

TABLE 29

Expression of NQO1 in ob/ob mice treated with KEAP1 ASO

| | Dose | NQO1 mRNA (% saline) | | | | | | |
|---|---|---|---|---|---|---|---|---|
| Treatment | (mg/kg) | Liver | Kidney | Heart | WAT | Lung | Pancreas | Spleen |
| PBS | — | 100 | 100 | 100 | 100 | 100 | 100 | 100 |
| 549144 | 25 | 88 | 92 | 99 | 113 | 78 | 82 | 114 |

TABLE 29-continued

Expression of NQO1 in ob/ob mice treated with KEAP1 ASO

| Treatment | Dose (mg/kg) | Liver | Kidney | Heart | WAT | Lung | Pancreas | Spleen |
|---|---|---|---|---|---|---|---|---|
| 645938 | 10 | 304 | 332 | 100 | 220 | 198 | 194 | 99 |
| 645938 | 25 | 412 | 349 | 110 | 309 | 304 | 401 | 105 |

GSTA1 RNA Analysis

At the end of the treatment period, RNA was extracted from heart, liver, kidney, white adipose tissue (WAT), lung, spleen, and pancreas for quantitative real-time PCR analysis of mRNA expression of GSTA1. Murine GSTA1 primer probe set mGstal_LTS34766 was used to measure mRNA levels. Results are presented as percent of GSTA1, relative to PBS control, normalized against Cyclophilin A. ISIS 645938 was shown to upregulate GSTA1 expression.

TABLE 30

Expression of GSTA1 in ob/ob mice treated with KEAP1 ASO

| Treatment | Dose (mg/kg) | Liver | Kidney | Heart | WAT | Lung | Pancreas | Spleen |
|---|---|---|---|---|---|---|---|---|
| PBS | — | 100 | 100 | 100 | 100 | 100 | 100 | 100 |
| 549144 | 25 | 72 | 83 | 99 | 92 | 38 | 104 | 35 |
| 645938 | 10 | 250 | 928 | 253 | 141 | 65 | 354 | 110 |
| 645938 | 25 | 336 | 1054 | 219 | 226 | 117 | 87 | 108 |

Plasma Chemistry Markers

To evaluate the effect of treatment with ISIS oligonucleotides on plasma levels of various biomarkers of liver and kidney function, plasma levels of liver transaminases (ALT and AST), total cholesterol (CHOL), creatinine (CRE), HDL, LDL, triglycerides (TRIG), BUN, non-esterified fatty acids (NEFA), 3HB were measured using an automated clinical chemistry analyzer (Hitachi Olympus AU400e, Melville, N.Y.).

Overall, the plasma chemistry results indicate that ISIS 645938 is tolerable in ob/ob mice.

Kidney Biomarker Analysis

Kidney Injury Molecule-1 (KIM-1) and Neutrophil Gelatinase-Associated Lipocalin (NGAL) are biomarkers used to detect renal tubule injury. At the end of the treatment period, RNA was extracted from kidney for quantitative real-time PCR analysis of mRNA expression of KIM-1 and NGAL. Murine KIM-1 primer probe set RTS1475 (Forward Sequence: TGGTTGCCTTCCGTGTCTCT, designated herein as SEQ ID NO: 33; Reverse Sequence: TCAGCTCGGGAATGCACAA, designated herein as SEQ ID NO: 34; Probe Sequence: AGATTGAAGCTTTGCAGAACGCAGCGX, designated herein as SEQ ID NO: 35, wherein X is a label) was used to measure KIM-1 mRNA levels. Murine NGAL (LCN2) primer probe set mLcn2_LTS00362 (Forward Sequence: GGCCTCAAGGACGACAACA, designated herein as SEQ ID NO: 36; Reverse Sequence: ACCACCCATTCAGTTGTCAATG, designated herein as SEQ ID NO: 37; Probe Sequence: CATCTTCTCTGTCCCCACCGACCAAX, designated herein as SEQ ID NO: 38, wherein X is a label) was used to measure NGAL mRNA levels. Results are presented as percent of KIM-1 or NGAL, relative to PBS control, normalized against Cyclophilin A.

The results show a lack of significant increase in the biomarkers KIM-1 and NGAL and indicate that KEAP1 ASO was well tolerated in the kidney.

TABLE 31

Plasma markers of ob/ob mice treated with ASOs

| Treatment | Dose (mg/kg) | ALT (U/L) | AST (U/L) | CHOL (mmol/L) | CRE (mg/dL) | HDL (mg/dL) | LDL (mg/dL) | TRIG (mmol/L) | BUN (mg/dL) | NEFA (mEq/L) | 3HB (mmol/L) |
|---|---|---|---|---|---|---|---|---|---|---|---|
| PBS | — | 487.8 | 440.8 | 230.8 | 0.24 | 191.5 | 60.1 | 80.0 | 24.1 | 0.81 | 364.2 |
| 549144 | 25 | 342.4 | 309.5 | 224.5 | 0.21 | 190.6 | 48.8 | 71.4 | 23.6 | 0.85 | 292.0 |
| 645938 | 10 | 515.8 | 562.3 | 269.6 | 0.20 | 205.9 | 67.4 | 89.8 | 20.5 | 0.96 | 178.7 |
| 645938 | 25 | 451.5 | 632.0 | 269.1 | 0.18 | 200.7 | 63.3 | 101.3 | 19.5 | 0.95 | 153.6 |

TABLE 32

Kidney biomarkers in ob/ob mice treated with KEAP1 ASO

| Treatment | Dose (mg/kg) | KIM-1 (% saline) | NGAL (% saline) |
|---|---|---|---|
| 549144 | 25 | 105 | 83 |
| 645938 | 10 | 162 | 110 |
| 645938 | 25 | 233 | 118 |

Body and Organ Weights

Body weights were measured weekly. Kidney, liver, spleen and white adipose tissue (WAT) weights were measured at the end of the study and are presented as percent body weight (% BW) in the table below. Results showing a lack of significant increases in the body or organ weights in KEAP1 ASO treated mice indicate that ASO treatment is tolerable for the mice.

TABLE 33

Body weight of ob/ob mice treated with KEAP1 ASO

| Treatment | Dose (mg/kg) | Body Weight (g) |
|---|---|---|
| PBS | — | 59.3 |
| 549144 | 25 | 60 |
| 645938 | 10 | 52.8 |
| 645938 | 25 | 50.9 |

TABLE 34

Organ weights of ob/ob mice treated with KEAP1 ASO

| Treatment | Dose (mg/kg) | Liver (% BW) | Kidney (% BW) | Spleen (% BW) | WAT (% BW) |
|---|---|---|---|---|---|
| PBS | — | 7.29 | 0.70 | 0.23 | 5.60 |
| 549144 | 25 | 7.75 | 0.73 | 0.26 | 5.23 |
| 645938 | 10 | 9.51 | 0.82 | 0.19 | 4.55 |
| 645938 | 25 | 11.13 | 0.96 | 0.19 | 4.93 |

Glucose Tolerance Test (GTT)

An oral glucose tolerance test (OGTT) was performed at weeks 4 and 9 in the ob/ob mice. The mice were fasted for sixteen hours and were administered 1 gram of glucose per kg body weight, and blood was drawn at various timepoints using a One Touch II™ glucose monitor. At week 9, KEAP1 ASO treated mice were able to clear glucose at a higher rate than control treated mice, indicating an improvement in glucose tolerance with KEAP1 ASO treatment.

TABLE 35

Week 4 OGTT: Blood glucose levels (mg/dL) in ob/ob mice treated with KEAP1 ASO

| Treatment | Dose (mg/kg) | 0 min | 30 min | 60 min | 90 min | 120 min |
|---|---|---|---|---|---|---|
| PBS | — | 135 | 453 | 265 | 232 | 233 |
| 549144 | 25 | 137 | 391 | 236 | 231 | 227 |
| 645938 | 10 | 183 | 357 | 282 | 236 | 234 |
| 645938 | 25 | 171 | 408 | 244 | 221 | 211 |

TABLE 36

Week 9 OGTT: Blood glucose levels (mg/dL) in ob/ob mice treated with KEAP1 ASO

| Treatment | Dose (mg/kg) | 0 min | 15 min | 30 min | 60 min | 90 min | 120 min |
|---|---|---|---|---|---|---|---|
| PBS | — | 138 | 451 | 400 | 242 | 222 | 194 |
| 549144 | 25 | 153 | 402 | 337 | 218 | 174 | 177 |
| 645938 | 10 | 130 | 387 | 287 | 198 | 181 | 156 |
| 645938 | 25 | 122 | 368 | 269 | 181 | 186 | 152 |

Glucose and Insulin

After being fasted for 5-hours, a tail bleed was performed on the mice to measure glucose and insulin levels at weeks 5 and 8. KEAP1 ASO decreased both insulin and glucose as shown in the table below with the data suggesting an improvement in insulin sensitivity.

TABLE 37

Plasma levels of insulin (ng/mL) and glucose (mg/dL) in ob/ob mice treated with KEAP1 ASO

| Treatment | Dose (mg/kg) | Insulin Week 5 | Insulin Week 8 | Glucose Week 5 | Glucose Week 8 |
|---|---|---|---|---|---|
| PBS | — | 20.05 | 26.56 | 301 | 308 |
| 549144 | 25 | 33.46 | 26.01 | 236 | 240 |
| 645938 | 10 | 18.19 | 20.16 | 299 | 321 |
| 645938 | 25 | 21.65 | 12.41 | 201 | 211 |

Example 8: KEAP1 ASO Comparison with Bardoxolone Methyl in Wildtype Mice

Bardoxolone methyl (RTA 402) is a small molecule inhibitor of the NF-κB pathway and an activator of the Nrf2 pathway. The drug was being tested in a Stage 3 clinical trial for kidney disease, however, the trial was ended early when a higher than expected incidence of cardiovascular adverse events was observed in the drug arm of the trial.

The effect of KEAP1 ASO treatment was compared to the effect of bardoxolone methyl treatment in a 6-week head-to-head study in C57 wildtype mice fed a normal chow diet (D12451 Research Diets, New Brunswick, N.J.).

Treatment

C57BL/6 wildtype mice were divided into treatment groups consisting of four animals. Antisense oligonucleotide treated groups were injected subcutaneously once a week for 6 weeks with either 25 or 40 mg/kg of ISIS 549144 control oligonucleotide, 25 or 40 mg/kg of ISIS 645938, 25 or 40 mg/kg of ISIS 645958, and one group of four mice was injected with PBS as a control to which the antisense oligonucleotide treated groups are compared. Bardoxolone methyl (RTA 402) treated groups were given 2.5 or 10 mg/kg by oral gavage 5 days per week for 6 weeks, and one group of four mice was given a vehicle control (Cremophor EL:DMSO:PBS (1:1:8) mixture) by oral gavage as a control to which the bardoxolone methyl treated groups are compared. The mice were euthanized 24 hours after the last dose; liver and heart were harvested for further analysis.

KEAP1 RNA Analysis

At the end of the treatment period, RNA was extracted from liver and heart for quantitative real-time PCR analysis of mRNA expression of KEAP1. Murine KEAP1 primer probe set RTS4398_MGB (forward sequence AAGGTCATGGAAAGGCTTATTGAGT, designated herein as SEQ ID NO: 12; reverse sequence GTTCATCACGTGCAGGACACA, designated herein as SEQ ID NO: 13; probe sequence TCTCCGTGGGCGAGAA, designated herein as SEQ ID NO: 14) was used to measure mRNA levels. Results are presented in the table below as percent of KEAP1 mRNA, relative to PBS or vehicle control, normalized against Cyclophilin A.

Treatment with KEAP1 ASO resulted in significant dose-dependent reductions of KEAP1 mRNA expression in the liver and heart compared to the ASO control (ISIS 54944) and PBS control as shown in the table below. Treatment with bardoxolone methyl resulted in an increase of KEAP1 mRNA expression in the liver and a decrease in the heart compared to the vehicle control as shown in the table below.

TABLE 38

Expression of KEAP1 in wildtype mice treated with KEAP1 ASO or bardoxolone methyl

| Treatment | Dose (mg/kg) | Liver | Heart |
|---|---|---|---|
| 549144 (% PBS) | 25 | 108.7 | 80.2 |
| 549144 (% PBS) | 40 | 95.5 | 68.9 |
| 645938 (% PBS) | 25 | 17.8 | 64.0 |
| 645938 (% PBS) | 40 | 8.9 | 53.2 |
| 645958 (% PBS) | 25 | 31.4 | 78.4 |
| 645958 (% PBS) | 40 | 21.3 | 63.6 |
| RTA 402 (% vehicle) | 2.5 | 156.9 | 97.9 |
| RTA 402 (% vehicle) | 10 | 135.6 | 91.5 |

NQO1 RNA Analysis

At the end of the treatment period, RNA was extracted from liver and heart for quantitative real-time PCR analysis of mRNA expression of NQO1. Murine NQO1 primer probe set mNQO1_LTS00751 (forward sequence CCTGGAAGGATGGAAGAAACG, designated herein as SEQ ID NO: 18; reverse sequence CAGGCTGCTTGGAGCAAAAT, designated herein as SEQ ID NO: 19; probe sequence AAACCGTCTGGGAGGAGACCCCACTX, designated herein as SEQ ID NO: 20, wherein X is a label) was used to measure mRNA levels. Results are presented in the table below as percent of NQO1, relative to PBS control, normalized against Cyclophilin A.

Treatment with both the KEAP1 ASO and bardoxolone methyl resulted in significant dose-dependent increases in NQO1 mRNA expression in the liver in comparison to the control ASO, the vehicle control or PBS.

Treatment with bardoxolone methyl, but not with the KEAP1 ASO, resulted in significant dose-dependent increases in NQO1 mRNA expression in the heart in comparison to the control ASO, the vehicle control or PBS.

TABLE 39

Expression of NQO1 in wildtype mice treated with KEAP1 ASO or bardoxolone methyl

| Treatment | Dose (mg/kg) | Liver | Heart |
|---|---|---|---|
| 549144 (% PBS) | 25 | 98.1 | 71.3 |
| 549144 (% PBS) | 40 | 66.7 | 62.9 |
| 645938 (% PBS) | 25 | 537.8 | 79.3 |
| 645938 (% PBS) | 40 | 912.2 | 83.6 |
| 645958 (% PBS) | 25 | 220 | 99.3 |
| 645958 (% PBS) | 40 | 442.63 | 76.1 |
| RTA 402 (% vehicle) | 2.5 | 830.9 | 200.4 |
| RTA 402 (% vehicle) | 10 | 1067.8 | 271.3 |

GSTA1 RNA Analysis

At the end of the treatment period, RNA was extracted from liver and heart for quantitative real-time PCR analysis of mRNA expression of GSTA1. Murine GSTA1 primer probe set mGstal_LTS34766 (forward sequence CCCCTTTCCCTCTGCTGAAG, designated herein as SEQ ID NO: 15; reverse sequence TGCAGCTTCACTGAATCTTGAAAG, designated herein as SEQ ID NO: 16; probe sequence TTCCTTGCTTCTTGAATTTGTTTTGCATCCAT, designated herein as SEQ ID NO: 17) was used to measure mRNA levels. Results are presented in the table below as percent of GSTA1, relative to PBS or vehicle control, normalized against Cyclophilin A.

Treatment with both the KEAP1 ASO and bardoxolone methyl resulted in significant dose-dependent increases in GSTA1 mRNA expression in the liver in comparison to the control ASO, the vehicle control or PBS.

Treatment with bardoxolone methyl, but not with the KEAP1 ASO, resulted in significant dose-dependent increases in GSTA1 mRNA expression in the heart in comparison to the control ASO, the vehicle control or PBS.

TABLE 40

Expression of GSTA1 in wildtype mice treated with KEAP1 ASO or bardoxolone methyl

| Treatment | Dose (mg/kg) | Liver | Heart |
|---|---|---|---|
| 549144 (% PBS) | 25 | 84 | 71.8 |
| 549144 (% PBS) | 40 | 49.3 | 63.1 |
| 645938 (% PBS) | 25 | 1560.8 | 71.8 |
| 645938 (% PBS) | 40 | 2883.9 | 78.1 |
| 645958 (% PBS) | 25 | 636.4 | 79.2 |
| 645958 (% PBS) | 40 | 1892.2 | 112.9 |
| RTA 402 (% vehicle) | 2.5 | 1087.1 | 483.6 |
| RTA 402 (% vehicle) | 10 | 1817.3 | 615.0 |

As the data show, KEAP1 ASO treatment impacts the heart less than bardoxolone methyl treatment. Thus, KEAP1 ASO treatment may not have adverse effects on the heart such as those seen after bardoxolone methyl treatment.

Example 9: ASO Inhibition of KEAP1 in a Bleomycin-Induced Lung Fibrosis Model

Pulmonary fibrosis is a component of many interstitial lung diseases, including idiopathic pulmonary fibrosis, a chronic, progressive disease for which there is currently no effective therapy. Bleomycin has been widely used in rodents to model pulmonary fibrosis for the study of mechanisms involved in fibrogenesis and for evaluation of potential therapies (Curr. Protoc. Pharmacol. 40:5.46.1-5.46.17. © 2008 by John Wiley & Sons, Inc.).

Treatment 8- to 10-week old male C57B16 mice, weighing approximately 20 g, were fed a normal chow diet and divided into treatment groups consisting of twenty animals. 10 mg/kg of ISIS 645938 was locally administered to the mouse lung by intratracheal administration twice a week starting two weeks before the first challenge with bleomycin. ISIS 549148 was used as an ASO control, and saline alone served as a vehicle control to which the ASO-treated groups were compared. At the end of two weeks, the mice undergoing treatment with ASOs and the saline control group received a single intratracheal administration of bleomycin at 5 U/kg in 50 µl of PBS. Another group of 16 "naïve" mice was not challenged with ASO or bleomycin. The groups are further defined in the table below.

TABLE 41

Groups of mice

| Group# | ASO | Bleomycin |
|---|---|---|
| 1 | No | No |
| 2 | No | Yes |
| 3 | 645938 (Keap1) | Yes |
| 4 | 549148 (control) | Yes |

Body weights and survival rates of the mice were regularly monitored. The assays are described below and demonstrate the tolerability of treatment of the mice with antisense oligonucleotides targeting KEAP1.

Body Weights

Body weights of the mice were regularly measured. Results are presented in the table below. Treatment with the KEAP1 ASOs did not result in any adverse change in weight in comparison to the naive control group.

TABLE 42

| | | Body weights | | | |
|---|---|---|---|---|---|
| Group# | ASO | Bleomycin | Day 7 | Day 17 | Day 30 |
| 1 | No | No | 27 | 29 | 29 |
| 2 | No | Yes | 26 | 25 | 22 |
| 3 | 645938 (Keap1) | Yes | 26 | 25 | 26 |
| 4 | 549148 (control) | Yes | 26 | 25 | 26 |

Survival Rate

The survival rates of the mice were regularly monitored. Results are presented in the table below. Treatment with the KEAP1 ASOs did not result in any adverse effect on survival compared to the naive control group.

TABLE 43

| | | Survival rate (% of naïve control) | | | |
|---|---|---|---|---|---|
| Group# | ASO | Bleomycin | Day 17 | Day 24 | Day 30 |
| 1 | No | No | 100 | 100 | 100 |
| 2 | No | Yes | 100 | 100 | 95 |
| 3 | 645938 (Keap1) | Yes | 100 | 100 | 100 |
| 4 | 549148 (control) | Yes | 100 | 94 | 88 |

Several endpoints were measured in the lungs to examine the effects of targeting KEAP1. Mice were perfused with 10 mL of cold PBS through the right ventricle. After the lung was cleared of blood, 1 mL of cold William E buffer (ThermoFisher Scientific) with 1 mg/mL Pronase (Roche) was injected into trachea until the lung was inflated. After 30 min of incubation at 37° C., the lung was removed, minced, and incubated in William E buffer with 0.2 mg/mL DNase I (Roche), 2 mg/mL collagenase (Roche), 0.1 U/mL elastase (Roche) for 10 min. After a slow speed spin (2,000 rpm for 10 min), the cell pellet was washed twice with Wash buffer (cold PBS, pH 7.2 with 0.2 mg/mL DNase I) and resuspended in 2.3 mL Wash buffer. The cell suspension was layered on top of 7% (w/v) OptiPrep gradient (Sigma-Aldrich) and centrifuged at 3,000 rpm for 25 min using slow acceleration and deceleration modes. Cell fractions at 7%, 10%, 16%, and 40% (w/v) were collected and diluted into cold Wash buffer. After centrifugation at 2,000 rpm for 10 min, the cell pellet was dissolved in RLT buffer (Qiagen) with 1% 2-mercaptoethanol (Sigma-Aldrich), and RNA was purified. Target mRNA knockdown of KEAP1 was measured in addition to the effect on various fibrosis markers (mRNA). Differential cell counts of inflammatory cells in the lung were performed on the bronchoalveolar lavage (BAL) fluid to evaluate the effects of the ASOs targeting murine KEAP1 on cell recruitment to the airways.

RNA Analysis

At the end of the treatment period, RNA was extracted from lung tissue for quantitative real-time PCR analysis of RNA expression for KEAP1. Murine KEAP1 primer probe set RTS4398_MGB was used to measure RNA levels. Results are presented in the table below as percent inhibition of KEAP1, relative to PBS control, normalized against RIBOGREEN®. There was a 75% reduction of KEAP1 mRNA in the lungs of the mice group treated with KEAP1 ASO in comparison to the control group.

Markers for fibrosis, such as collagen-1, SMA, Timp1, and TGFβ, were also measured. The results are presented below and demonstrate reduction in several markers of fibrosis after treatment with KEAP1 ASO.

TABLE 44

| | | Levels of fibrosis markers (% of naive control) | | | | |
|---|---|---|---|---|---|---|
| Group# | ASO | Bleomycin | Collagen-1 | SMA | Timp1 | TGFβ |
| 1 | No | No | 100 | 100 | 100 | 100 |
| 2 | No | Yes | 561 | 190 | 5012 | 5012 |
| 3 | 645938 (Keap1) | Yes | 167 | 201 | 701 | 701 |
| 4 | 549148 (control) | Yes | 276 | 173 | 1293 | 1293 |

Example 10: ASO Inhibition of KEAP1 in a Western Diet Model

ASOs described in the studies above were evaluated for their effect on C57BL/6 mice fed with a high fat/high cholesterol diet.

Treatment

C57BL/6 mice were fed a high fat/high cholesterol diet (Diet 88137; 42% Kcal from fat) for 5 months prior to dosing. The mice were then divided into treatment groups consisting of 6-9 animals each based on body weight, plasma ALT, insulin, glucose, leptin, and albumin. Mice were injected subcutaneously once a week for 12 weeks with 25 mg/kg of ISIS 549144 control oligonucleotide, or with 25 mg/kg or 40 mg/kg of ISIS 645938, and one group of were injected with PBS as a control to which the antisense oligonucleotide treated groups are compared. Several clinical endpoints were measured over the course of the study.

KEAP1 RNA Analysis

At the end of the treatment period, RNA was extracted from liver, kidney, heart, white adipose tissue (WAT), lung, muscle, and pancreas for quantitative real-time PCR analysis of mRNA expression of KEAP1. Results are presented as percent of KEAP1, relative to PBS control, normalized against Cyclophilin A. ISIS 645938 significantly reduced Keap1 expression in the multiple tissues in a dose responsive manner.

TABLE 45

| | | % inhibition (compared to control) of Keap1 mRNA expression | | | | | | |
|---|---|---|---|---|---|---|---|---|
| | Dose | KEAP1 mRNA (% saline) | | | | | | |
| Treatment | (mg/kg) | Liver | Kidney | Heart | WAT | Lung | Muscle | Pancreas |
| 549144 | 25 | 0 | 0 | 0 | 0 | 0 | 0 | 0 |
| 645938 | 25 | 91 | 73 | 66 | 68 | 61 | 71 | 3 |
| 645938 | 40 | 94 | 78 | 77 | 70 | 72 | 81 | 10 |

NQO1 RNA Analysis

At the end of the treatment period, RNA was extracted from heart, liver, kidney, white adipose tissue (WAT), lung, and muscle for quantitative real-time PCR analysis of mRNA expression of NQO1. Results are presented as percent of NQO1, relative to PBS control, normalized against Cyclophilin A. ISIS 645938 was shown to upregulate NQO1 expression in multiple tissues. The result shows that ASO inhibition of KEAP1 decreases KEAP-mediated repression of Nrf2 activity and allows expression of Nrf2 downstream genes such as NQO1.

TABLE 46

% increase in expression of NQO1

| Treatment | Dose (mg/kg) | KEAP1 mRNA (% saline) | | | | | |
|---|---|---|---|---|---|---|---|
| | | Liver | Kidney | Heart | WAT | Lung | Muscle | Pancreas |
| 549144 | 25 | 0 | 0 | 0 | 0 | 0 | 0 | 0 |
| 645938 | 25 | 504 | 442 | 6 | 222 | 165 | 46 | 134 |
| 645938 | 40 | 492 | 431 | −8 | 364 | 202 | 24 | 219 |

GSTA1 RNA Analysis

At the end of the treatment period, RNA was extracted from liver, kidney, heart, white adipose tissue (WAT), lung, muscle, and pancreas for quantitative real-time PCR analysis of mRNA expression of GSTA1. Results are presented as percent of GSTA1, relative to PBS control, normalized against Cyclophilin A. ISIS 645938 was shown to upregulate GSTA1 expression.

TABLE 47

% increase in expression of GSTA1

| Treatment | Dose (mg/kg) | KEAP1 mRNA (% saline) | | | | | |
|---|---|---|---|---|---|---|---|
| | | Liver | Kidney | Heart | WAT | Lung | Muscle | Pancreas |
| 549144 | 25 | 0 | 0 | 0 | 0 | 0 | 0 | 0 |
| 645938 | 25 | 641 | 958 | 30 | 282 | 17 | 542 | 23 |
| 645938 | 40 | 463 | 1142 | 22 | 647 | 32 | 382 | 29 |

BODY and Organ Weights

Body weights were measured weekly. Kidney, liver, spleen and white adipose tissue (WAT) weights were measured at the end of the study and are presented as percent body weight (% BW) in the table below. Results indicate that treatment with Keap1 antisense oligonucleotide reduced the body weight in the mice.

TABLE 48

Body weight (g) of mice fed a western diet

| Treatment | Dose (mg/kg) | Week 1 | Week 5 | Week 9 | Week 12 |
|---|---|---|---|---|---|
| 549144 | 25 | 50 | 49 | 53 | 52 |
| 645938 | 25 | 50 | 45 | 47 | 46 |
| 645938 | 40 | 48 | 42 | 43 | 40 |

TABLE 49

Organ weights of mice fed a western diet

| Treatment | Dose (mg/kg) | Liver (% BW) | Kidney (% BW) | Spleen (% BW) | WAT (% BW) |
|---|---|---|---|---|---|
| 549144 | 25 | 9.2 | 0.9 | 0.3 | 4.2 |
| 645938 | 25 | 10.3 | 1.1 | 0.6 | 4.9 |
| 645938 | 40 | 10.2 | 1.3 | 0.8 | 3.6 |
| Non-treated | — | 8.9 | 0.9 | 0.4 | 3.9 |

Plasma Chemistry Markers

To evaluate the effect of treatment with ISIS oligonucleotides on plasma levels of various biomarkers of liver and kidney function, plasma levels of liver transaminases (ALT and AST), albumin, and bilirubin were measured at 12 weeks using an automated clinical chemistry analyzer (Hitachi Olympus AU400e, Melville, N.Y.). 'n.d.' indicates no data for that mice group.

Overall, the plasma chemistry results indicate that ISIS 645938 reduced plasma ALT and albumin levels, and was tolerable in the mice.

TABLE 50

Plasma markers mice fed a western diet

| Treatment | Dose (mg/kg) | ALT (IU/L) | AST (IU/L) | Albumin (g/dL) | Total bilirubin (mg/dL) |
|---|---|---|---|---|---|
| 549144 | 25 | 303 | 209 | 2.7 | 0.18 |
| 645938 | 25 | 129 | 221 | 2.4 | 0.09 |
| 645938 | 40 | 113 | 240 | 2.1 | 0.07 |
| Non-treated | — | 454 | 368 | 2.9 | n.d. |

Intraperitoneal Glucose Tolerance Test (GTT)

To assess insulin sensitivity in the mice, IPGTT was performed to measure the clearance of an intraperitoneally injected glucose load from the body. Mice were fasted for approximately 16 hours and fasted blood glucose levels were measured before intraperitoneal injection of a solution of glucose. Blood glucose levels were measured at different time points for 2 hours. The test was performed at week 5 and week 10. In both instances, KEAP1 ASO treated mice were able to clear glucose at a higher rate than control treated mice, indicating an improvement in insulin sensitivity with KEAP1 ASO treatment. The Area Under the Curve (AUC) for both weeks is also presented and demonstrates improvement in insulin sensitivity in this model.

TABLE 51

Blood glucose levels (mg/dL) at week 10 in mice fed a western diet

| Treatment | Dose (mg/kg) | 0 min | 15 min | 30 min | 60 min | 90 min | 120 min |
|---|---|---|---|---|---|---|---|
| 549144 | 25 | 144 | 288 | 291 | 280 | 271 | 264 |
| 645938 | 25 | 163 | 284 | 288 | 238 | 186 | 166 |
| 645938 | 40 | 142 | 282 | 273 | 223 | 174 | 158 |

TABLE 52

IPGTT AUC in mice fed a western diet

| Treatment | Dose (mg/kg) | 5 week | 10 week |
|---|---|---|---|
| 549144 | 25 | 25448 | 32429 |
| 645938 | 25 | 19803 | 27151 |
| 645938 | 40 | 21480 | 28180 |

Hepatic Lipid Accumulation

To assess the effect on lipid accumulation in the liver of the mice, levels of triglycerides, free fatty acids, cholesterol ester, and free cholesterol in the liver were measured. The data is presented in the table below. KEAP1 ASO treated mice had significantly reduced levels of liver lipid accumulation.

TABLE 53

Liver lipid levels (mg/g liver) in mice fed a western diet

| Treatment | Dose (mg/kg) | Triglycerides | Free cholesterol | Free Fatty Acids | Cholesterol Ester |
|---|---|---|---|---|---|
| 549144 | 25 | 191 | 2.23 | 9.32 | 31 |
| 645938 | 25 | 75 | 1.55 | 2.45 | 7 |
| 645938 | 40 | 27 | 1.23 | 0.56 | 2 |

Hepatic Lipogenic Gene Expression

To assess the effect on lipogenic gene expression in the liver of the mice, gene expression levels of FAS, SREBP1c, and ACC1 in the liver were measured. The data is presented in the table below. KEAP1 ASO treated mice had significantly reduced mRNA expression levels of all these lipogenic genes, indicating reduced lipid generation.

TABLE 54

% inhibition of lipogenic gene expression (compared to control) in the liver

| Treatment | Dose (mg/kg) | FAS | SREBP1c | ACC1 |
|---|---|---|---|---|
| 549144 | 25 | 0 | 0 | 0 |
| 645938 | 25 | 58 | 50 | 44 |
| 645938 | 40 | 69 | 66 | 64 |

Expression Levels of Hepatic Fibrosis Markers

To assess the effect on fibrosis in the liver of the mice, gene expression levels of COL1a1, COL1a2, αSMA, TGFβ, TIMP1, and TIMP2 in the liver were measured. Protein levels of fibrosis markers, TIMP1, glutathione, and hydroxyproline were also measured. The data is presented in the tables below. KEAP1 ASO treated mice had significantly reduced mRNA levels of all the fibrosis markers indicating reduction in fibrosis in the liver. The levels of glutathione, an important antioxidant, are increased in these mice, while TIMP1 and hydroxyproline levels were reduced, confirming that antisense inhibition of KEAP1 reduced hepatic fibrosis in this model.

TABLE 55

% inhibition of gene expression of fibrosis markers (compared to control) in the liver

| Treatment | Dose (mg/kg) | COL1a1 | COL1a2 | αSMA | TGFβ | TIMP1 | TIMP2 |
|---|---|---|---|---|---|---|---|
| 549144 | 25 | 0 | 0 | 0 | 0 | 0 | 0 |
| 645938 | 25 | 63 | 55 | 18 | 41 | 65 | 63 |
| 645938 | 40 | 74 | 70 | 18 | 50 | 74 | 70 |

TABLE 56

Protein expression of fibrosis markers in the liver

| Treatment | Dose (mg/kg) | TIMP1 (pg/mg liver protein) | Glutathione (μmol/g protein) | Hydroxyproline (μmol/g protein) |
|---|---|---|---|---|
| 549144 | 25 | 49.7 | 11.2 | 1.9 |
| 645938 | 25 | 27.9 | 30.6 | 1.3 |
| 645938 | 40 | 23.1 | 28.0 | 1.0 |

What is claimed is:

1. A method of treating NASH or NAFLD in an animal comprising administering to the animal a therapeutically effective amount of a compound comprising a modified oligonucleotide wherein the modified oligonucleotide consists of 12 to 30 linked nucleosides and is complementary to a KEAP1 nucleic acid, thereby treating the NASH or NAFLD in the animal.

2. The method of claim 1, wherein administering the compound reduces liver triglyceride, liver cholesterol, or liver fibrosis.

3. The method of claim 1, wherein the individual is human.

4. The method of claim 1, wherein the compound is single stranded.

5. The method of claim 1, wherein the compound is double stranded.

6. The method of claim 1, wherein the modified oligonucleotide comprises at least one modified internucleoside linkage, at least one modified sugar moiety, or at least one modified nucleobase.

7. The method of claim 6, wherein the at least one modified internucleoside linkage is a phosphorothioate internucleoside linkage, the at least one modified sugar is a bicyclic sugar or 2'-O-methoxyethyl and the at least one modified nucleobase is a 5-methylcytosine.

8. The method of claim 6, wherein at least one modified sugar comprises a 4'-CH(CH$_3$)—O-2' bridge or a 4'-(CH$_2$)$_n$—O-2' bridge, wherein n is 1 or 2.

9. The method of claim 1, wherein the modified oligonucleotide comprises:
a gap segment consisting of linked deoxynucleosides;
a 5' wing segment consisting of linked nucleosides;
a 3' wing segment consisting linked nucleosides;
wherein the gap segment is positioned immediately adjacent to and between the 5' wing segment and the 3' wing segment and wherein each nucleoside of each wing segment comprises a modified sugar.

10. The method of claim 1, wherein the KEAP1 nucleic acid has the nucleobase sequence of SEQ ID NO: 1 or SEQ ID NO: 2.

11. The method of claim 1, wherein the modified oligonucleotide is at least 90% complementary to the KEAP1 nucleic acid.

12. The method of claim 10, wherein the modified oligonucleotide is at least 90% complementary to the KEAP1 nucleic acid.

13. The method of claim 1, wherein the modified oligonucleotide is at least 95% complementary to the KEAP1 nucleic acid.

14. The method of claim 10, wherein the modified oligonucleotide is at least 95% complementary to the KEAP1 nucleic acid.

15. The method of claim 1, wherein the modified oligonucleotide is 100% complementary to the KEAP1 nucleic acid.

16. The method of claim 10, wherein the modified oligonucleotide is 100% complementary to the KEAP1 nucleic acid.

17. The method of claim 10, wherein the compound is single stranded.

18. The method of claim 10, wherein the compound is double stranded.

19. The method of claim 10, wherein the modified oligonucleotide comprises at least one modified internucleoside linkage, at least one modified sugar moiety, or at least one modified nucleobase.

20. The method of claim 19, wherein the at least one modified internucleoside linkage is a phosphorothioate internucleoside linkage, the at least one modified sugar is a bicyclic sugar or 2'-O-methoxyethyl and the at least one modified nucleobase is a 5-methylcytosine.

21. The method of claim 19, wherein at least one modified sugar comprises a 4'-CH(CH$_3$)-O-2' bridge or a 4'-(CH$_2$)$_n$O-2' bridge, wherein n is 1 or 2.

22. The method of claim 10, wherein the modified oligonucleotide comprises:
a gap segment consisting of linked deoxynucleosides;
a 5' wing segment consisting of linked nucleosides;
a 3' wing segment consisting linked nucleosides;
wherein the gap segment is positioned immediately adjacent to and between the 5' wing segment and the 3' wing segment and wherein each nucleoside of each wing segment comprises a modified sugar.

23. The method of claim 12, wherein the compound is single stranded.

24. The method of claim 12, wherein the compound is double stranded.

25. The method of claim 12, wherein the modified oligonucleotide comprises at least one modified internucleoside linkage, at least one modified sugar moiety, or at least one modified nucleobase.

26. The method of claim 25, wherein the at least one modified internucleoside linkage is a phosphorothioate internucleoside linkage, the at least one modified sugar is a bicyclic sugar or 2'-O-methoxyethyl and the at least one modified nucleobase is a 5-methylcytosine.

27. The method of claim 25, wherein at least one modified sugar comprises a 4'-CH(CH$_3$)-O-2' bridge or a 4'-(CH$_2$)$_n$-O-2' bridge, wherein n is 1 or 2.

28. The method of claim 12, wherein the modified oligonucleotide comprises:
a gap segment consisting of linked deoxynucleosides;
a 5' wing segment consisting of linked nucleosides;
a 3' wing segment consisting linked nucleosides;
wherein the gap segment is positioned immediately adjacent to and between the 5' wing segment and the 3' wing segment and wherein each nucleoside of each wing segment comprises a modified sugar.

29. The method of claim 14, wherein the compound is single stranded.

30. The method of claim 14, wherein the compound is double stranded.

31. The method of claim 14, wherein the modified oligonucleotide comprises at least one modified internucleoside linkage, at least one modified sugar moiety, or at least one modified nucleobase.

32. The method of claim 31, wherein the at least one modified internucleoside linkage is a phosphorothioate internucleoside linkage, the at least one modified sugar is a bicyclic sugar or 2'-O-methoxyethyl and the at least one modified nucleobase is a 5-methylcytosine.

33. The method of claim 31, wherein at least one modified sugar comprises a 4'-CH(CH$_3$)-O-2' bridge or a 4'-(CH$_2$)$_n$-O-2' bridge, wherein n is 1 or 2.

34. The method of claim 14, wherein the modified oligonucleotide comprises:
- a gap segment consisting of linked deoxynucleosides;
- a 5' wing segment consisting of linked nucleosides;
- a 3' wing segment consisting linked nucleosides;
- wherein the gap segment is positioned immediately adjacent to and between the 5' wing segment and the 3' wing segment and wherein each nucleoside of each wing segment comprises a modified sugar.

35. The method of claim 16, wherein the compound is single stranded.

36. The method of claim 16, wherein the compound is double stranded.

37. The method of claim 16, wherein the modified oligonucleotide comprises at least one modified internucleoside linkage, at least one modified sugar moiety, or at least one modified nucleobase.

38. The method of claim 37, wherein the at least one modified internucleoside linkage is a phosphorothioate internucleoside linkage, the at least one modified sugar is a bicyclic sugar or 2'-O-methoxyethyl and the at least one modified nucleobase is a 5-methylcytosine.

39. The method of claim 37, wherein at least one modified sugar comprises a 4'-CH(CH$_3$)-O-2' bridge or a 4'-(CH$_2$)$_n$-O-2' bridge, wherein n is 1 or 2.

40. The method of claim 16, wherein the modified oligonucleotide comprises:
- a gap segment consisting of linked deoxynucleosides;
- a 5' wing segment consisting of linked nucleosides;
- a 3' wing segment consisting linked nucleosides;
- wherein the gap segment is positioned immediately adjacent to and between the 5' wing segment and the 3' wing segment and wherein each nucleoside of each wing segment comprises a modified sugar.

* * * * *